(12) United States Patent
Blomgren et al.

(10) Patent No.: US 8,426,424 B2
(45) Date of Patent: Apr. 23, 2013

(54) CERTAIN SUBSTITUTED AMIDES, METHOD OF MAKING, AND METHOD OF USE THEREOF

(75) Inventors: Peter A. Blomgren, North Branford, CT (US); David R. Brittelli, Branford, CT (US); Kevin S. Currie, North Branford, CT (US); Seung H. Lee, Branford, CT (US); Jeffrey E. Kropf, Branford, CT (US); Scott A. Mitchell, East Haven, CT (US); Aaron C. Schmitt, Hamden, CT (US); Xiaojing Wang, Foster City, CA (US); Jianjun Xu, Madison, CT (US); Zhongdong Zhao, Guilford, CT (US); Pavel E. Zhichkin, Delmar, NY (US)

(73) Assignees: CGI Pharmaceuticals, Inc., Branford, CT (US); Genentech, Inc., South San Francisco, CA (US)

( * ) Notice: Subject to any disclaimer, the term of this patent is extended or adjusted under 35 U.S.C. 154(b) by 17 days.

(21) Appl. No.: 12/991,232

(22) PCT Filed: May 6, 2009

(86) PCT No.: PCT/US2009/043008
§ 371 (c)(1),
(2), (4) Date: Jan. 24, 2011

(87) PCT Pub. No.: WO2009/137596
PCT Pub. Date: Nov. 12, 2009

(65) Prior Publication Data
US 2011/0118233 A1 May 19, 2011

Related U.S. Application Data

(60) Provisional application No. 61/050,791, filed on May 6, 2008.

(51) Int. Cl.
*A61K 31/4965* (2006.01)
*C07D 401/00* (2006.01)
*C07D 403/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)

(52) U.S. Cl.
USPC .................................. 514/255.05; 544/405

(58) Field of Classification Search .................. None
See application file for complete search history.

(56) References Cited

FOREIGN PATENT DOCUMENTS

| WO | WO-2006 099075 | 9/2006 |
| WO | WO-2008 033834 | 3/2008 |
| WO | WO-2008 033857 | 3/2008 |
| WO | WO-2008 033858 | 3/2008 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Chawla et. al. Current Research & Information on Pharmaceutical Science, 2004, 5(1), p. 9, col. 2, para.1.*
Newman et. al.; Drug Discovery Today; 2003, 8(19) p. 898, col. 2, Para.3.).*
Vippagunta et. al. Advanced Drug Delivery Reviews 48 (2001) 3-26.*
International Search Report for PCT/US2009/043008 dated Oct. 27, 2009.

* cited by examiner

*Primary Examiner* — Jeffrey Murray
(74) *Attorney, Agent, or Firm* — Millen, White, Zelano & Branigan, P.C.

(57) ABSTRACT

The invention relates to compounds of the following Formula I

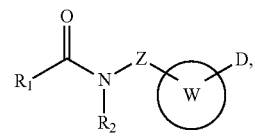

wherein $R_1$, $R_2$, Z, W, and D are defined herein, that inhibit Btk and therefore are useful in the treatment of diseases responsive to inhibition of Btk activity such as cancer. The invention also relates to pharmaceutical compositions comprising at least one compound of Formula I, together with at least one pharmaceutically acceptable vehicle chosen from carriers, adjuvants, and excipients, as well as methods of treating patients suffering from certain diseases responsive to inhibition of Btk activity and/or B-cell activity are described, and methods for determining the presence of Btk in a sample.

30 Claims, No Drawings

CERTAIN SUBSTITUTED AMIDES, METHOD OF MAKING, AND METHOD OF USE THEREOF

This application claims the benefit of the filing date of U.S. Provisional Application Ser. No. 61/050,791 filed May 6, 2008, which is incorporated by reference herein.

Provided herein are certain substituted amides and related compounds, compositions comprising such compounds, and methods of their use.

Protein kinases, the largest family of human enzymes, encompass well over 500 proteins. Bruton's Tyrosine Kinase (Btk) is a member of the Tec family of tyrosine kinases, and is a regulator of early B-cell development as well as mature B-cell activation, signaling, and survival.

B-cell signaling through the B-cell receptor (BCR) can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice can also be resistant to developing collagen-induced arthritis and can be less susceptible to *Staphylococcus*-induced arthritis.

A large body of evidence supports the role of B-cells and the humoral immune system in the pathogenesis of autoimmune and/or inflammatory diseases. Protein-based therapeutics (such as Rituxan) developed to deplete B-cells, represent an approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in osteoclasts, mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma. In addition, Btk has been reported to play a role in apoptosis; thus, inhibition of Btk activity can be useful for cancer, as well as the treatment of B-cell lymphoma and leukemia. Moreover, given the role of Btk in osteoclast function, the inhibition of Btk activity can be useful for the treatment of bone disorders such as osteoporosis.

Provided is a compound of Formula I:

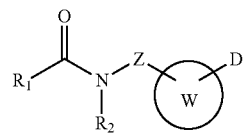

(Formula I)

and pharmaceutically acceptable salts, solvates, chelates, non-covalent complexes, prodrugs, and mixtures thereof, wherein $R_1$ is chosen from:

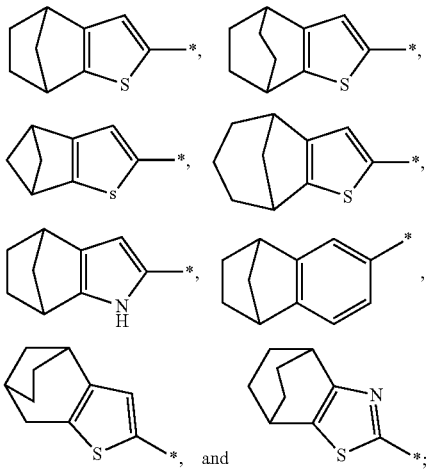

$R_2$ is H or $CH_3$;

Z is chosen from phenylene and pyridylidene wherein phenylene and pyridylidene are optionally substituted with one or more groups independently chosen from CN, halo, hydroxyl, optionally substituted lower alkyl, and optionally substituted lower alkoxy;

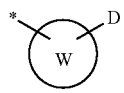

is chosen from

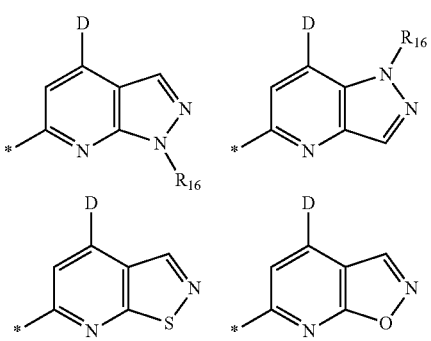

-continued
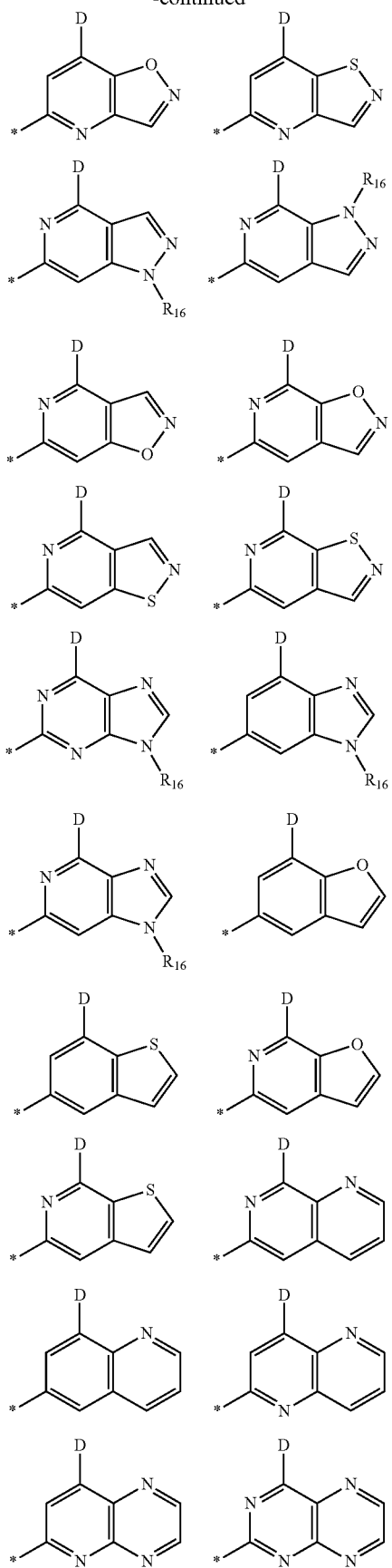
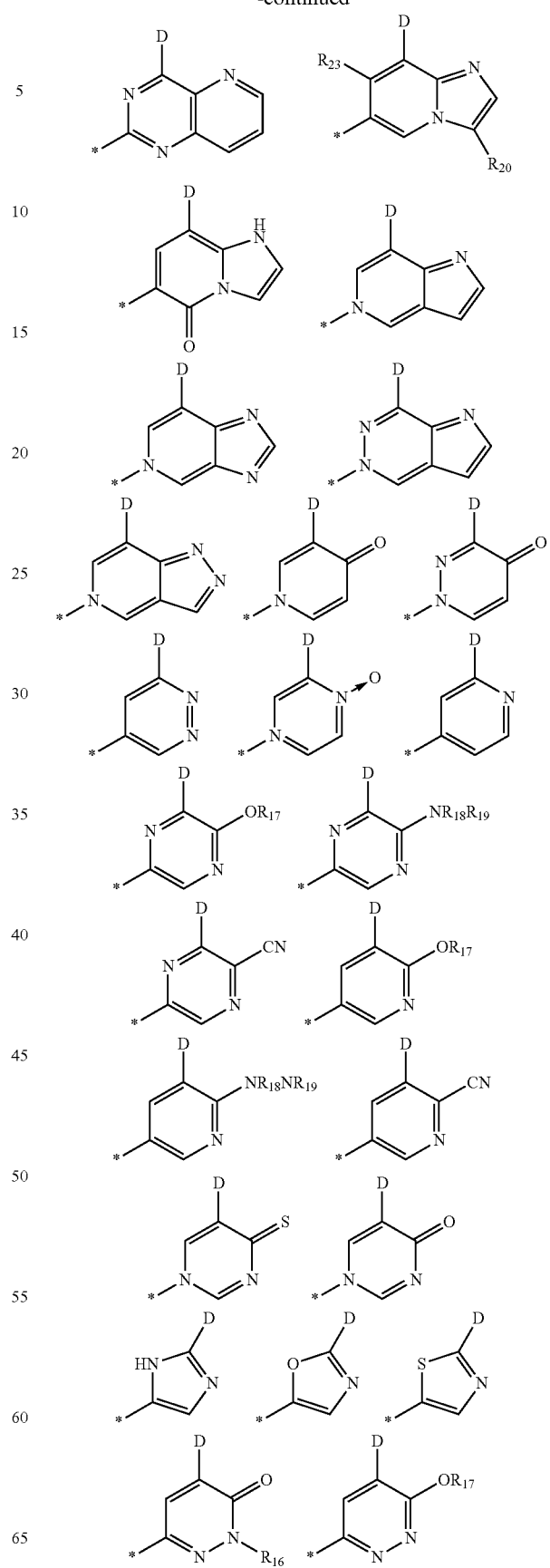

-continued

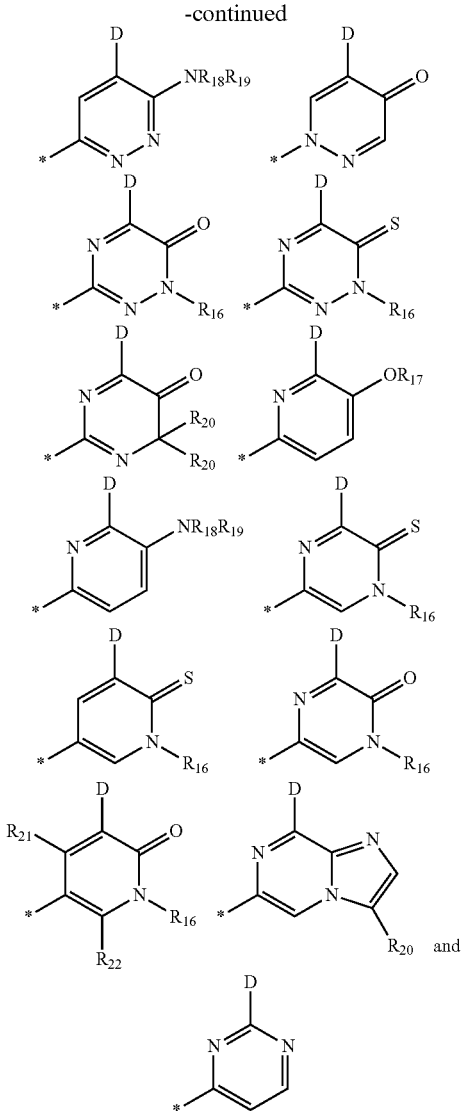

each of which is optionally substituted with one or two groups chosen from hydroxy, cyano, halo, optionally substituted lower alkyl, and optionally substituted lower alkoxy;

each $R_{16}$ is independently chosen from hydrogen, cyano, optionally substituted cycloalkyl, and optionally substituted lower alkyl;

$R_{17}$, $R_{18}$, $R_{19}$, $R_{21}$, $R_{22}$, and $R_{23}$ are independently chosen from hydrogen and optionally substituted lower alkyl;

each $R_{20}$ is independently chosen from hydrogen, hydroxy, cyano, halo, optionally substituted lower alkyl, and optionally substituted lower alkoxy;

D is —$NHR_7$; and $R_7$ is chosen from optionally substituted aryl and optionally substituted heteroaryl.

Provided is a pharmaceutical composition, comprising a compound of Formula I, together with at least one pharmaceutically acceptable vehicle chosen from carriers, adjuvants, and excipients.

Provided is a packaged pharmaceutical composition, comprising a pharmaceutical composition described herein; and instructions for using the composition to treat a patient suffering from a disease responsive to inhibition of Btk activity.

Provided is a method for treating a patient having a disease responsive to inhibition of Btk activity, comprising administering to the patient an effective amount of a compound of Formula I.

Provided is a method for treating a patient having a disease chosen from cancer, bone disorders, autoimmune diseases, inflammatory diseases, acute inflammatory reactions, and allergic disorders comprising administering to the patient an effective amount of a compound of Formula I.

Provided is a method for increasing sensitivity of cancer cells to chemotherapy, comprising administering to a patient undergoing chemotherapy with a chemotherapeutic agent an amount of a compound of Formula I sufficient to increase the sensitivity of cancer cells to the chemotherapeutic agent.

Provided is a method of reducing medication error and enhancing therapeutic compliance of a patient being treated for a disease responsive to inhibition of Btk activity, the method comprising providing a packaged pharmaceutical preparation described herein wherein the instructions additionally include contraindication and adverse reaction information pertaining to the packaged pharmaceutical composition.

Provided is a method for inhibiting ATP hydrolysis, the method comprising contacting cells expressing Btk with a compound of Formula I in an amount sufficient to detectably decrease the level of ATP hydrolysis in vitro.

Provided is a method for determining the presence of Btk in a sample, comprising contacting the sample with a compound of Formula I under conditions that permit detection of Btk activity, detecting a level of Btk activity in the sample, and therefrom determining the presence or absence of Btk in the sample.

Provided is a method for inhibiting B-cell activity comprising contacting cells expressing Btk with a compound of Formula I in an amount sufficient to detectably decrease B-cell activity in vitro.

As used in the present specification, the following words and phrases are generally intended to have the meanings as set forth below, except to the extent that the context in which they are used indicates otherwise. The following abbreviations and terms have the indicated meanings throughout:

As used herein, when any variable occurs more than one time in a chemical formula, its definition on each occurrence is independent of its definition at every other occurrence. In accordance with the usual meaning of "a" and "the" in patents, reference, for example, to "a" kinase or compound or "the" kinase or compound is inclusive of one or more kinases or compounds.

"*" associated with variable $R_1$ indicates the point of attachment of $R_1$ to the carbonyl carbon of the group —C(O)N($R_2$)—. "*" associated with ring W indicates the point of attachment of ring W to Z of the group —Z—N($R_2$)C(O)$R_1$. "*" associated with variable B indicates the point of attachment of B to L of the group "-L-G".

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to four carbons.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having one to four carbons.

"Mono- and di-alkylcarboxamide" encompasses a group of the formula —(C=O)NR$_a$R$_b$ where R$_a$ and R$_b$ are independently chosen from hydrogen and alkyl groups of the indicated number of carbon atoms, provided that R$_a$ and R$_b$ are not both hydrogen.

By "alkylthio" is meant an alkyl group of the indicated number of carbon atoms attached through a sulfur bridge.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3$(C=O)—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —$NH_2$.

"Mono- and di-(alkyl)amino" encompasses secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

"Mono- and di-(alkyl)aminoalkyl" encompasses mono- and di-(alkyl)amino as defined above linked to an alkyl group.

By "amino(alkyl)" is meant an amino group linked to an alkyl group having the indicated number of carbons. Similarly "hydroxyalkyl" is a hydroxy group linked to an alkyl group.

The term "aminocarbonyl" refers to the group —CONR$^b$R$^c$, where

R$^b$ is chosen from H, optionally substituted $C_1$-$C_6$ alkyl, optionally substituted aryl, and optionally substituted heteroaryl; and R$^c$ is chosen from hydrogen and optionally substituted $C_1$-$C_4$ alkyl; or R$^b$ and R$^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

"Aryl" encompasses:
5- and 6-membered carbocyclic aromatic rings, for example, benzene;
bicyclic ring systems wherein at least one ring is carbocyclic and aromatic, for example, naphthalene, indane, and tetralin; and
tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Heteroaryl" encompasses:
- 5- to 7-membered aromatic, monocyclic rings containing one or more, for example, from 1 to 4, or in certain embodiments, from 1 to 3, heteroatoms chosen from N, O, and S, with the remaining ring atoms being carbon; and
- bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide ($-O^-$) substituents, such as pyridinyl N-oxides.

In the term "heteroarylalkyl," heteroaryl and alkyl are as defined herein, and the point of attachment is on the alkyl group. This term encompasses, but is not limited to, pyridylmethyl, thiophenylmethyl, and (pyrrolyl)1-ethyl.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

"Carbamimidoyl" refers to the group $-C(=NH)-NH_2$.

"Substituted carbamimidoyl" refers to the group $-C(=NR^e)-NR^fR^g$ where $R^e$, $R^f$, and $R^g$ is independently chosen from: hydrogen optionally substituted alkyl, optionally substituted cycloalkyl, optionally substituted aryl, optionally substituted heteroaryl, and optionally substituted heterocycloalkyl, provided that at least one of $R^e$, $R^f$, and $R^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

$-R^{a'}$, $-OR^{b'}$, $-O(C_1-C_2$ alkyl)O— (e.g., methylenedioxy-), $-SR^{b'}$, guanidine, guanidine wherein one or more of the guanidine hydrogens are replaced with a lower-alkyl group, $-NR^{b'}R^{c'}$, halo, cyano, nitro, $-COR^{b'}$, $-CO_2R^{b'}$, $-CONR^{b'}R^{c'}$, $-OCOR^{b'}$, $-OCO_2R^{a'}$, $-OCONR^{b'}R^{c'}$, $-NR^{c'}COR^{b'}$, $-NR^{c'}CO_2R^{a'}$, $-NR^{c'}CONR^{b'}R^{c'}$, $-CO_2R^{b'}$, $-CONR^{b'}R^{c'}$, $-NR^{c'}COR^{b'}$, $-SOR^{a'}$, $-SO_2R^{a'}$, $-SO_2NR^{b'}R^{c'}$, and $-NR^{c'}SO_2R^{a'}$, where $R^{a'}$ is chosen from optionally substituted $C_1$-$C_6$ alkyl, optionally substituted aryl, and optionally substituted heteroaryl;

$R^{b'}$ is chosen from H, optionally substituted $C_1$-$C_6$ alkyl, optionally substituted aryl, and optionally substituted heteroaryl; and $R^{c'}$ is independently chosen from hydrogen and optionally substituted $C_1$-$C_4$ alkyl; or $R^{b'}$ and $R^{c'}$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, $-OC_1$-$C_4$ alkyl, $-OC_1$-$C_4$ alkylphenyl, $-C_1$-$C_4$ alkyl-OH, $-OC_1$-$C_4$ haloalkyl, halo, $-OH$, $-NH_2$, $-C_1$-$C_4$ alkyl-$NH_2$, $-N(C_1$-$C_4$ alkyl)($C_1$-$C_4$ alkyl), $-NH(C_1$-$C_4$ alkyl), $-N(C_1$-$C_4$ alkyl)($C_1$-$C_4$ alkylphenyl), $-NH(C_1$-$C_4$ alkylphenyl), cyano, nitro, oxo (as a substitutent for cycloalkyl, heterocycloalkyl, or heteroaryl), $-CO_2H$, $-C(O)OC_1$-$C_4$ alkyl, $-CON(C_1$-$C_4$ alkyl)($C_1$-$C_4$ alkyl), $-CONH(C_1$-$C_4$ alkyl), $-CONH_2$, $-NHC(O)(C_1$-$C_4$ alkyl), $-NHC(O)(phenyl)$, $-N(C_1$-$C_4$ alkyl)C(O)($C_1$-$C_4$ alkyl), $-N(C_1$-$C_4$ alkyl)C(O)(phenyl), $-C(O)C_1$-$C_4$ alkyl, $-C(O)C_1$-$C_4$ phenyl, $-C(O)C_1$-$C_4$ haloalkyl, $-OC(O)C_1$-$C_4$ alkyl, $-SO_2(C_1$-$C_4$ alkyl), $-SO_2(phenyl)$, $-SO_2(C_1$-$C_4$ haloalkyl), $-SO_2NH_2$, $-SO_2NH(C_1$-$C_4$ alkyl), $-SO_2NH(phenyl)$, $-NHSO_2(C_1$-$C_4$ alkyl), $-NHSO_2(phenyl)$, and $-NHSO_2(C_1$-$C_4$ haloalkyl).

The term "sulfanyl" includes the groups: $-S$-(optionally substituted ($C_1$-$C_6$)alkyl), $-S$-(optionally substituted aryl), $-S$-(optionally substituted heteroaryl), and $-S$-(optionally substituted heterocycloalkyl). Hence, sulfanyl includes the group $C_1$-$C_6$ alkylsulfanyl.

The term "sulfinyl" includes the groups: $-S(O)-H$, $-S(O)$-(optionally substituted ($C_1$-$C_6$)alkyl), $-S(O)$-optionally substituted aryl), $-S(O)$-optionally substituted heteroaryl), $-S(O)$-(optionally substituted heterocycloalkyl); and $-S(O)$-(optionally substituted amino).

The term "sulfonyl" includes the groups: $-S(O_2)-H$, $-S(O_2)$-(optionally substituted ($C_1$-$C_6$)alkyl), $-S(O_2)$-optionally substituted aryl), $-S(O_2)$-optionally substituted heteroaryl), $-S(O_2)$-(optionally substituted heterocycloalkyl), $-S(O_2)$-(optionally substituted alkoxy), $-S(O_2)$-optionally substituted aryloxy), $-S(O_2)$-optionally substituted heteroaryloxy), —S(O₂)-(optionally substituted heterocyclyloxy); and —S(O₂)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:
—$R^{a''}$, —$OR^{b''}$, —O($C_1$-$C_2$ alkyl)O— (e.g., methylenedioxy-), —$SR^{b''}$, guanidine, guanidine wherein one or more of the guanidine hydrogens are replaced with a lower-alkyl group, —$NR^{b''}R^{c''}$, halo, cyano, nitro, —$COR^{b''}$, —$CO_2R^{b''}$, —$CONR^{b''}R^{c''}$, —$OCOR^{b''}$, —$OCO_2R^{a''}$, —$OCONR^{b''}R^{c''}$, —$NR^{c''}COR^{b''}$, —$NR^{c''}CO_2R^{a''}$, —$NR^{c''}CONR^{b''}R^{c''}$, —$CO_2R^{b''}$, —$CONR^{b''}R^{c''}$, —$NR^{c''}COR^{b''}$, —$SOR^{a''}$, —$SO_2R^{a''}$, —$SO_2NR^{b''}R^{c''}$, and —$NR^{c''}SO_2R^{a''}$, where $R^{a''}$ is chosen from optionally substituted $C_1$-$C_6$ alkyl, optionally substituted aryl, and optionally substituted heteroaryl;

$R^{b''}$ is chosen from H, optionally substituted $C_1$-$C_6$ alkyl, optionally substituted aryl, and optionally substituted heteroaryl; and $R^{c''}$ is chosen from hydrogen and optionally substituted $C_1$-$C_4$ alkyl; or $R^{b''}$ and $R^{c''}$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently chosen from:
—$R^{a°}$, —$OR^{b°}$, —O($C_1$-$C_2$ alkyl)O— (e.g., methylenedioxy-), —$SR^{b°}$, guanidine, guanidine wherein one or more of the guanidine hydrogens are replaced with a lower-alkyl group, —$NR^{b°}R^{c°}$, halo, cyano, nitro, —$COR^{b°}$, —$CO_2R^{b°}$, —$CONR^{b°}R^{c°}$, —$OCOR^{b°}$, —$OCO_2R^{a°}$, —$OCONR^{b°}R^{c°}$, —$NR^{c°}COR^{b°}$, —$NR^{c°}CO_2R^{a°}$, —$NR^{c°}COCONR^{b°}R^{c°}$, —$CO_2R^{b°}$, —$CONR^{b°}R^{c°}$, —$NR^{c°}COR^{b°}$, —$SOR^{a°}$, —$SO_2R^{a°}$, —$SO_2NR^{b°}R^{c°}$, and —$NR^{c°}SO_2R^{a°}$, where $R^{a°}$ is chosen from optionally substituted $C_1$-$C_6$ alkyl, optionally substituted aryl, and optionally substituted heteroaryl;

$R^{b°}$ is chosen from H, optionally substituted $C_1$-$C_6$ alkyl, optionally substituted aryl, and optionally substituted heteroaryl; and $R^{c°}$ is chosen from hydrogen and optionally substituted $C_1$-$C_4$ alkyl; or $R^{b°}$ and $R^{c°}$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

The term "substituted alkoxy" refers to alkoxy wherein the alkyl constituent is substituted (i.e., —O-(substituted alkyl)) wherein "substituted alkyl" refers to alkyl wherein one or more (such as up to 5, for example, up to 3) hydrogen atoms are replaced by a substituent independently chosen from:
—$R^{a\dagger}$, —$OR^{b\dagger}$, —O($C_1$-$C_2$ alkyl)O— (e.g., methylenedioxy-), —$SR^{b\dagger}$, guanidine, guanidine wherein one or more of the guanidine hydrogens are replaced with a lower-alkyl group, —$NR^{b\dagger}R^{c\dagger}$, halo, cyano, nitro, —$COR^{b\dagger}$, —$CO_2R^{b\dagger}$, —$CONR^{b\dagger}R^{c\dagger}$, —$OCOR^{b\dagger}$, —$OCO_2R^{a\dagger}$, —$OCONR^{b\dagger}R^{c\dagger}$, —$NR^{c\dagger}COR^{b\dagger}$, —$NR^{c\dagger}CO_2R^{a\dagger}$, —$NR^{c\dagger}CONR^{b\dagger}R^{c\dagger}$, —$CO_2R^{b\dagger}$, —$CONR^{b\dagger}R^{c\dagger}$, —$NR^{c\dagger}COR^{b\dagger}$, —$SOR^{a\dagger}$, —$SO_2R^{a\dagger}$, —$SO_2NR^{b\dagger}R^{c\dagger}$, and —$NR^{c\dagger}SO_2R^{a\dagger}$, where $R^{a\dagger v}$ is chosen from optionally substituted $C_1$-$C_6$ alkyl, optionally substituted aryl, and optionally substituted heteroaryl;

$R^{b\dagger}$ is chosen from H, optionally substituted $C_1$-$C_6$ alkyl, optionally substituted aryl, and optionally substituted heteroaryl; and $R^{c\dagger}$ is chosen from hydrogen and optionally substituted $C_1$-$C_4$ alkyl; or $R^{b\dagger}$ and $R^{c\dagger}$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl). In some embodiments, a substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of 2-20, such as 2-10, and for example, 2-5. Another substituted alkoxy group is hydroxyalkoxy or —OCH$_2$(CH$_2$)$_y$OH, where y is an integer of 1-10, such as 1-4.

The term "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent chosen independently from:

—$R^{a\dagger\dagger}$, —$OR^{b\dagger\dagger}$, —O($C_1$-$C_2$ alkyl)O— (e.g., methylenedioxy-), —$SR^{b\dagger\dagger}$, guanidine, guanidine wherein one or more of the guanidine hydrogens are replaced with a lower-alkyl group, —$NR^{b\dagger\dagger}R^{c\dagger\dagger}$, halo, cyano, nitro, —$COR^{b\dagger\dagger}$, —$CO_2R^{b\dagger\dagger}$, —$CONR^{b\dagger\dagger}R^{c\dagger\dagger}$, —$OCOR^{b\dagger\dagger}$, —$OCO_2R^{a\dagger\dagger}$, —$OCONR^{b\dagger\dagger}R^{c\dagger\dagger}$, —$NR^{c\dagger\dagger}COR^{b\dagger\dagger}$, —$NR^{c\dagger\dagger}CO_2R^{a\dagger\dagger}$, —$NR^{c\dagger\dagger}CONR^{b\dagger\dagger}R^{c\dagger\dagger}$, —$CO_2R^{b\dagger\dagger}$, —$CONR^{b\dagger\dagger}R^{c\dagger\dagger}$, —$NR^{c\dagger\dagger}COR^{b\dagger\dagger}$, —$SOR^{a\dagger\dagger}$, —$SO_2R^{a\dagger\dagger}$, —$SO_2NR^{b\dagger\dagger}R^{c\dagger\dagger}$, and —$NR^{c\dagger\dagger}SO_2R^{a\dagger\dagger}$, where $R^{a\dagger\dagger}$ is chosen from optionally substituted $C_1$-$C_6$ alkyl, optionally substituted aryl, and optionally substituted heteroaryl;

$R^{b\dagger\dagger}$ is chosen from H, optionally substituted $C_1$-$C_6$ alkyl, optionally substituted aryl, and optionally substituted heteroaryl; and $R^{c\dagger\dagger}$ is chosen from hydrogen and optionally substituted $C_1$-$C_4$ alkyl; or $R^{b\dagger\dagger}$ and $R^{c\dagger\dagger}$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted amino" refers to the group —NHR$^d$ or —NR$^d$R$^d$ where each R$^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, alkoxycarbonyl, sulfinyl and sulfonyl, provided that only one R$^d$ may be hydroxyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^{a\ddagger}$, —$OR^{b\ddagger}$, —O($C_1$-$C_2$ alkyl)O— (e.g., methylenedioxy-), —$SR^{b\ddagger}$, guanidine, guanidine wherein one or more of the guanidine hydrogens are replaced with a lower-alkyl group, —$NR^{b\ddagger}R^{c\ddagger}$, halo, cyano, nitro, —$COR^{b\ddagger}$, —$CO_2R^{b\ddagger}$, —$CONR^{b\ddagger}R^{c\ddagger}$, —$OCOR^{b\ddagger}$, —$OCO_2R^{a\ddagger}$, —$OCONR^{b\ddagger}R^{c\ddagger}$, —$NR^{c\ddagger}COR^{b\ddagger}$, —$NR^{c\ddagger}CO_2R^{a\ddagger}$, —$NR^{c\ddagger}CONR^{b\ddagger}R^{c\ddagger}$, —$CO_2R^{b\ddagger}$, —$CONR^{b\ddagger}R^{c\ddagger}$, —$NR^{c\ddagger}COR^{b\ddagger}$, —$SOR^{a\ddagger}$, —$SO_2R^{a\ddagger}$, —$SO_2NR^{b\ddagger}R^{c\ddagger}$, and —$NR^{c\ddagger}SO_2R^{a\ddagger}$, where $R^{a\ddagger}$ is chosen from optionally substituted $C_1$-$C_6$ alkyl, optionally substituted aryl, and optionally substituted heteroaryl;

$R^{b\ddagger}$ is chosen from H, optionally substituted $C_1$-$C_6$ alkyl, optionally substituted aryl, and optionally substituted heteroaryl; and $R^{c\ddagger}$ is chosen from hydrogen and optionally substituted $C_1$-$C_4$ alkyl; or $R^{b\ddagger}$ and $R^{c\ddagger}$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl); and wherein optionally substituted acyl, aminocarbonyl, alkoxycarbonyl, sulfinyl and sulfonyl are as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

As used herein, "modulation" refers to a change in kinase activity as a direct or indirect response to the presence of compounds described herein, relative to the activity of the kinase in the absence of the compound. The change may be an increase in activity or a decrease in activity, and may be due to the direct interaction of the compound with the kinase, or due to the interaction of the compound with one or more other factors that in turn affect kinase activity. For example, the presence of the compound may, for example, increase or decrease kinase activity by directly binding to the kinase, by causing (directly or indirectly) another factor to increase or decrease the kinase activity, or by (directly or indirectly) increasing or decreasing the amount of kinase present in the cell or organism.

Compounds of Formula I include, but are not limited to, optical isomers of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E- forms (or cis- and trans- forms) of compounds with carbon-carbon double bonds. Where compounds exist in various tautomeric forms, chemical entities of the present invention include all tautomeric forms of the compound. Compounds also include crystal forms including polymorphs and clathrates.

The present invention includes, but is not limited to, compounds of Formula I and all pharmaceutically acceptable forms thereof. Pharmaceutically acceptable forms of the compounds recited herein include pharmaceutically acceptable salts, solvates, chelates, non-covalent complexes, prodrugs, and mixtures thereof. In certain embodiments, the compounds described herein are in the form of pharmaceutically acceptable salts. Hence, the terms "compound" and "compounds" also encompass pharmaceutically acceptable salts, solvates, chelates, non-covalent complexes, prodrugs, and mixtures. The terms "compound" and "chemical entity" are used interchangeably herein.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COON$ where n is 0-4, and like salts. Similarly, pharmaceutically acceptable cations include, but are not limited to sodium, potassium, calcium, aluminum, lithium, and ammonium.

In addition, if the compound is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of the present invention, for example ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I.

The term "solvate" refers to the chemical entity formed by the interaction of a solvent and a compound. Suitable solvates are pharmaceutically acceptable solvates, such as hydrates, including monohydrates and hemi-hydrates.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

The term "active agent" is used to indicate a chemical entity which has biological activity. In certain embodiments, an "active agent" is a compound having pharmaceutical utility. For example an active agent may be an anti-cancer therapeutic.

The term "therapeutically effective amount" of a compound of this invention means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of Btk activity. In some embodiments, a therapeutically effective amount is an amount sufficient to reduce cancer symptoms, the symptoms of bone disorders, the symptoms of an allergic disorder, the symptoms of an autoimmune and/or inflammatory disease, or the symptoms of an acute inflammatory reaction. In some embodiments a therapeutically effective amount is an amount sufficient to decrease the number of detectable cancerous cells in an organism, detectably slow, or stop the growth of a cancerous tumor. In some embodiments, a therapeutically effective amount is an amount sufficient to shrink a cancerous tumor. In certain circumstances a patient suffering from cancer may not present symptoms of being affected. In some embodiments, a therapeutically effective amount of a compound/chemical entity is an amount sufficient to prevent a significant increase or significantly reduce the detectable level of cancerous cells or cancer markers in the patient's blood, serum, or tissues. In methods described herein for treating allergic disorders and/or autoimmune and/or inflammatory diseases and/or acute inflammatory reactions, a therapeutically effective amount may also be an amount sufficient, when administered to a patient, to detectably slow progression of the disease, or prevent the patient to whom the compound/chemical entity is given from presenting symptoms of the allergic disorders and/or autoimmune and/or inflammatory disease, and/or acute inflammatory response. In certain methods described herein for treating allergic disorders and/or autoimmune and/or inflammatory diseases and/or acute inflammatory reactions, a therapeutically effective amount may also be an amount sufficient to produce a detectable decrease in the amount of a marker protein or cell type in the patient's blood or serum. For example, in some embodiments a therapeutically effective amount is an amount of a compound/chemical entity described herein sufficient to significantly decrease the activity of B-cells. In another example, in some embodiments a therapeutically effective amount is an amount of a compound of Formula I sufficient to significantly decrease the number of B-cells. In another example, in some embodiments a therapeutically effective amount is an amount of a compound of Formula I sufficient to decrease the level of anti-acetylcholine receptor antibody in a patient's blood with the disease myasthenia gravis.

The term "inhibition" indicates a significant decrease in the baseline activity of a biological activity or process. "Inhibition of Btk activity" refers to a decrease in Btk activity as a direct or indirect response to the presence of a compound of Formula I, relative to the activity of Btk in the absence of such compound. The decrease in activity may be due to the direct interaction of the compound with Btk, or due to the interaction of such compound with one or more other factors that in turn affect Btk activity. For example, the presence of the compound may decrease Btk activity by directly binding to the Btk, by causing (directly or indirectly) another factor to decrease Btk activity, or by (directly or indirectly) decreasing the amount of Btk present in the cell or organism.

Inhibition of Btk activity also refers to observable inhibition of Btk activity in a standard biochemical assay for Btk activity, such as the ATP hydrolysis assay described below. In some embodiments, a compound of Formula I has an $IC_{50}$ value less than or equal to 1 micromolar. In some embodiments, a compound of Formula I has an $IC_{50}$ value less than or equal to less than 25 nanomolar. In some embodiments, a compound of Formula I has an $IC_{50}$ value less than or equal to 5 nanomolar.

"Inhibition of B-cell activity" refers to a decrease in B-cell activity as a direct or indirect response to the presence of a compound of Formula I, relative to the activity of B-cells in the absence of such compound. The decrease in activity may be due to the direct interaction of the compound with Btk or with one or more other factors that in turn affect B-cell activity.

Inhibition of B-cell activity also refers to observable inhibition of CD86 expression in a standard assay such as the assay described below. In some embodiments, a compound of Formula I has an $IC_{50}$ value less than or equal to 10 micromolar. In some embodiments, a compound of Formula I has an $IC_{50}$ value less than or equal to less than 0.5 micromolar. In some embodiments, a compound of Formula I has an $IC_{50}$ value less than or equal to 100 nanomolar.

"B cell activity" also includes activation, redistribution, reorganization, or capping of one or more various B cell membrane receptors, e.g., CD40, CD86, and Toll-like receptors TLRs (in particular TLR4), or membrane-bound immunoglobulins, e.g, IgM, IgG, and IgD. Most B cells also have membrane receptors for Fc portion of IgG in the form of either antigen-antibody complexes or aggregated IgG. B cells also carry membrane receptors for the activated components of complement, e.g., C3b, C3d, C4, and Clq. These various membrane receptors and membrane-bound immunoglobulins have membrane mobility and can undergo redistribution and capping that can initiate signal transduction.

B cell activity also includes the synthesis or production of antibodies or immunoglobulins. Immunoglobulins are synthesized by the B cell series and have common structural features and structural units. Five immunoglobulin classes, i.e., IgG, IgA, IgM, IgD, and IgE, are recognized on the basis of structural differences of their heavy chains including the amino acid sequence and length of the polypeptide chain. Antibodies to a given antigen may be detected in all or several classes of immunoglobulins or may be restricted to a single class or subclass of immunoglobulin. Autoantibodies or autoimmune antibodies may likewise belong to one or several classes of immunoglobulins. For example, rheumatoid factors (antibodies to IgG) are most often recognized as an IgM immunoglobulin, but can also consist of IgG or IgA.

In addition, B cell activity also is intended to include a series of events leading to B cell clonal expansion (proliferation) from precursor B lymphocytes and differentiation into antibody-synthesizing plasma cells which takes place in conjunction with antigen-binding and with cytokine signals from other cells.

"Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates no increase or any significant decrease in the number of B-cells, either in vitro or in vivo. Thus an inhibition of B-cell proliferation in vitro would be any significant decrease in the number of B-cells in an in vitro sample contacted with a compound of Formula I as compared to a matched sample not contacted with such compound.

Inhibition of B-cell proliferation also refers to observable inhibition of B-cell proliferation in a standard thymidine incorporation assay for B-cell proliferation, such as the assay described herein. In some embodiments, a compound of Formula I has an $IC_{50}$ value less than or equal to 10 micromolar. In some embodiments, a compound of Formula I has an $IC_{50}$ value less than or equal to less than 500 nanomolar. In some embodiments, a compound of Formula I has an $IC_{50}$ value less than or equal to 50 nanomolar.

An "allergy" or "allergic disorder" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma" refers to a disorder of the respiratory system characterized by inflammation, narrowing of the airways and increased reactivity of the airways to inhaled agents. Asthma is frequently, although not exclusively associated with atopic or allergic symptoms.

By "significant" is meant any detectable change that is statistically significant in a standard parametric test of statistical significance such as Student's T-test, where $p<0.05$.

A "disease responsive to inhibition of Btk activity" is a disease in which inhibiting Btk kinase provides a therapeutic benefit such as an amelioration of symptoms, decrease in disease progression, prevention or delay of disease onset, or inhibition of aberrant activity of certain cell-types (monocytes, osteoclasts, B-cells, mast cells, myeloid cells, basophils, macrophages, neutrophils, and dendritic cells).

"Treatment or treating means any treatment of a disease in a patient, including:
 a) preventing the disease, that is, causing the clinical symptoms of the disease not to develop;
 b) inhibiting the disease;
 c) slowing or arresting the development of clinical symptoms; and/or
 d) relieving the disease, that is, causing the regression of clinical symptoms.

"Patient" refers to an animal, such as a mammal, that has been or will be the object of treatment, observation or experiment. The methods of the invention can be useful in both human therapy and veterinary applications. In some embodiments, the patient is a mammal; in some embodiments the patient is human; and in some embodiments the patient is chosen from cats and dogs.

Provided is a compound of Formula I:

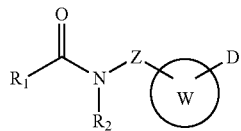

(Formula I)

and pharmaceutically acceptable salts, solvates, chelates, non-covalent complexes, prodrugs, and mixtures thereof, wherein R₁ is chosen from:

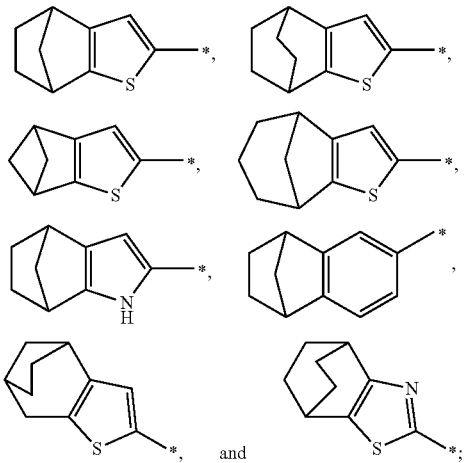

R₂ is H or CH₃;

Z is chosen from phenylene and pyridylidene wherein is optionally substituted with one or more groups independently chosen from CN, halo, hydroxyl, optionally substituted lower alkyl, and optionally substituted lower alkoxy;

is chosen from

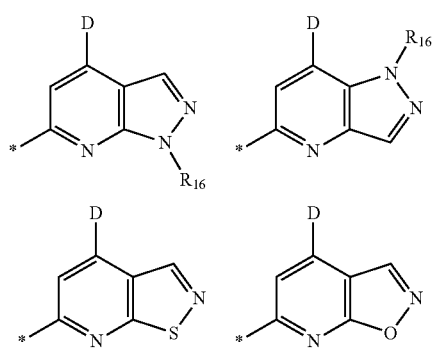

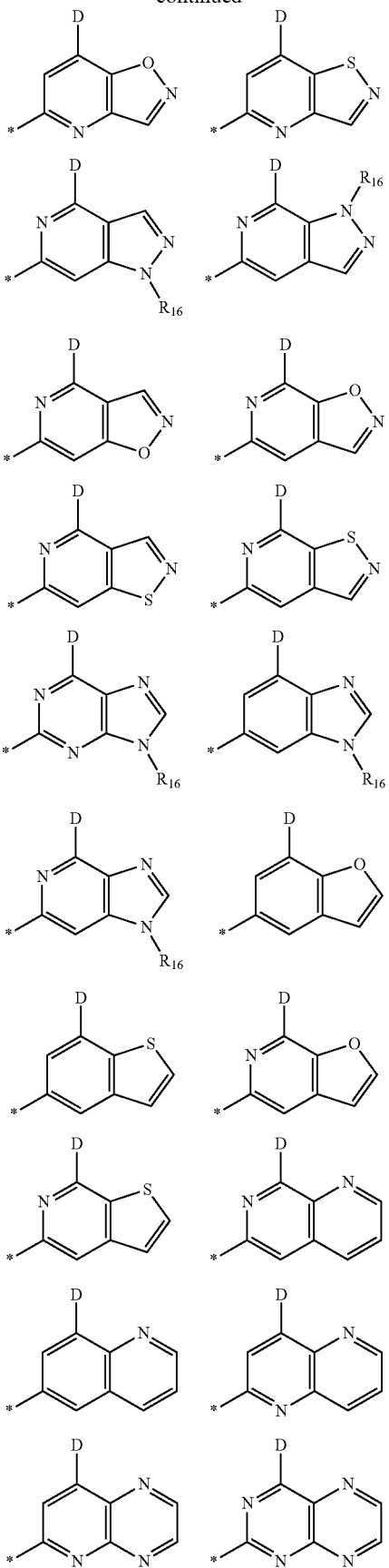

-continued

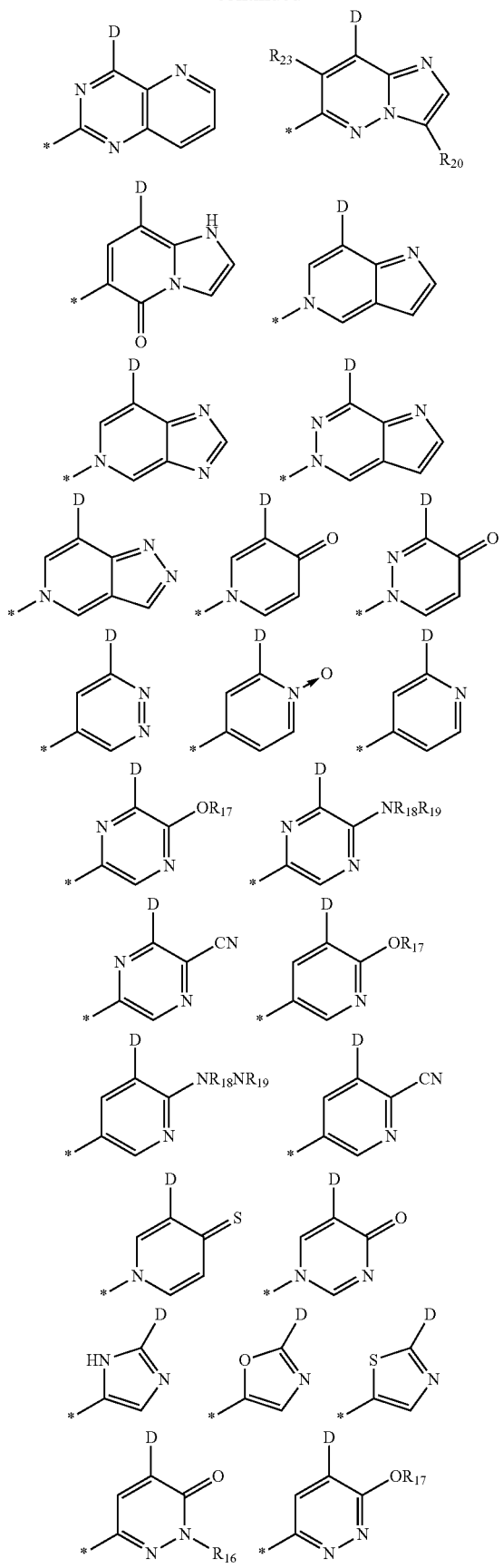
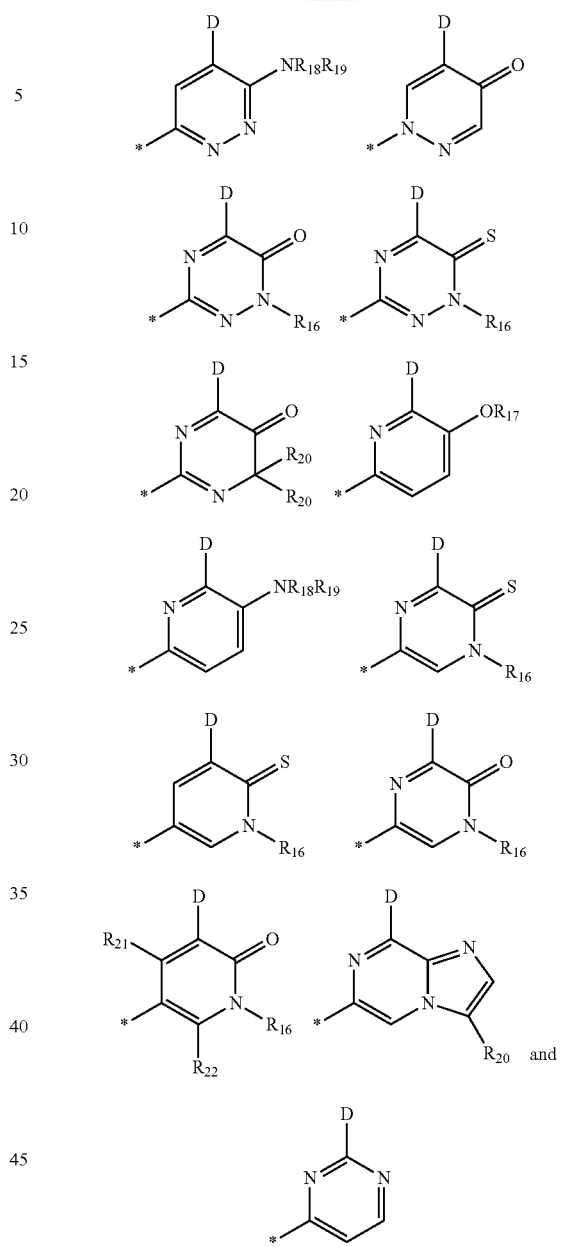

each of which is optionally substituted with one or two groups chosen from hydroxy, cyano, halo, optionally substituted lower alkyl, and optionally substituted lower alkoxy;

each $R_{16}$ is independently chosen from hydrogen, cyano, optionally substituted cycloalkyl, and optionally substituted lower alkyl;

$R_{17}$, $R_{18}$, $R_{19}$, $R_{21}$, $R_{22}$, and $R_{23}$ are independently chosen from hydrogen and optionally substituted lower alkyl;

each $R_{20}$ is independently chosen from hydrogen, hydroxy, cyano, halo, optionally substituted lower alkyl, and optionally substituted lower alkoxy;

D is —$NHR_7$; and $R_7$ is chosen from optionally substituted aryl and optionally substituted heteroaryl.

In certain embodiments, $R_1$ is chosen from:

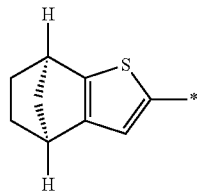 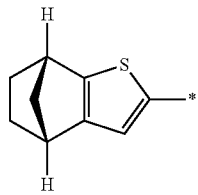

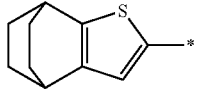 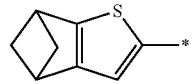

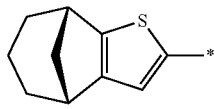 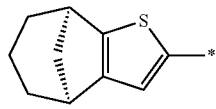

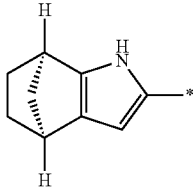 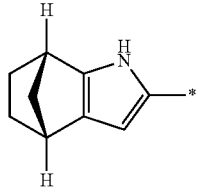

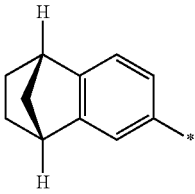 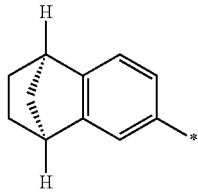

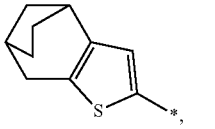, and 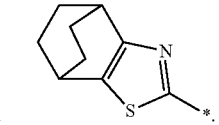.

In certain embodiments, $R_1$ is chosen from:

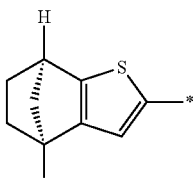 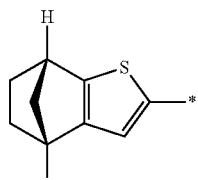

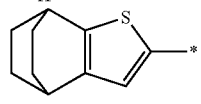 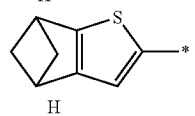

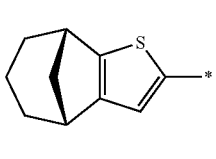 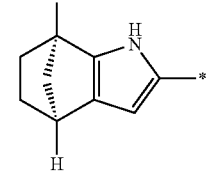

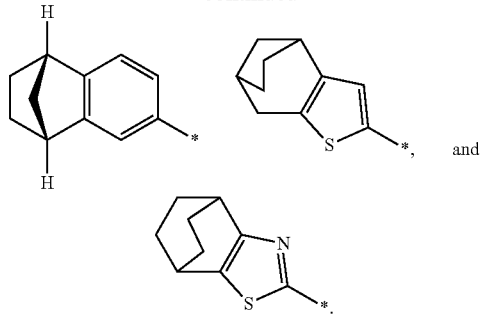, and

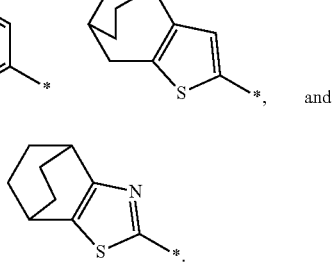.

In certain embodiments, $R_1$ is chosen from:

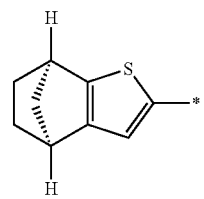 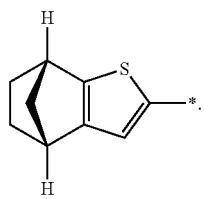.

In certain embodiments, $R_2$ is H. In certain embodiments, $R_2$ is $CH_3$.

In certain embodiments, Z is chosen from phenylene and pyridylidene wherein is optionally substituted with one or more groups independently chosen from $CH_3$, F, and Cl.

In certain embodiments, D is —N(H)-B-L-G wherein

B is chosen from optionally substituted phenylene, optionally substituted pyridylidene, optionally substituted pyrazolyl, optionally substituted 2-oxo-1,2-dihydropyridinyl,

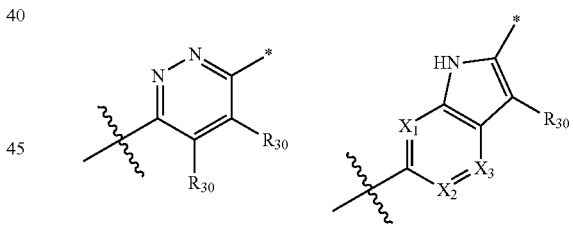

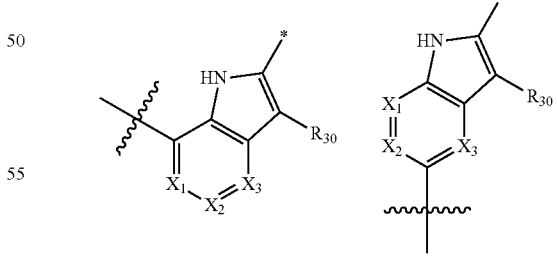

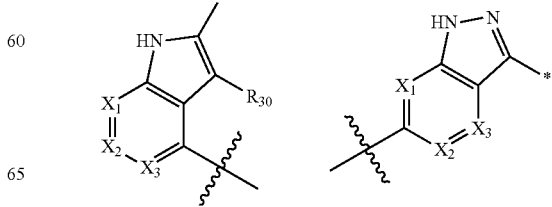

-continued

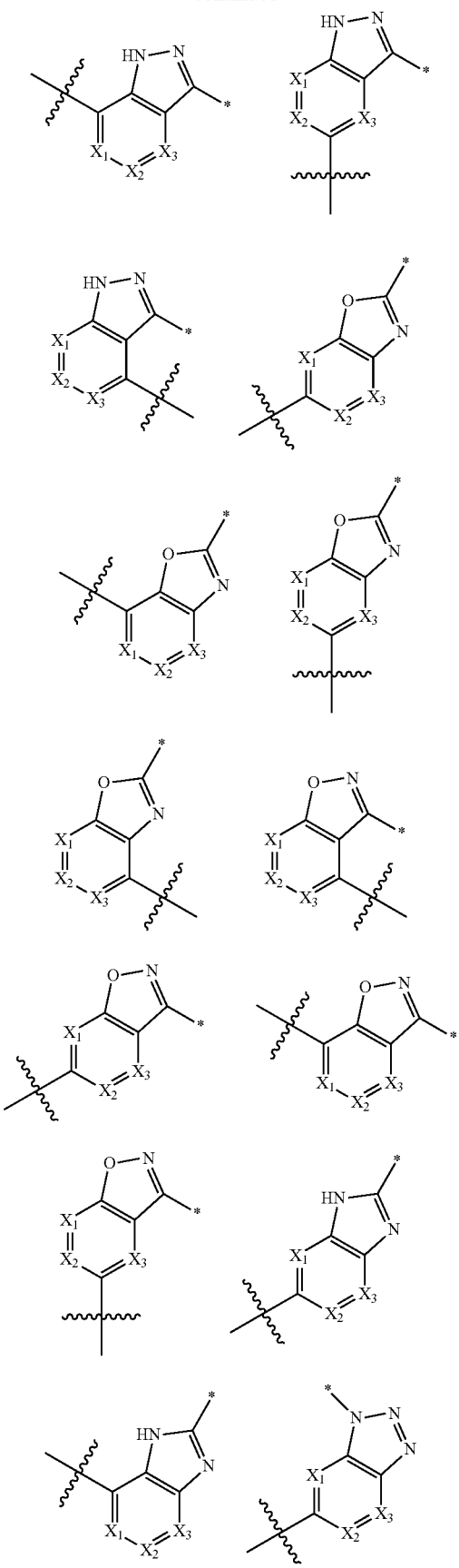

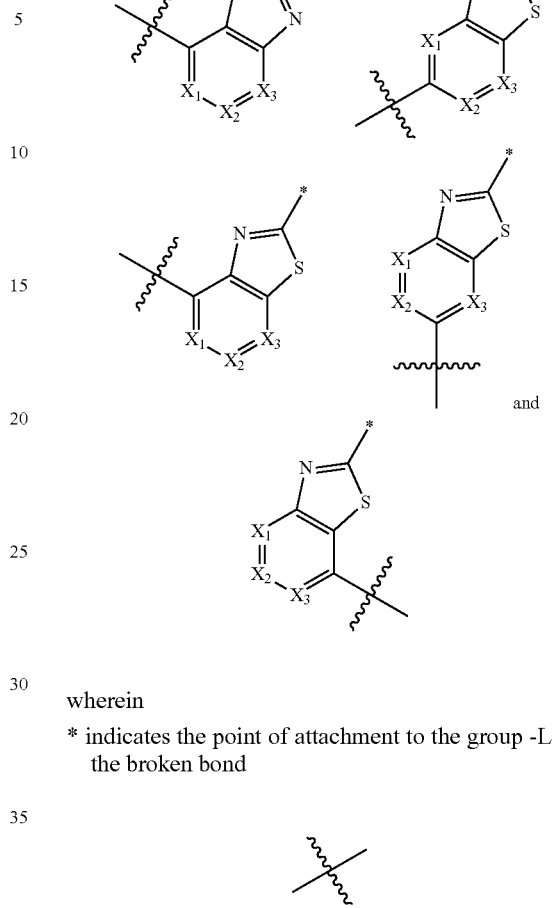

wherein
* indicates the point of attachment to the group -L-G and the broken bond indicates the point of attachment to the —N(H)— group;
each $X_1$ is independently chosen from N and $CR_{31}$;
each $X_2$ is independently chosen from N and $CR_{31}$; and
each $X_3$ is independently chosen from N and $CR_{31}$; and wherein no more than one of $X_1$, $X_2$, and $X_3$ is N,
each $R_{30}$ is independently chosen from hydrogen, hydroxy, cyano, halo, optionally substituted lower alkyl, and optionally substituted lower alkoxy;
each $R_{31}$ is independently chosen from hydrogen, hydroxy, cyano, halo, optionally substituted lower alkyl, and optionally substituted lower alkoxy;
L is chosen from optionally substituted $C_0$-$C_4$alkylene, —O-optionally substituted $C_0$-$C_4$alkylene, —($C_0$-$C_4$alkylene)(SO)—, —($C_0$-$C_4$alkylene)(SO$_2$)—; and —($C_0$-$C_4$alkylene)(C=O)—; and
G is chosen from hydrogen, halo, hydroxy, alkoxy, nitro, optionally substituted alkyl, optionally substituted amino, optionally substituted carbamimidoyl, optionally substituted heterocycloalkyl, optionally substituted cycloalkyl, optionally substituted aryl, and optionally substituted heteroaryl.

In certain embodiments, B is chosen from ortho-phenylene, meta-phenylene, para-phenylene, ortho-pyridylidene, meta-pyridylidene, para-pyridylidene, pyrazol-4-yl,

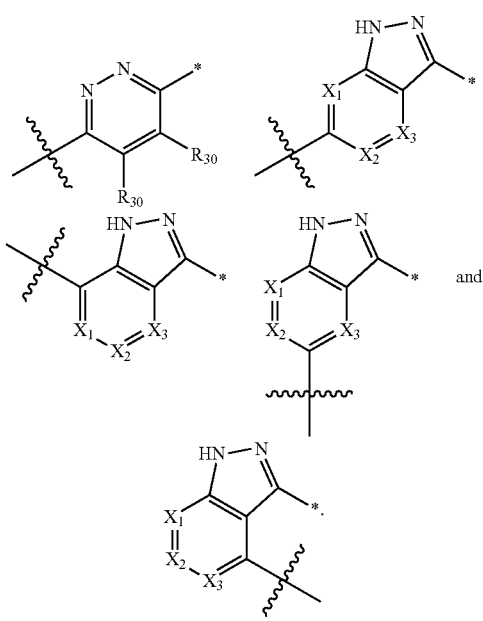

In certain embodiments, B is chosen from para-phenylene and meta-phenylene. In certain embodiments, B is para-phenylene.

In certain embodiments, B is para-pyridylidene. In certain embodiments, B is pyrazol-4-yl.

In certain embodiments, B is chosen from

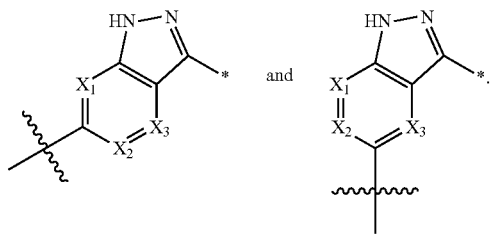

In certain embodiments, B is

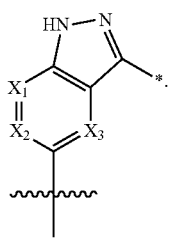

In certain embodiments, B is

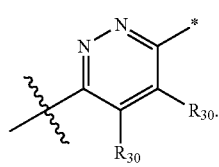

In certain embodiments, $X_1$, $X_2$ and $X_3$ are independently $CR_{31}$. In certain embodiments, $X_1$, $X_2$ and $X_3$ are independently $CR_{31}$ and each $R_{31}$ is hydrogen.

In certain embodiments, each $R_{30}$ is hydrogen.

In certain embodiments, L is chosen from optionally substituted $C_0$-$C_4$alkylene, —O-optionally substituted $C_0$-$C_4$alkylene, —($C_0$-$C_4$alkylene)($SO_2$)—; and —($C_0$-$C_4$alkylene)(C=O)—. In certain embodiments, L is chosen from a covalent bond, —(C=O)—, —$CH_2$—, —$CH_2$(C=O)—, —$SO_2$— and —$CH(CH_3)$(C=O)—. In some embodiments, L is chosen from —(C=O)—, —$CH_2$—, —$CH_2$(C=O)—, —$SO_2$— and —$CH(CH_3)$(C=O)—. In some embodiments, L is —(C=O)—. In some embodiments, L is —$CH_2$—. In some embodiments, L is a covalent bond.

In certain embodiments, G is chosen from hydrogen, hydroxy, $C_1$-$C_6$alkoxy, optionally substituted amino, optionally substituted $C_3$-$C_7$heterocycloalkyl, optionally substituted $C_3$-$C_7$cycloalkyl, optionally substituted aryl, and optionally substituted heteroaryl.

In certain embodiments, G is chosen from hydrogen, hydroxy,

—$NR_8R_9$ wherein $R_8$ and $R_9$ are independently chosen from hydrogen, optionally substituted acyl, and optionally substituted ($C_1$-$C_6$)alkyl; or wherein $R_8$ and $R_9$, together with the nitrogen to which they are bound, form an optionally substituted 5- to 7-membered nitrogen containing heterocycloalkyl which optionally further includes one or two additional heteroatoms chosen from N, O, and S;

optionally substituted 5,6-dihydro-8H-imidazo[1,2-a]pyrazin-7-yl, lower alkoxy, and 1H-tetrazol-5-yl.

In certain embodiments, G is chosen from hydrogen, hydroxy,

N-methylethanolamino,

—N($C_1$-$C_6$ alkyl)$_2$, optionally substituted morpholin-4-yl, optionally substituted piperazin-1-yl, optionally substituted piperazin-2-yl, optionally substituted homopiperazin-1-yl, and optionally substituted cyclopropyl.

In certain embodiments, G is chosen from hydrogen,

—N($C_1$-$C_6$ alkyl)$_2$, morpholin-4-yl, 4-acyl-piperazin-1-yl, 4-lower alkyl-piperazin-1-yl, 3-oxo-piperazin-1-yl, 3-oxopiperazin-2-yl, homopiperazin-1-yl, 4-lower alkyl-homopiperazin-1-yl, and cyclopropyl.

In certain embodiments, L is a covalent bond and G is hydrogen.

Also provided is a compound of Formula II:

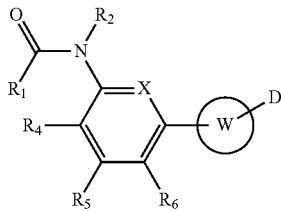

(Formula II)

and pharmaceutically acceptable salts, solvates, chelates, non-covalent complexes, prodrugs, and mixtures thereof, wherein
X is $CR_3$ or N;
$R_3$ is chosen from H, $CH_3$, F and Cl;
$R_4$ is chosen from H, $CH_3$, F and Cl;
$R_5$ is chosen from H, $CH_3$, F and Cl;
$R_6$ is chosen from H, $CH_3$, F and Cl; and

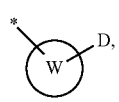

$R_1$, and $R_2$ are as described above.
In certain embodiments, $R_3$ is chosen from $CH_3$, F and Cl.
In certain embodiments, $R_4$ is H. In certain embodiments, $R_4$ is $CH_3$ or F.
In certain embodiments, $R_5$ is H. In certain embodiments, $R_5$ is F or Cl.
In certain embodiments, $R_6$ is H. In certain embodiments, $R_6$ is F.
Also provided is a compound of Formula III:

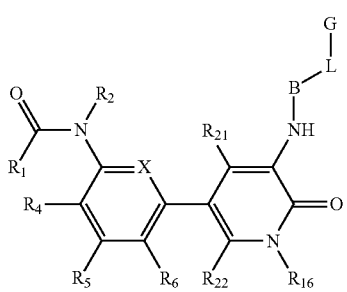

(Formula III)

and pharmaceutically acceptable salts, solvates, chelates, non-covalent complexes, prodrugs, and mixtures thereof, wherein $R_1$, $R_2$, X, $R_4$, $R_5$, $R_6$, $R_{16}$, $R_{21}$, $R_{22}$, B, L and G are as defined above. In certain embodiments, $R_{21}$ is H. In certain embodiments, $R_{22}$ is H. In certain embodiments, $R_{16}$ is H. In certain embodiments, $R_{16}$ is $CH_3$.

Also provided is a compound of Formula V:

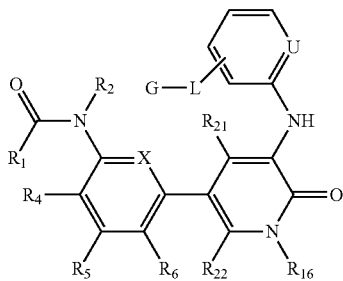

(Formula V)

and pharmaceutically acceptable salts, solvates, chelates, non-covalent complexes, prodrugs, and mixtures thereof, wherein U is N or CH; and $R_1$, $R_2$, X, $R_4$, $R_5$, $R_6$, $R_{16}$, $R_{21}$, $R_{22}$, L and G are as defined above.

Also provided is a compound of Formula IV:

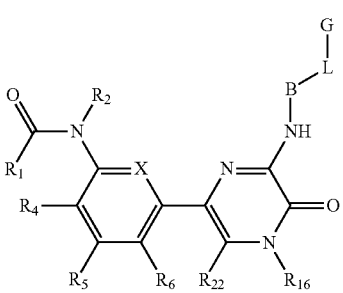

(Formula IV)

and pharmaceutically acceptable salts, solvates, chelates, non-covalent complexes, prodrugs, and mixtures thereof, wherein $R_1$, $R_2$, X, $R_4$, $R_5$, $R_6$, $R_{16}$, $R_{22}$, B, L and G are as defined above. In certain embodiments, $R_{22}$ is H. In certain embodiments, $R_{16}$ is H. In certain embodiments, $R_{16}$ is $CH_3$.

Also provided is a compound of Formula VI:

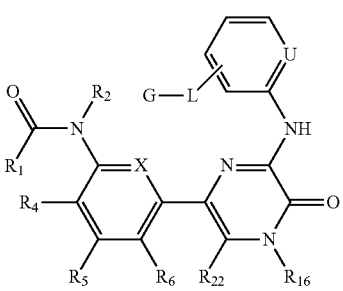

(Formula VI)

and pharmaceutically acceptable salts, solvates, chelates, non-covalent complexes, prodrugs, and mixtures thereof, wherein U is N or CH; and $R_1$, $R_2$, X, $R_4$, $R_5$, $R_6$, $R_{16}$, $R_{22}$, L and G are as defined above.

In certain embodiments, the compound of Formula I is chosen from
N-{3-[6-({4-[(2S)-1,4-dimethyl-3-oxopiperazin-2-yl]phenyl}amino)-4-methyl-5-oxo-4,5-dihydropyrazin-2-yl]-2-methylphenyl}-(4S,7R)-4,7-methano-4,5,6,7-tetrahydro-1-benzothiophene-2-carboxamide;

N-{3-[6-({4-[(2R)-1,4-dimethyl-3-oxopiperazin-2-yl]phenyl}amino)-4-methyl-5-oxo-4,5-dihydropyrazin-2-yl]-2-methylphenyl}-(4S,7R)-4,7-methano-4,5,6,7-tetrahydro-1-benzothiophene-2-carboxamide;

N-{3-[6-({4-[(2S)-1,4-dimethyl-3-oxopiperazin-2-yl]phenyl}amino)-4-methyl-5-oxo-4,5-dihydropyrazin-2-yl]-2-methylphenyl}-(4R,7S)-4,7-methano-4,5,6,7-tetrahydro-1-benzothiophene-2-carboxamide;

N-{3-[6-({4-[(2R)-1,4-dimethyl-3-oxopiperazin-2-yl]phenyl}amino)-4-methyl-5-oxo-4,5-dihydropyrazin-2-yl]-2-methylphenyl}-(4R,7S)-4,7-methano-4,5,6,7-tetrahydro-1-benzothiophene-2-carboxamide;

N-[3-(5-{[5-(4-ethylpiperazin-1-yl)pyridin-2-yl]amino}-1-methyl-6-oxo-1,6-dihydropyridin-3-yl)-2,4-difluorophenyl]-4,7-methano-4,5,6,7-tetrahydro-1-benzothiophene-2-carboxamide;

N-(3-fluoro-6-(1-methyl-5-(5-(4-methylpiperazin-1-yl)pyridin-2-ylamino)-6-oxo-1,6-dihydropyridin-3-yl)pyridin-2-yl)-4,7-methano-4,5,6,7-tetrahydrobenzo[b]thiophene-2-carboxamide;

(4S,7R)—N-[3-fluoro-6-(1-methyl-5-{[5-(4-methylpiperazin-1-yl)pyridin-2-yl]amino}-6-oxo-1,6-dihydropyridin-3-yl)pyridin-2-yl]-4,7-methano-4,5,6,7-tetrahydrobenzo[b]thiophene-2-carboxamide (+) isomer;

(4R,7S)—N-[3-fluoro-6-(1-methyl-5-{[5-(4-methylpiperazin-1-yl)pyridin-2-yl]amino}-6-oxo-1,6-dihydropyridin-3-yl)pyridin-2-yl]-4,7-methano-4,5,6,7-tetrahydrobenzo[b]thiophene-2-carboxamide (−) isomer;

N-(5-(6-(4-(4-(dimethylamino)piperidin-1-yl)phenylamino)-4-methyl-5-oxo-4,5-dihydropyrazin-2-yl)-2-fluorophenyl)-4,7-methano-4,5,6,7-tetrahydrobenzo[b]thiophene-2-carboxamide;

N-(2-fluoro-5-(4-methyl-6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide;

N-(2,4-difluoro-5-(4-methyl-6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide;

N-(2-methyl-4-fluoro-5-(4-methyl-6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide;

N-(2-chloro-4-methyl-5-(4-methyl-6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide;

N-(5-fluoro-6-(4-methyl-6-(4-(4-methylpiperazin-1-yl)phenylamino)-5-oxo-4,5-dihydropyrazin-2-yl)pyridin-2-yl)-4,7-methano-4,5,6,7-tetrahydrobenzo[b]thiophene-2-carboxamide;

N-(4-fluoro-2-methyl-3-(6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide;

N-(3-fluoro-6-(4-methyl-6-(4-(4-methylpiperazin-1-yl)phenylamino)-5-oxo-4,5-dihydropyrazin-2-yl)pyridin-2-yl)-4,7-methano-4,5,6,7-tetrahydrobenzo[b]thiophene-2-carboxamide;

N-(2-fluoro-5-(1-methyl-5-(5-(4-methylpiperazin-1-yl)pyridin-2-ylamino)-6-oxo-1,6-dihydropyridin-3-yl)phenyl)-4,7-methano-4,5,6,7-tetrahydrobenzo[b]thiophene-2-carboxamide;

(4R,7S)—N-[2-fluoro-5-(1-methyl-5-{[5-(4-methylpiperazin-1-yl)pyridin-2-yl]amino}-6-oxo-1,6-dihydropyridin-3-yl)phenyl]-4,7-methano-4,5,6,7-tetrahydrobenzo[b]thiophene-2-carboxamide (−) isomer;

(4S,7R)—N-[2-fluoro-5-(1-methyl-5-{[5-(4-methylpiperazin-1-yl)pyridin-2-yl]amino}-6-oxo-1,6-dihydropyridin-3-yl)phenyl]-4,7-methano-4,5,6,7-tetrahydrobenzo[b]thiophene-2-carboxamide (+) isomer;

N-(2,6-difluoro-3-(1-methyl-5-(5-(4-methylpiperazin-1-yl)pyridin-2-ylamino)-6-oxo-1,6-dihydropyridin-3-yl)phenyl)-4,7-methano-4,5,6,7-tetrahydrobenzo[b]thiophene-2-carboxamide;

N-(6-fluoro-2-methyl-3-(1-methyl-5-(5-(4-methylpiperazin-1-yl)pyridin-2-ylamino)-6-oxo-1,6-dihydropyridin-3-yl)phenyl)-4,7-methano-4,5,6,7-tetrahydrobenzo[b]thiophene-2-carboxamide;

N-(2-chloro-6-methyl-3-(1-methyl-5-(5-(4-methylpiperazin-1-yl)pyridin-2-ylamino)-6-oxo-1,6-dihydropyridin-3-yl)phenyl)-4,7-methano-4,5,6,7-tetrahydrobenzo[b]thiophene-2-carboxamide;

N-(5-fluoro-6-(1-methyl-5-(5-(4-methylpiperazin-1-yl)pyridin-2-ylamino)-6-oxo-1,6-dihydropyridin-3-yl)pyridin-2-yl)-4,7-methano-4,5,6,7-tetrahydrobenzo[b]thiophene-2-carboxamide;

N-(6-fluoro-2-methyl-3-(5-(5-(4-methylpiperazin-1-yl)pyridin-2-ylamino)-6-oxo-1,6-dihydropyridin-3-yl)phenyl)-4,7-methano-4,5,6,7-tetrahydrobenzo[b]thiophene-2-carboxamide;

N-(5-(6-(1-ethyl-1H-pyrazol-4-ylamino)-4-methyl-5-oxo-4,5-dihydropyrazin-2-yl)-2-fluorophenyl)-4,7-methano-4,5,6,7-tetrahydrobenzo[b]thiophene-2-carboxamide;

N-(3-(6-(1-ethyl-1H-pyrazol-4-ylamino)-4-methyl-5-oxo-4,5-dihydropyrazin-2-yl)-2,6-difluorophenyl)-4,7-methano-4,5,6,7-tetrahydrobenzo[b]thiophene-2-carboxamide;

N-(3-(6-(1-ethyl-1H-pyrazol-4-ylamino)-4-methyl-5-oxo-4,5-dihydropyrazin-2-yl)-6-fluoro-2-methylphenyl)-4,7-methano-4,5,6,7-tetrahydrobenzo[b]thiophene-2-carboxamide;

N-(2-chloro-3-(6-(1-ethyl-1H-pyrazol-4-ylamino)-4-methyl-5-oxo-4,5-dihydropyrazin-2-yl)-6-methylphenyl)-4,7-methano-4,5,6,7-tetrahydrobenzo[b]thiophene-2-carboxamide;

N-(6-(6-(1-ethyl-1H-pyrazol-4-ylamino)-4-methyl-5-oxo-4,5-dihydropyrazin-2-yl)-3-fluoropyridin-2-yl)-4,7-methano-4,5,6,7-tetrahydrobenzo[b]thiophene-2-carboxamide;

N-(6-(6-(1-ethyl-1H-pyrazol-4-ylamino)-4-methyl-5-oxo-4,5-dihydropyrazin-2-yl)-5-fluoropyridin-2-yl)-4,7-methano-4,5,6,7-tetrahydrobenzo[b]thiophene-2-carboxamide;

N-(5-(6-(1H-pyrazol-4-ylamino)-4-methyl-5-oxo-4,5-dihydropyrazin-2-yl)-2-fluorophenyl)-4,7-methano-4,5,6,7-tetrahydrobenzo[b]thiophene-2-carboxamide;

N-(3-(6-(1H-pyrazol-4-ylamino)-4-methyl-5-oxo-4,5-dihydropyrazin-2-yl)-2,6-difluorophenyl)-4,7-methano-4,5,6,7-tetrahydrobenzo[b]thiophene-2-carboxamide;

N-(3-(6-(1H-pyrazol-4-ylamino)-4-methyl-5-oxo-4,5-dihydropyrazin-2-yl)-6-fluoro-2-methylphenyl)-4,7-methano-4,5,6,7-tetrahydrobenzo[b]thiophene-2-carboxamide;

N-(3-(6-(1H-pyrazol-4-ylamino)-4-methyl-5-oxo-4,5-dihydropyrazin-2-yl)-2-chloro-6-methylphenyl)-4,7-methano-4,5,6,7-tetrahydrobenzo[b]thiophene-2-carboxamide;

N-(6-(6-(1H-pyrazol-4-ylamino)-4-methyl-5-oxo-4,5-dihydropyrazin-2-yl)-3-fluoropyridin-2-yl)-4,7-methano-4,5,6,7-tetrahydrobenzo[b]thiophene-2-carboxamide;

N-(6-(6-(1H-pyrazol-4-ylamino)-4-methyl-5-oxo-4,5-dihydropyrazin-2-yl)-5-fluoropyridin-2-yl)-4,7-methano-4,5,6,7-tetrahydrobenzo[b]thiophene-2-carboxamide;

N-(2-fluoro-5-(4-methyl-6-(4-(1-methylpiperidin-4-yl)phenylamino)-5-oxo-4,5-dihydropyrazin-2-yl)phenyl)-4,7-methano-4,5,6,7-tetrahydrobenzo[b]thiophene-2-carboxamide;

N-(2-fluoro-5-(1-methyl-5-(6-(1-methylpiperidin-4-yl)pyridazin-3-ylamino)-6-oxo-1,6-dihydropyridin-3-yl)phenyl)-4,7-methano-4,5,6,7-tetrahydrobenzo[b]thiophene-2-carboxamide;

N-(2,6-difluoro-3-(1-methyl-5-(6-(1-methylpiperidin-4-yl)pyridazin-3-ylamino)-6-oxo-1,6-dihydropyridin-3-yl)phenyl)-4,7-methano-4,5,6,7-tetrahydrobenzo[b]thiophene-2-carboxamide;

N-(6-fluoro-2-methyl-3-(1-methyl-5-(6-(1-methylpiperidin-4-yl)pyridazin-3-ylamino)-6-oxo-1,6-dihydropyridin-3-yl)phenyl)-4,7-methano-4,5,6,7-tetrahydrobenzo[b]thiophene-2-carboxamide;

N-(2-chloro-6-methyl-3-(1-methyl-5-(6-(1-methylpiperidin-4-yl)pyridazin-3-ylamino)-6-oxo-1,6-dihydropyridin-3-yl)phenyl)-4,7-methano-4,5,6,7-tetrahydrobenzo[b]thiophene-2-carboxamide;

N-(3-fluoro-6-(1-methyl-5-(6-(1-methylpiperidin-4-yl)pyridazin-3-ylamino)-6-oxo-1,6-dihydropyridin-3-yl)pyridin-2-yl)-4,7-methano-4,5,6,7-tetrahydrobenzo[b]thiophene-2-carboxamide;

N-(5-fluoro-6-(1-methyl-5-(6-(1-methylpiperidin-4-yl)pyridazin-3-ylamino)-6-oxo-1,6-dihydropyridin-3-yl)pyridin-2-yl)-4,7-methano-4,5,6,7-tetrahydrobenzo[b]thiophene-2-carboxamide;

N-(2-fluoro-5-(6-(4-((isopropyl(methyl)amino)methyl)phenylamino)-4-methyl-5-oxo-4,5-dihydropyrazin-2-yl)phenyl)-4,7-methano-4,5,6,7-tetrahydrobenzo[b]thiophene-2-carboxamide;

N-(2,6-difluoro-3-(6-(4-((isopropyl(methyl)amino)methyl)phenylamino)-4-methyl-5-oxo-4,5-dihydropyrazin-2-yl)phenyl)-4,7-methano-4,5,6,7-tetrahydrobenzo[b]thiophene-2-carboxamide;

N-(6-fluoro-3-(6-(4-((isopropyl(methyl)amino)methyl)phenylamino)-4-methyl-5-oxo-4,5-dihydropyrazin-2-yl)-2-methylphenyl)-4,7-methano-4,5,6,7-tetrahydrobenzo[b]thiophene-2-carboxamide;

N-(2-chloro-3-(6-(4-((isopropyl(methyl)amino)methyl)phenylamino)-4-methyl-5-oxo-4,5-dihydropyrazin-2-yl)-6-methylphenyl)-4,7-methano-4,5,6,7-tetrahydrobenzo[b]thiophene-2-carboxamide;

N-(3-fluoro-6-(6-(4-((isopropyl(methyl)amino)methyl)phenylamino)-4-methyl-5-oxo-4,5-dihydropyrazin-2-yl)pyridin-2-yl)-4,7-methano-4,5,6,7-tetrahydrobenzo[b]thiophene-2-carboxamide;

N-(5-fluoro-6-(6-(4-((isopropyl(methyl)amino)methyl)phenylamino)-4-methyl-5-oxo-4,5-dihydropyrazin-2-yl)pyridin-2-yl)-4,7-methano-4,5,6,7-tetrahydrobenzo[b]thiophene-2-carboxamide;

N-{2-methyl-3-[4-methyl-6-({4-[(4-methylpiperazin-1-yl)carbonyl]phenyl}amino)-5-oxo-4,5-dihydropyrazin-2-yl]phenyl}-4,7-methano-4,5,6,7-tetrahydro-1-benzothiophene-2-carboxamide;

3-fluoro-N-[2-methyl-3-(4-methyl-6-{[4-(morpholin-4-ylcarbonyl)phenyl]amino}-5-oxo-4,5-dihydropyrazin-2-yl)phenyl]-4,7-methano-4,5,6,7-tetrahydro-1-benzothiophene-2-carboxamide;

N-(3-{5-[(5-cyclopropyl-1H-pyrazol-3-yl)amino]-1-methyl-6-oxo-1,6-dihydropyridin-3-yl}-2-methylphenyl)-4,7-methano-4,5,6,7-tetrahydrobenzo[b]thiophene-2-carboxamide;

N-[2-methyl-3-(1-methyl-5-{[5-(morpholin-4-yl)pyridin-2-yl]amino}-6-oxo-1,6-dihydropyridin-3-yl)phenyl]-4,7-methano-4,5,6,7-tetrahydro-1-benzothiophene-2-carboxamide;

N-[3-(5-{[5-(4-hydroxy-4-methylpiperidin-1-yl)pyridin-2-yl]amino}-1-methyl-6-oxo-1,6-dihydropyridin-3-yl)-2-methylphenyl]-4,7-methano-4,5,6,7-tetrahydro-1-benzothiophene-2-carboxamide;

N-(3-(5-(5-((isopropyl(methyl)amino)methyl)pyridin-2-ylamino)-1-methyl-6-oxo-1,6-dihydropyridin-3-yl)-2-methylphenyl)-4,7-methano-4,5,6,7-tetrahydrobenzo[b]thiophene-2-carboxamide;

N-[2-methyl-3-(1-methyl-5-{[6-(morpholin-4-yl)pyridazin-3-yl]amino}-6-oxo-1,6-dihydropyridin-3-yl)phenyl]-4,7-methano-4,5,6,7-tetrahydro-1-benzothiophene-2-carboxamide;

N-{3-[5-({5-[4-(dimethylamino)piperidin-1-yl]pyridin-2-yl}amino)-1-methyl-6-oxo-1,6-dihydropyridin-3-yl]-2-methylphenyl}-4,7-methano-4,5,6,7-tetrahydro-1-benzothiophene-2-carboxamide;

N-[2-methyl-3-(1-methyl-5-{[6-(4-methylpiperazin-1-yl)pyridazin-3-yl]amino}-6-oxo-1,6-dihydropyridin-3-yl)phenyl]-4,7-methano-4,5,6,7-tetrahydro-1-benzothiophene-2-carboxamide;

N-[3-(5-{[5-(4-ethylpiperazin-1-yl)pyridin-2-yl]amino}-1-methyl-6-oxo-1,6-dihydropyridin-3-yl)-2-methylphenyl]-4,7-methano-4,5,6,7-tetrahydro-1-benzothiophene-2-carboxamide;

N-{2-methyl-3-[1-methyl-6-oxo-5-({5-[4-(propan-2-yl)piperazin-1-yl]pyridin-2-yl}amino)-1,6-dihydropyridin-3-yl]phenyl}-4,7-methano-4,5,6,7-tetrahydro-1-benzothiophene-2-carboxamide;

N-[2-methyl-3-(5-{[6-(4-methylpiperazin-1-yl)pyridazin-3-yl]amino}-6-oxo-1,6-dihydropyridin-3-yl)phenyl]-4,7-methano-4,5,6,7-tetrahydro-1-benzothiophene-2-carboxamide;

N-{2-methyl-3-[1-methyl-6-oxo-5-({6-[4-(propan-2-yl)piperazin-1-yl]pyridazin-3-yl}amino)-1,6-dihydropyridin-3-yl]phenyl}-4,7-methano-4,5,6,7-tetrahydro-1-benzothiophene-2-carboxamide;

N-[3-(5-{[6-(4-ethylpiperazin-1-yl)pyridazin-3-yl]amino}-1-methyl-6-oxo-1,6-dihydropyridin-3-yl)-2-methylphenyl]-4,7-methano-4,5,6,7-tetrahydro-1-benzothiophene-2-carboxamide;

N-(3-{6-[(4-{[(2-hydroxyethyl)(methyl)amino]methyl}phenyl)amino]-4-methyl-5-oxo-4,5-dihydropyrazin-2-yl}-2-methylphenyl)-4,7-methano-4,5,6,7-tetrahydro-1-benzothiophene-2-carboxamide;

N-[3-(5-{[6-(4-hydroxy-4-methylpiperidin-1-yl)pyridazin-3-yl]amino}-1-methyl-6-oxo-1,6-dihydropyridin-3-yl)-2-methylphenyl]-4,7-methano-4,5,6,7-tetrahydro-1-benzothiophene-2-carboxamide;

N-[2-methyl-3-(1-methyl-5-{[5-(4-methyl-1,4-diazepan-1-yl)pyridin-2-yl]amino}-6-oxo-1,6-dihydropyridin-3-yl)phenyl]-4,7-methano-4,5,6,7-tetrahydro-1-benzothiophene-2-carboxamide;

N-[2-methyl-3-(1-methyl-5-{[5-(1,4-oxazepan-4-yl)pyridin-2-yl]amino}-6-oxo-1,6-dihydropyridin-3-yl)phenyl]-4,7-methano-4,5,6,7-tetrahydro-1-benzothiophene-2-carboxamide;

N-{3-[6-(1H-indazol-5-ylamino)-4-methyl-5-oxo-4,5-dihydropyrazin-2-yl]-2-methylphenyl}-4,7-methano-4,5,6,7-tetrahydro-1-benzothiophene-2-carboxamide;

N-[3-(5-{[5-(4-ethylpiperazin-1-yl)pyridin-2-yl]amino}-1-methyl-6-oxo-1,6-dihydropyridazin-3-yl)-2-methylphenyl]-4,7-methano-4,5,6,7-tetrahydro-1-benzothiophene-2-carboxamide;

N-(2-fluoro-5-(8-(4-(4-methylpiperazin-1-yl)phenylamino) imidazo[1,2-a]pyrazin-6-yl)phenyl)-4,7-methano-4,5,6,7-tetrahydrobenzo[b]thiophene-2-carboxamide;

N-(2-fluoro-5-(2-(4-(4-methylpiperazin-1-yl)phenylamino) pyrimidin-4-yl)phenyl)-4,7-methano-4,5,6,7-tetrahydrobenzo[b]thiophene-2-carboxamide;

N-(2-fluoro-5-(1-methyl-5-(5-(4-methylpiperazin-1-yl)pyridin-2-ylamino)-6-oxo-1,6-dihydropyridin-3-yl)phenyl)-4,7-ethano-4,5,6,7-tetrahydrobenzo[b]thiophene-2-carboxamide;

N-(2-fluoro-5-(4-methyl-6-(4-(4-methylpiperazin-1-yl)phenylamino)-5-oxo-4,5-dihydropyrazin-2-yl)phenyl)-4,7-ethano-4,5,6,7-tetrahydrobenzo[b]thiophene-2-carboxamide;

N-(2-fluoro-5-(1-methyl-5-(5-(4-methylpiperazin-1-yl)pyridin-2-ylamino)-6-oxo-1,6-dihydropyridin-3-yl)phenyl)-4,6-ethano-4,5,6,7-tetrahydrobenzo[b]thiophene-2-carboxamide;

N-(2-fluoro-5-(4-methyl-6-(4-(4-methylpiperazin-1-yl)phenylamino)-5-oxo-4,5-dihydropyrazin-2-yl)phenyl)-4,6-ethano-4,5,6,7-tetrahydrobenzo[b]thiophene-2-carboxamide;

N-(2-fluoro-5-(1-methyl-5-(5-(4-methylpiperazin-1-yl)pyridin-2-ylamino)-6-oxo-1,6-dihydropyridin-3-yl)phenyl)-4,7-ethano-4,5,6,7-tetrahydrobenzo[d]thiazole-2-carboxamide;

N-(2-fluoro-5-(4-methyl-6-(4-(4-methylpiperazin-1-yl)phenylamino)-5-oxo-4,5-dihydropyrazin-2-yl)phenyl)-4,7-ethano-4,5,6,7-tetrahydrobenzo[d]thiazole-2-carboxamide;

N-(2-fluoro-5-(1-methyl-5-(5-(4-methylpiperazin-1-yl)pyridin-2-ylamino)-6-oxo-1,6-dihydropyridin-3-yl)phenyl)-5,8-ethano-5,6,7,8-tetrahydronaphthalene-2-carboxamide;

N-(2-fluoro-5-(4-methyl-6-(4-(4-methylpiperazin-1-yl)phenylamino)-5-oxo-4,5-dihydropyrazin-2-yl)phenyl)-5,8-ethano-5,6,7,8-tetrahydronaphthalene-2-carboxamide; and pharmaceutically acceptable salts, solvates, chelates, non-covalent complexes, prodrugs, and mixtures thereof.

The present compounds described herein are potent inhibitors of Btk. While not being bound by any theory, certain compounds have improved properties in the form of greater efficacy (as measured by, for example, the inhibition of Btk in whole blood and the inhibition of B-cell activation in mice).

Methods for obtaining the novel compounds described herein will be apparent to those of ordinary skill in the art, suitable procedures being described, for example, in the reaction scheme and examples below, and in analogous methods known in the art. See, also, U.S. application Ser. No. 11/371,180, filed Mar. 9, 2006, which is incorporated herein by reference in its entirety. For example, compounds of Formula I with various $R_1$ groups may be made from the following compounds:

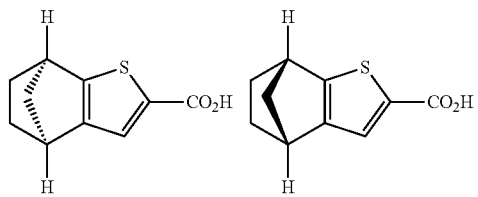

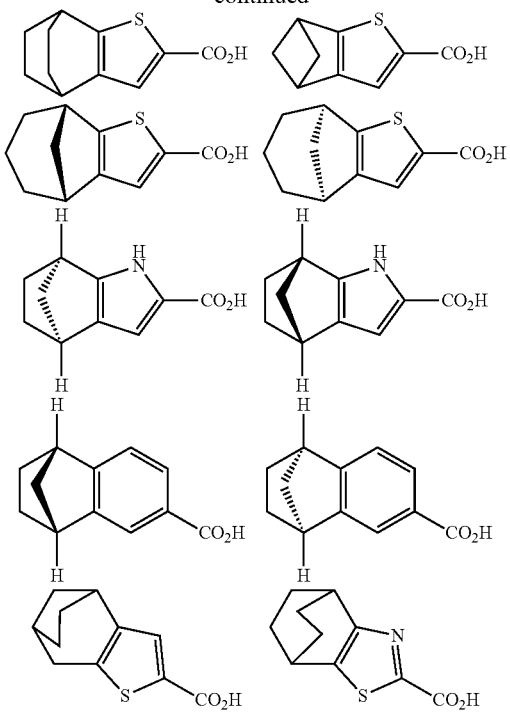

i.e., (4S,7R)-4,7-methano-4,5,6,7-tetrahydro-1-benzothiophene-2-carboxylic acid;
(4R,7S)-4,7-methano-4,5,6,7-tetrahydro-1-benzothiophene-2-carboxylic acid;
4,7-ethano-4,5,6,7-tetrahydro-1-benzothiophene-2-carboxylic acid;
5,6-dihydro-4,6-methano-4H-cyclopenta[b]thiophene-2-carboxylic acid;
(4R,8S)-5,6,7,8-tetrahydro-4,8-methano-8H-cyclohepta[b]thiophene-2-carboxylic acid;
(4S,8R)-5,6,7,8-tetrahydro-4,8-methano-8H-cyclohepta[b]thiophene-2-carboxylic acid;
(4S,7R)-4,7-methano-4,5,6,7-tetrahydro-indole-2-carboxylic acid;
(4R,7S)-4,7-methano-4,5,6,7-tetrahydro-indole-2-carboxylic acid;
(1S,4R)-1,4-methano-1,2,3,4-tetrahydronaphthalene-6-carboxylic acid;
(1R,4S)-1,4-methano-1,2,3,4-tetrahydronaphthalene-6-carboxylic acid;
4,6-ethano-4,5,6,7-tetrahydrobenzo[b]thiophene-2-carboxylic acid; and
4,7-ethano-4,5,6,7-tetrahydrobenzo[d]thiazole-2-carboxylic acid.

In some embodiments, compounds of Formula I are administered as a pharmaceutical composition or formulation. Accordingly, the invention provides pharmaceutical formulations comprising a compound of Formula I and pharmaceutically acceptable salts, solvates, chelates, non-covalent complexes, prodrugs, and mixtures thereof, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such as sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound of the present invention.

Effective concentrations of a compound of Formula I and pharmaceutically acceptable salts, solvates, chelates, non-covalent complexes, prodrugs, and mixtures thereof, are mixed with a suitable pharmaceutical acceptable vehicle. In instances in which the compound exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of the compound of Formula I, the resulting mixture may be a solution, suspension, emulsion or the like. The form of the resulting mixture depends upon a number of factors, including the intended mode of administration and the solubility of the compound in the chosen vehicle. The effective concentration sufficient for ameliorating the symptoms of the disease treated may be empirically determined.

Compounds of Formula I may be administered orally, topically, parenterally, intravenously, by intramuscular injection, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral formulations contain from 0.1 to 99% of a compound of Formula I. In some embodiments, oral formulations contain at least 5% (weight %) of a compound of Formula I. Some embodiments contain from 25% to 50% or from 5% to 75% of a compound of Formula I.

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol, or sucrose. Such formulations may also contain a demulcent.

Compounds of Formula I can be incorporated into oral liquid preparations such as aqueous or oily suspensions, solutions, emulsions, syrups, or elixirs, for example. Moreover, formulations containing these chemical entities can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients include suspending agents, for example sodium carboxymethylcellulose, methylcellulose, hydropropylmethylcellulose, sodium alginate, polyvinylpyrrolidone, gum tragacanth and gum acacia; dispersing or wetting agents; naturally-occurring phosphatides, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Compounds of Formula I may be administered parenterally in a sterile medium. Parenteral administration includes subcutaneous injections, intravenous, intramuscular, intrathecal injection or infusion techniques. Compounds of Formula I, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

Compounds of Formula I may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Compounds of Formula I may be formulated for local or topical application, such as for topical application to the skin and mucous membranes, such as in the eye, in the form of gels, creams, and lotions and for application to the eye. Topical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. Compounds of Formula I may also be formulated for transdermal administration as a transdermal patch.

Topical compositions comprising a compound of Formula I can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

Compounds of Formula I may also be topically administered in the form of liposome delivery systems, such as small unilamellar vesicles, large unilamellar vesicles, and multilamellar vesicles. Liposomes can be formed from a variety of phospholipids, such as cholesterol, stearylamine and phosphatidylcholines.

Other compositions useful for attaining systemic delivery of the compound include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

The compositions of the present invention may also optionally comprise an activity enhancer. The activity enhancer can be chosen from a wide variety of molecules that function in different ways to enhance or be independent of therapeutic effects of the present compounds. Particular classes of activity enhancers include skin penetration enhancers and absorption enhancers.

Pharmaceutical compositions of the invention may also contain additional active agents that can be chosen from a wide variety of molecules, which can function in different ways to enhance the therapeutic effects of a compound of Formula I. These optional other active agents, when present, are typically employed in the compositions of the invention at a level ranging from 0.01% to 15%. Some embodiments contain from 0.1% to 10% by weight of the composition. Other embodiments contain from 0.5% to 5% by weight of the composition.

The invention includes packaged pharmaceutical formulations. Such packaged formulations include a pharmaceutical composition comprising a compound of Formula I and pharmaceutically acceptable salts, solvates, chelates, non-covalent complexes, prodrugs, and mixtures thereof, and instructions for using the composition to treat a mammal (typically a human patient). In some embodiments, the instructions are for using the pharmaceutical composition to treat a patient suffering from a disease responsive to inhibition of Btk activity and/or inhibition of B-cell and/or myeloid-cell activity. The invention can include providing prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the compounds of Formula I can be administered alone, as mixtures, or in combination with other active agents.

Accordingly, the invention includes a method of treating a patient, for example, a mammal, such as a human, having a disease responsive to inhibition of Btk activity, comprising administrating to the patient having such a disease, an effective amount of a compound of Formula I and pharmaceutically acceptable salts, solvates, chelates, non-covalent complexes, prodrugs, and mixtures thereof.

To the extent that Btk is implicated in disease, alleviation of the disease, disease symptoms, preventative, and prophylactic treatment is within the scope of this invention. In some embodiments, compounds of Formula I may also inhibit other kinases, such that alleviation of disease, disease symptoms, preventative, and prophylactic treatment of conditions associated with these kinases is also within the scope of this invention.

Methods of treatment also include inhibiting Btk activity and/or inhibiting B-cell and/or myeloid-cell activity, by inhibiting ATP binding or hydrolysis by Btk or by some other mechanism, in vivo, in a patient suffering from a disease responsive to inhibition of Btk activity, by administering an effective concentration of a compound of Formula I and pharmaceutically acceptable salts, solvates, chelates, non-covalent complexes, prodrugs, and mixtures thereof. An example of an effective concentration would be that concentration sufficient to inhibit Btk activity in vitro. An effective concentration may be ascertained experimentally, for example by assaying blood concentration of the compound, or theoretically, by calculating bioavailability.

In some embodiments, the condition responsive to inhibition of Btk activity and/or B-cell and/or myeloid-cell activity is cancer, a bone disorder, an allergic disorder and/or an autoimmune and/or inflammatory disease, and/or an acute inflammatory reaction.

The invention includes a method of treating a patient having cancer, a bone disorder, an allergic disorder and/or an autoimmune and/or inflammatory disease, and/or an acute inflammatory reaction, by administering an effective amount of a compound of Formula I and pharmaceutically acceptable salts, solvates, chelates, non-covalent complexes, prodrugs, and mixtures thereof.

In some embodiments, the conditions and diseases that can be affected using compounds of Formula I, include, but are not limited to:

allergic disorders, including but not limited to eczema, allergic rhinitis or coryza, hay fever, bronchial asthma, urticaria (hives) and food allergies, and other atopic conditions;

autoimmune and/or inflammatory diseases, including but not limited to psoriasis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, osteoarthritis, chronic Idiopathic thrombocytopenic purpura (ITP), Addison's disease, Parkinson's disease, Alzheimer's disease, Diabetes mellitus (type 1), septic shock, myasthenia gravis, Ulcerative Colitis, Aplastic anemia, Coeliac disease, Wegener's granulomatosis and other diseases in which the cells and antibodies arise from and are directed against the individual's own tissues;

acute inflammatory reactions, including but not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, and cholocystitis, cancer, including but not limited to hematological malignancies, such as B-cell lymphoma, and acute lymphoblastic leukemia, acute myelogenous leukemia, chronic myelogenous leukemia, chronic and acute lymphocytic leukemia, hairy cell leukemia, Hodgkin's disease, Non-Hodgkin lymphoma, multiple myeloma, and other diseases that are characterized by cancer of the blood or lymphatic system, and bone disorders, including but not limited to osteoporosis.

Btk is a known inhibitor of apoptosis in lymphoma B-cells. Defective apoptosis contributes to the pathogenesis and drug resistance of human leukemias and lymphomas. Thus, further provided is a method of promoting or inducing apoptosis in cells expressing Btk comprising contacting the cell with a compound of Formula I, pharmaceutically acceptable salts, solvates, chelates, non-covalent complexes, prodrugs, and mixtures thereof.

The invention provides methods of treatment in which a compound of Formula I, and pharmaceutically acceptable salts, solvates, chelates, non-covalent complexes, prodrugs, and mixtures thereof, is the only active agent given to a patient and also includes methods of treatment in which a compound of Formula I, and pharmaceutically acceptable salts, solvates, chelates, non-covalent complexes, prodrugs, and mixtures thereof, is given to a patient in combination with one or more additional active agents.

Thus in one embodiment the invention provides a method of treating cancer, a bone disorder, an allergic disorder and/or an autoimmune and/or inflammatory disease, and/or an acute inflammatory reaction, which comprises administering to a patient in need thereof an effective amount of a compound of Formula I and pharmaceutically acceptable salts, solvates, chelates, non-covalent complexes, prodrugs, and mixtures thereof, together with a second active agent, which can be useful for treating a cancer, a bone disorder, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with a compound of Formula I and pharmaceutically acceptable salts, solvates, chelates, non-covalent complexes, prodrugs, and mixtures thereof. In certain embodiments, a compound of Formula I and pharmaceutically acceptable salts, solvates, chelates, non-covalent complexes, prodrugs, and mixtures thereof, is combined with another active agent in a single dosage form. Suitable antitumor therapeutics that may be used in combination with a compound of Formula I include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

Compounds of Formula I can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a patient undergoing chemotherapy a chemotherapeutic agent together with a compound of Formula I and pharmaceutically acceptable salts, solvates, chelates, non-covalent complexes, prodrugs, and mixtures thereof, in an amount sufficient to increase the sensitivity of cancer cells to the chemotherapeutic agent is also provided herein.

Examples of other chemotherapeutic drugs that can be used in combination with the present compounds include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), biological agents (e.g. antibodies such as anti CD20 antibody, IDEC 8, immunotoxins, and cytokines), tyrosine kinase inhibitors (e.g., Gleevac), and the like.

Included herein are methods of treatment in which a compound of Formula I and pharmaceutically acceptable salts, solvates, chelates, non-covalent complexes, prodrugs, and mixtures thereof, is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In additional embodiments the anti-inflammatory therapeutic agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, infliximab, and adalimumab (Humira®) which are anti-TNF alpha monoclonal antibodies.

Still other embodiments of the invention pertain to combinations in which at least one active agent is an immunosuppressant compound such as methotrexate, leflunomide, cyclosporine, tacrolimus, azathioprine, or mycophenolate mofetil.

Still other embodiments of the invention pertain to combinations with Rituxan® (Rituximab) or other agents that work by selectively depleting CD20+ B-cells.

Dosage levels of the order, for example, of from 0.1 mg to 140 mg per kilogram of body weight per day can be useful in the treatment of the above-indicated conditions (0.5 mg to 7 g per patient per day). The amount of active ingredient that may be combined with the vehicle to produce a single dosage form will vary depending upon the host treated and the particular mode of administration. Dosage unit forms will generally contain from 1 mg to 500 mg of an active ingredient.

Frequency of dosage may also vary depending on the compound used and the particular disease treated. In some embodiments, for example, for the treatment of an allergic disorder and/or autoimmune and/or inflammatory disease, a dosage regimen of 4 times daily or less is used. In some embodiments, a dosage regimen of 1 or 2 times daily is used. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

A labeled form of a compound of the invention can be used as a diagnostic for identifying and/or obtaining compounds that have the function of modulating an activity of a kinase as described herein. The compounds of the invention may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

The invention is further illustrated by the following non-limiting examples.

EXAMPLE 1

N-(3-(6-(4-(1,4-Dimethyl-3-oxopiperazin-2-yl)phenylamino)-4-methyl-5-oxo-4,5-dihydropyrazin-2-yl)-2-methylphenyl)-4,5,6,7-tetrahydro-4,7-methanobenzo[b]thiophene-2-carboxamide (1q)

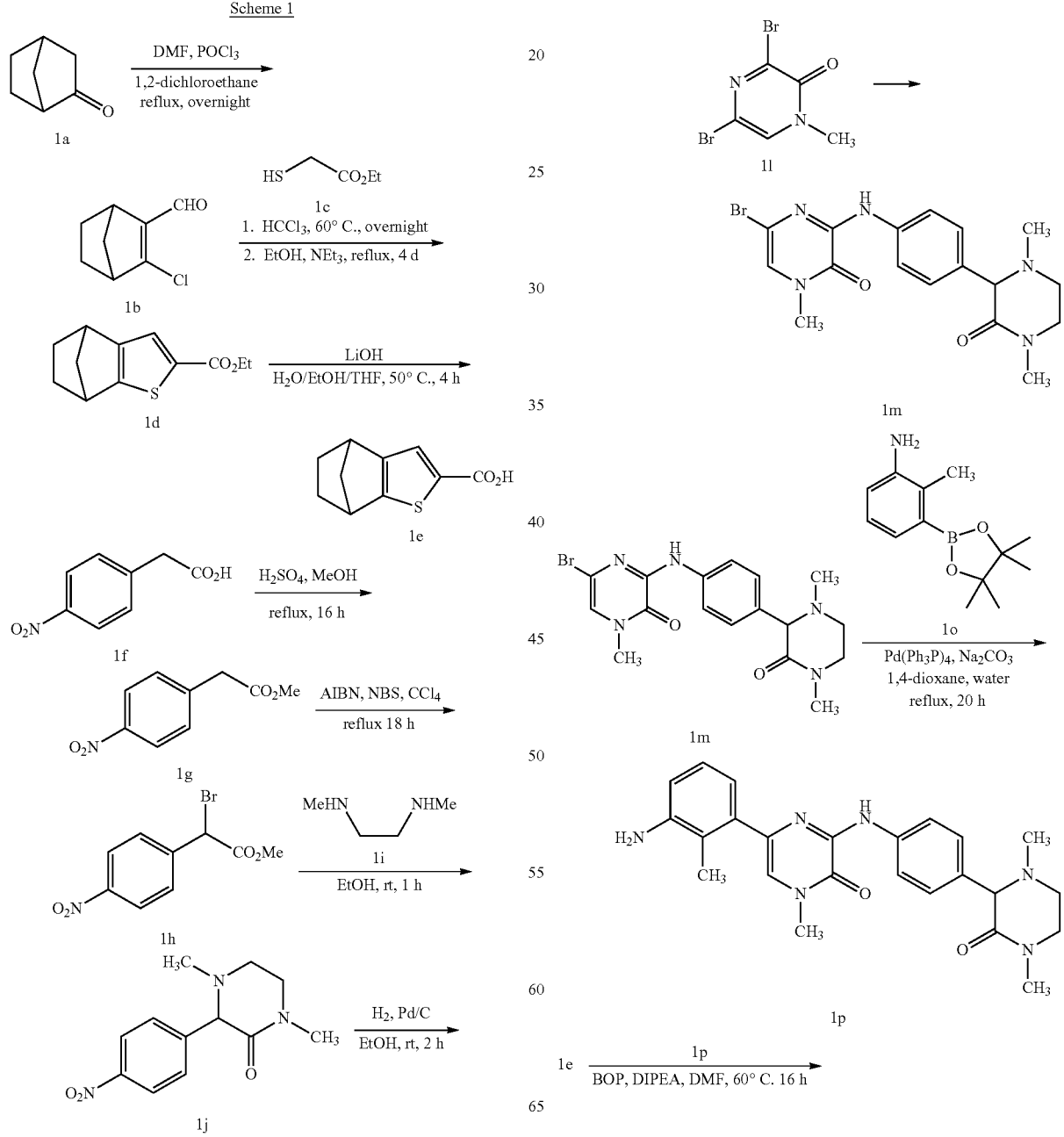

-continued

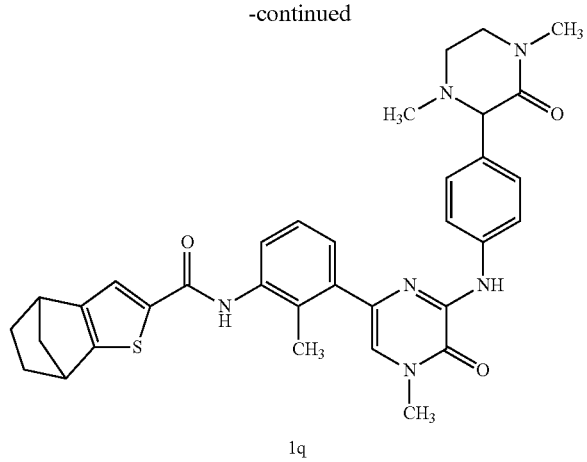

1q

3-Chlorobicyclo[2.2.1]hept-2-ene-2-carbaldehyde (1b)

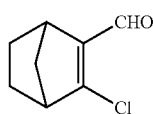

A 250-mL three-neck round-bottomed flask equipped with a magnetic stirrer and reflux condenser was purged with nitrogen and charged with anhydrous 1,2-dichloroethane (24 mL) and anhydrous DMF (9.12 g, 125 mmol). The reaction mixture was cooled to 0° C., and phosphorus oxychloride (15.3 g, 100 mmol) was added over 5 min, while maintaining the reaction temperature between 0 and 10° C. The cooling bath was removed, and the reaction was stirred at room temperature for 30 min. A solution of 1a (5.50 g, 50.0 mmol) in 1,2-dichloroethane (10 mL) was added, and the mixture was heated at 80° C. overnight. After this time, the reaction was poured into a solution of potassium monohydrogenphosphate (43.5 g, 250 mmol) in water (200 mL) and stirred for 15 min. The organic layer was separated and concentrated under reduced pressure. The residue was dissolved in hexanes (100 mL) and washed with water (2×100 mL). The hexanes layer was dried over sodium sulfate, filtered and loaded on a plug of a 15-40 μM silica gel (150 mL). The compound was eluted with a gradient from 0% to 3% of ethyl acetate in hexanes, and the fractions containing 1b were collected to afford, after concentrating under reduced pressure, a 29% yield (2.23 g) of 1b as a yellow oil: $^1$H NMR (300 MHz, CDCl$_3$) δ 9.80 (s, 1H), 3.42 (s, 1H), 3.07 (d, 1H, J=1.7 Hz), 1.95-1.77 (m, 2H), 1.67 (dt, 1H, J=8.9, 1.8 Hz), 1.41-1.17 (m, 3H).

Ethyl 4,5,6,7-Tetrahydro-4,7-methanobenzo[b]thiophene-2-carboxylate (1d)

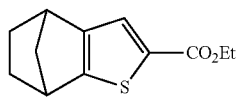

A 50-mL three-neck round-bottomed flask equipped with a magnetic stirrer and reflux condenser was purged with nitrogen and charged with 1b (1.00 g, 6.41 mmol), chloroform (20 mL), 1c (770 mg, 6.45 mmol) and triethylamine (1.31 g, 13.0 mmol), and the mixture was stirred at room temperature for 3 h and then heated at 60° C. overnight. The resulting solution was concentrated under reduced pressure. The residue was dissolved in ethanol (20 mL), and triethylamine (365 mg, 3.61 mmol) was added. After heating the reaction mixture at reflux for 4 d, the solvent was evaporated under reduced pressure, and the resulting residue was partitioned between water (20 mL) and ethyl acetate (20 mL). The layers were separated, and the aqueous phase was extracted with ethyl acetate (20 mL). The organic extracts were combined, dried over sodium sulfate, filtered and the solvent removed under reduced pressure. The resulting residue was eluted with a 3% solution of ethyl acetate in hexanes, and the fractions containing 1d were collected to afford, after concentrating under reduced pressure, a 66% yield (934 mg) of 1d as a yellow oil: $^1$H NMR (500 MHz, CDCl$_3$) δ 7.53 (s, 1H), 4.30 (q, 2H, J=7.0 Hz), 3.55 (m, 1H), 3.42 (m, 1H), 1.97-1.86 (m, 3H), 1.64 (dt, 1H, J=9.0, 1.5 Hz), 1.35 (t, 3H, J=7.0 Hz), 1.09 (m, 2H); MS (ESI+) m/z 223.1 (M+H).

4,5,6,7-Tetrahydro-4,7-methanobenzo[b]thiophene-2-carboxylic Acid (1e)

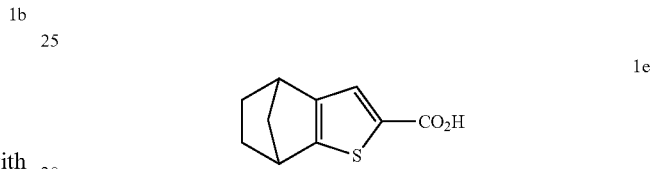

A 100-mL single-neck round bottomed flask equipped with a magnetic stirrer and reflux condenser was purged with nitrogen and charged with 1d (930 mg, 4.19 mmol), ethanol (7 mL), THF (7 mL), water (7 mL) and lithium hydroxide (301 mg, 12.6 mmol) and the mixture heated at 50° C. for 4 h. After this time, the reaction was cooled to room temperature and acidified to pH 1.5 with 2N hydrochloric acid. The resulting precipitate was collected by vacuum filtration, washed with water (2×10 mL) and dried overnight under vacuum to afford a 94% yield (768 mg) of 1e as a white solid: mp 183-184° C.; $^1$H NMR (500 MHz, DMSO-d$_6$) δ 12.66 (br s, 1H), 7.48 (s, 1H), 3.59 (m, 1H), 3.41 (m, 1H), 1.97-1.83 (m, 3H), 1.61 (dt, 1H, J=9.0, 2.5 Hz), 0.96 (dd, 2H, J=12.5, 3.5 Hz); MS (APCI−) m/z 193.2 (M−H).

Methyl 2-(4-Nitrophenyl)acetate (1g)

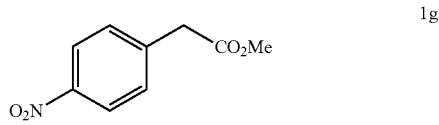 [SMILES: COC(=O)Cc1ccc([N+](=O)[O-])cc1]

A 1-L single-neck round-bottomed flask equipped with a magnetic stirrer and reflux condenser was charged with 2-(4-nitrophenyl)acetic acid (1f) (14.1 g, 77.5 mmol), anhydrous methanol (130 mL) and concentrated sulfuric acid (12.0 mL, 216 mmol), and the reaction mixture was heated at reflux for 16 h. After this time, the reaction was concentrated to dryness under reduced pressure. The resulting residue was partitioned between water (500 mL) and diethyl ether (200 mL) and the layers separated. The aqueous phase was extracted with diethyl ether (100 mL). The combined organic phases were washed with saturated aqueous sodium carbonate and dried over magnesium sulfate, and the drying agent was removed by filtration. The filtrate was concentrated under reduced pressure and dried to a constant weight under vacuum to afford a 96% yield of 1g (14.6 g) as a white solid: mp 45-46° C.; $^1$H NMR (500 MHz, CDCl$_3$) δ 8.19 (d, 2H, J=8.5 Hz), 7.46 (d, 2H, J=8.5 Hz), 3.75 (s, 2H), 3.73 (s, 3H). Reference: *Tetrahedron* 2002, 58, 10113.

Methyl 2-Bromo-2-(4-nitrophenyl)acetate (1 h)

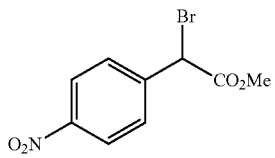

A 1-L single-neck round-bottomed flask equipped with a magnetic stirrer and reflux condenser was charged with 1g (10.6 g, 54.1 mmol), carbon tetrachloride (120 mL), N-bromosuccinimide (10.7 g, 59.9 mmol) and azobisisobutyronitrile (275 mg, 1.67 mmol), and the reaction mixture was heated at reflux for 18 h. After this time the reaction was cooled to room temperature and poured into heptane (120 mL). The resulting suspension was filtered and the filter cake washed with heptane (40 mL). The filtrate was concentrated under reduced pressure and the resulting residue was subjected to flash chromatography to afford 1h in 72% yield (10.7 g) as a clear oil: $^1$H NMR (500 MHz, CDCl$_3$) δ 8.23 (d, 2H, J=9 Hz), 7.74 (d, 2H, J=9.0 Hz), 5.40 (s, 1H), 3.82 (s, 3H); MS (ESI−) m/z 272 (M−H). Reference: *Tetrahedron* 2002, 58, 10113.

1,4-Dimethyl-3-(4-nitrophenyl)piperazin-2-one (1j)

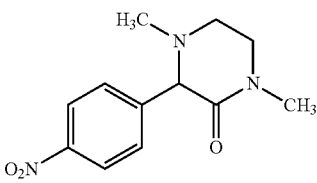

A 100-mL single-neck round-bottomed flask equipped with a magnetic stirrer was purged with nitrogen, charged with N$^1$,N$^2$-dimethylethane-1,2-diamine (1i) (1.61 g, 18.2 mmol), ethanol (5 mL) and 1h (500 mg, 1.82 mmol), and the reaction was stirred at room temperature for 1 h. After this time, the reaction mixture was evaporated under reduced pressure, and the resulting residue was purified by flash column chromatography to afford an 89% yield (404 mg) of 1j as a yellow oil: $^1$H NMR (500 MHz, DMSO-d$_6$) δ 8.18 (d, 2H, J=8.5 Hz), 7.60 (d, 2H, J=8.5 Hz), 3.87 (s, 1H), 3.61 (td, 1H, J=12.0, 4.0 Hz), 3.26 (ddd, 1H, J=12.0, 4.0, 2.5 Hz), 3.02 (ddd, 1H, J=12.0, 4.0, 2.5 Hz), 2.84 (s, 3H), 2.64 (td, 1H, J=12.0, 4.0 Hz), 2.06 (s, 3H).

3-(4-Aminophenyl)-1,4-dimethylpiperazin-2-one (1k)

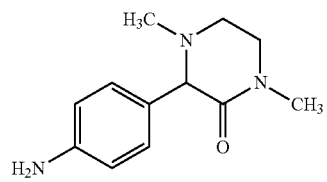

A 50-mL single-neck round-bottomed flask equipped with a magnetic stirrer was purged with nitrogen and charged with 1j (200 mg, 0.80 mmol), ethanol (5 mL) and 10% palladium on carbon (50% wet, 4 mg dry weight). The reaction flask was purged with hydrogen gas and the reaction mixture stirred under a balloon pressure of hydrogen for 2 h. After this time the flask was purged with nitrogen. The catalyst was removed by filtration through a pad of Celite 521 and the filter cake washed with ethanol (10 mL). The filtrate was concentrated under reduced pressure to afford a 94% yield of 1k (166 mg) as a colorless oil: $^1$H NMR (500 MHz, DMSO-d$_6$) δ 6.89 (d, 2H, J=8.5 Hz), 6.47 (d, 2H, J=8.5 Hz), 4.94 (s, 2H), 3.53 (td, 1H, J=12.0, 4.0 Hz), 3.44 (m, 1H), 3.21 (dt, 1H, J=12.0, 4.0 Hz), 2.92 (dt, 1H, J=12.0, 4.0 Hz), 2.82 (s, 3H), 2.02 (s, 3H); MS (ESI+) m/z 220 (M+H).

3,5-dibromo-1-methyl-2(1H)pyrazinone (1l)

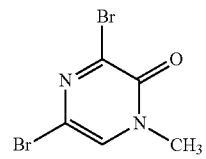

(*J. Heterocycl. Chem.* 1983, 20, 919)

A 250-mL three-neck round-bottomed flask equipped with a magnetic stirrer and reflux condenser was charged with 1,2-dichlorobenzene (100 mL) and oxalyl bromide (60.6 g; 281 mmol). To the solution was added methylamino-acetonitrile (7.01 g; 65.8 mmol) and the reaction heated under nitrogen to 80° C. After 18 h the resulting mixture was cooled to room temperature, evaporated under reduced pressure and the resulting residue purified by flash chromatography to afford 3,5-dibromo-1-methyl-2(1H)pyrazinone (1l) (2.87 g, 16%) as an off-white solid: mp 94-95° C.; MS (ESI+) m/z 267 (M+H).

5-Bromo-3-(4-(1,4-dimethyl-3-oxopiperazin-2-yl) phenylamino)-1-methylpyrazin-2(1H)-one (1m)

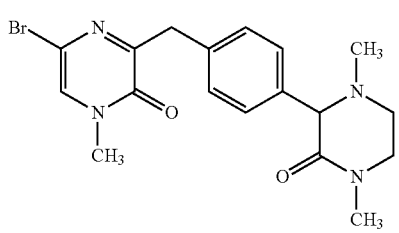

A 100-mL three-neck round-bottomed flask equipped with a mechanical stirrer and reflux condenser was charged with 1k (780 mg, 3.56 mmol), 1l (998 mg, 3.73 mmol), cesium carbonate (2.36 g, 7.26 mmol) and 1,4-dioxane (40 mL). After bubbling nitrogen through the resulting solution for 30 minutes, Xantphos (0.162 g, 0.281 mmol) and tris(dibenzylideneacetone)dipalladium(0) (0.15 g, 0.165 mmol) were added, and the reaction mixture was heated at reflux for 16 h. After this time the reaction was cooled to room temperature and concentrated under reduced pressure. The resulting residue was absorbed onto silica gel and purified by flash chromatography to afford a 57% yield (818 mg) of 1m as an orange solid: mp 206-207° C.; $^1$H NMR (500 MHz, CDCl$_3$) δ 8.27 (bs, 1H), 7.72 (dd, 1H, J=2.0, 8.5 Hz), 7.36 (dd, 2H, J=2.0, 8.5 Hz), 6.73 (s, 1H), 3.71 (m, 1H), 3.69 (s, 1H), 3.52 (s, 3H), 3.21 (m, 1H), 3.01 (m, 1H), 2.97 (s, 3H), 2.67 (m, 1H), 2.19 (s, 3H); MS (ESI+) m/z 406 (M+H).

4,4,5,5-Tetramethyl-2-(2-methyl-3-nitro-phenyl)-[1,3,2]dioxaborolane (1n)

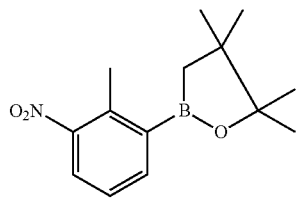

1n

A 1-L three-neck round-bottomed flask equipped with a mechanical stirrer and thermoregulator was purged with nitrogen and charged with 2-bromo-6-nitrotoluene (60.2 g; 278 mmol), bis(pinacolato)diboron (85.2 g; 336 mmol), potassium acetate (82.4 g; 840 mmol) and DMSO (320 mL). A stream of nitrogen was passed through the resulting suspension for 30 min, [1,1'-bis(diphenylphosphino)-ferrocene]dichloropalladium (II), complex with dichloromethane (1:1) (7.60 g; 9.30 mmol) was then added and the reaction heated at 85° C. for 20 h. After this time the mixture was cooled to ambient temperature, poured into a mixture of water (1300 mL) and MtBE (500 mL) and treated with Cellpure P65 (150 cc). The resulting suspension was filtered through a pad of Cellpure P65 (200 cc) packed onto a fritted funnel (ID 185 mm). The filter cake was washed with MtBE (3×180 mL) and the organic layer of the filtrate separated, washed with water (3×1 L) and dried over sodium sulfate. After filtering off sodium sulfate, the filtrate was concentrated and purified by flash chromatography to afford 4,4,5,5-tetramethyl-2-(2-methyl-3-nitro-phenyl)-[1,3,2]dioxaborolane (1n) as a light yellow solid: mp 52-53° C.; MS (APCI+) m/z 264 (M+H).

2-Methyl-3-(4,4,5,5-tetramethyl-[1,3,2]dioxaborolan-2-yl)-phenylamine (1o)

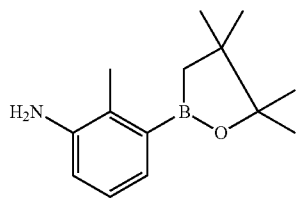

1o

A 500-mL round-bottomed flask equipped with a magnetic stirrer was charged with 4,4,5,5-Tetramethyl-2-(2-methyl-3-nitro-phenyl)-[1,3,2]dioxaborolane (1n) (8.44 g; 32.1 mmol) and methanol (150 mL). The reaction flask was twice evacuated and back-filled with argon. 10% Palladium on charcoal (50% wet, 425 mg dry weight) was then added to the solution, and the reaction flask evacuated and back-filled with hydrogen three times. The reaction was then stirred under balloon pressure of hydrogen at room temperature for 13 h. After this time, the flask was twice evacuated and back-filled with argon, then filtered through a pad of Celite 521 and the filtrate concentrated in vacuo. The resulting residue was dried under high vacuum for 1 d to afford a quantitative yield (8.16 g) of 2-methyl-3-(4,4,5,5-tetramethyl-[1,3,2]dioxaborolan-2-yl)-phenylamine (1o) as a white solid: mp 110-112° C.; MS (ESI+) m/z 234 (M+H).

5-(3-Amino-2-methylphenyl)-3-(4-(1,4-dimethyl-3-oxopiperazin-2-yl)phenylamino)-1-methylpyrazin-2(1H)-one (1p)

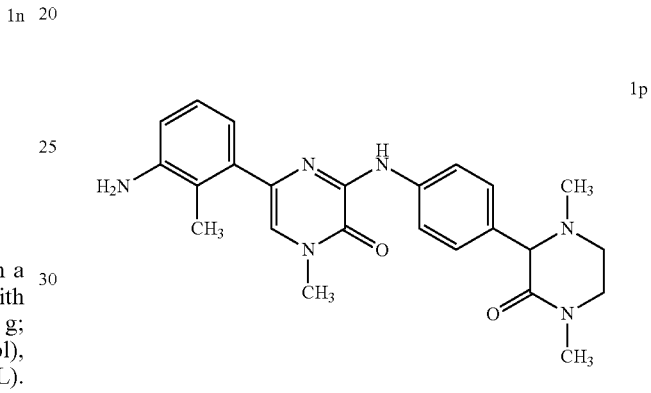

1p

A 250-mL three-neck round-bottomed flask equipped with a magnetic stirrer, reflux condenser and nitrogen inlet was charged with 1m (2.50 g, 6.16 mmol), 1o (1.79 g, 7.70 mmol), 1,4-dioxane (70 mL) and a solution of sodium carbonate (1.96 g, 18.5 mmol) in water (14 mL). After bubbling nitrogen through the resulting mixture for 30 min, tetrakis(triphenylphosphine)palladium (711 mg, 0.62 mmol) was added and the reaction mixture then heated at reflux for 11 h. After this time the reaction was cooled to room temperature and 2N hydrochloric acid (70 mL) followed by ethyl acetate (70 mL) was added. The mixture was stirred for 0.5 h and then filtered through a pad of Celite 521. The organic layer of the filtrate was separated and extracted with 2N hydrochloric acid (2×30 mL). The acidic extracts were combined and washed with ethyl acetate (4×50 mL). The aqueous solution was then stirred vigorously with ethyl acetate (100 mL) while solid potassium carbonate was added portionwise until a pH of 12 was reached. The aqueous layer was separated and extracted with ethyl acetate (2×100 mL). The combined organic layers were washed with brine (70 mL) and dried over magnesium sulfate. The drying agent was removed by filtration, and the filtrate was concentrated under reduced pressure and dried in a 49° C. vacuum oven for 24 h to afford 1p in 86% yield (2.32 g) as an amber foam: mp 133-134° C. $^1$H NMR (500 MHz, CDCl$_3$) δ 8.29 (s, 1H), 7.80 (d, 1H, J=8.5 Hz), 7.29 (d, 2H, J=8.5 Hz), 7.05 (t, 1H, J=8.0 Hz), 6.79 (d, 1H, J=7.5 Hz), 6.73 (d, 1H, J=7.5 Hz), 6.68 (s, 1H), 3.72 (s, 3H), 3.64 (m, 1H), 3.20 (m, 1H), 3.01 (m, 1H), 2.99 (s, 3H), 2.66 (m, 1H), 2.24 (s, 3H), 2.17 (s, 3H); MS (ESI+) m/z 433.3 (M+H).

N-(3-(6-(4-(1,4-Dimethyl-3-oxopiperazin-2-yl)phenylamino)-4-methyl-5-oxo-4,5-dihydropyrazin-2-yl)-2-methylphenyl)-4,5,6,7-tetrahydro-4,7-methanobenzo[b]thiophene-2-carboxamide (1q)

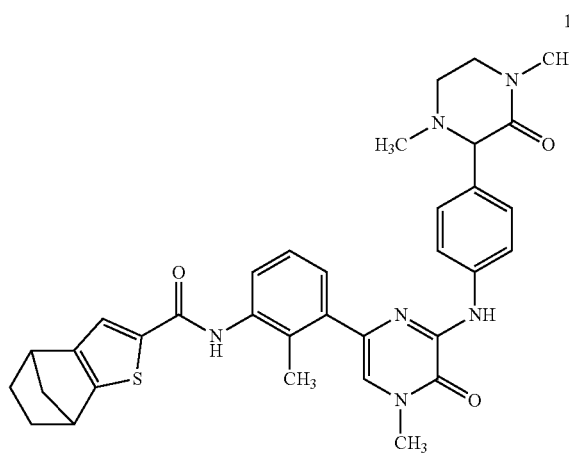

A 50-mL single-neck round-bottomed flask equipped with a magnetic stirrer was purged with nitrogen and charged with 1e (100 mg, 0.515 mmol), 1p (203 mg, 0.469 mmol), N,N-diisopropylethylamine (242 mg, 1.88 mmol) and anhydrous DMF (2 mL). Benzotriazol-1-yl-oxy-tris(dimethylamino) phosphonium hexafluorophosphate (BOP, 249 mg, 0.563 mmol) was added, and the reaction was heated at 60° C. for 16 h. After this time, the reaction was diluted with water (10 mL), and the resulting suspension was filtered. The filter cake was dissolved in methylene chloride (20 mL), and the solution was washed with 10% aqueous citric acid (10 mL), saturated aqueous sodium bicarbonate (10 mL), and water (10 mL), and dried over sodium sulfate. The drying agent was removed by filtration, and the solvent was evaporated under reduced pressure. The resulting residue was eluted with a gradient from 0% to 20% of methanol in ethyl acetate, and the fractions containing 1q were collected to afford, after concentrating under reduced pressure, a 44% yield (127 mg) of 1q as an off-white solid: mp 178-179° C.; $^1$H NMR (500 MHz, CD$_2$Cl$_2$) δ 8.35 (s, 1H), 7.85 (d, 1H, J=8.0 Hz), 7.77 (d, 2H, J=8.5 Hz), 7.59 (s, 1H), 7.42 (s, 1H), 7.29-7.22 (m, 4H), 6.76 (s, 1H), 3.68 (td, 1H, J=11.5, 4.5 Hz), 3.62-3.60 (m, 2H), 3.58 (s, 3H), 3.47 (m, 1H), 3.18 (m, 1H), 2.97 (m, 1H), 2.91 (s, 3H), 2.64 (m, 1H), 2.39 (s, 3H), 2.13 (s, 3H), 1.98-1.90 (m, 3H), 1.67 (dt, 1H, J=9.0, 2.5 Hz), 1.10 (dd, 2H, J=12.5, 3.5 Hz); MS (ESI+) m/z 609.3 (M+H).

EXAMPLE 2

The following compounds were prepared using procedures similar to those described in Example 1.

| Structure | Name | MW calc | MH+ m/z obs |
|---|---|---|---|
| | N-[2-fluoro-5-(1-methyl-5-{[5-(4-methylpiperazin-1-yl)pyridin-2-yl]amino}-6-oxo-1,6-dihydropyridin-3-yl)phenyl]-4,7-methano-4,5,6,7-tetrahydrobenzo[b]thiophene-2-carboxamide | 584 | 585.3 |

-continued

| Structure | Name | MW calc | MH+ m/z obs |
|---|---|---|---|
| 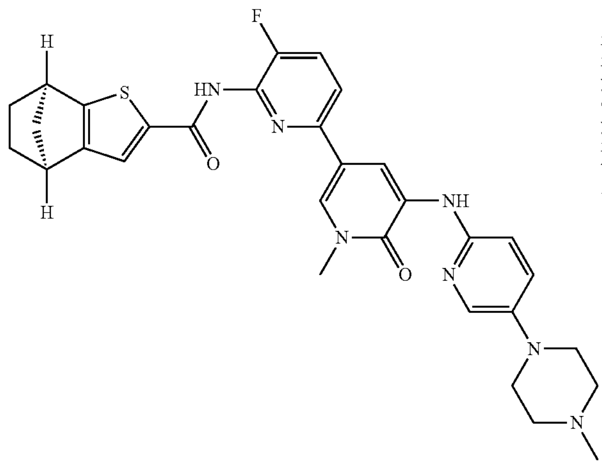 [SMILES: CN1CCN(c2ccc(Nc3cc(-c4ccc(F)c(NC(=O)c5cc6c(s5)[C@@H]5CC[C@H]6C5)n4)cn(C)c3=O)nc2)CC1] | (4S,7R)-N-[3-fluoro-6-(1-methyl-5-{[5-(4-methylpiperazin-1-yl)pyridin-2-yl]amino}-6-oxo-1,6-dihydropyridin-3-yl)pyridin-2-yl]-4,7-methano-4,5,6,7-tetrahydrobenzo[b]thiophene-2-carboxamide (+) isomer | 585 | 586.3 |
| 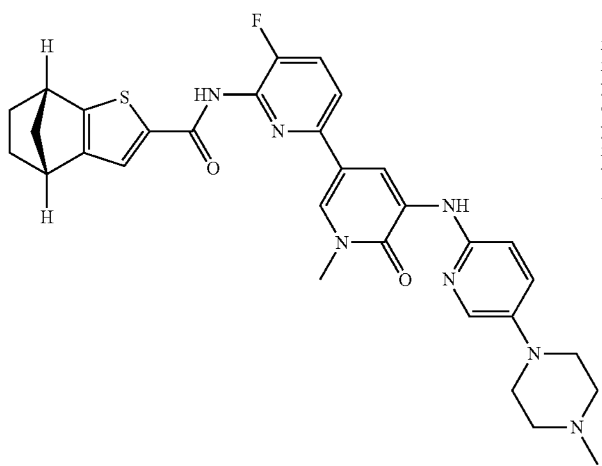 [SMILES: CN1CCN(c2ccc(Nc3cc(-c4ccc(F)c(NC(=O)c5cc6c(s5)[C@H]5CC[C@@H]6C5)n4)cn(C)c3=O)nc2)CC1] | (4R,7S)-N-[3-fluoro-6-(1-methyl-5-{[5-(4-methylpiperazin-1-yl)pyridin-2-yl]amino}-6-oxo-1,6-dihydropyridin-3-yl)pyridin-2-yl]-4,7-methano-4,5,6,7-tetrahydrobenzo[b]thiophene-2-carboxamide (−) isomer | 585 | 586.3 |
| 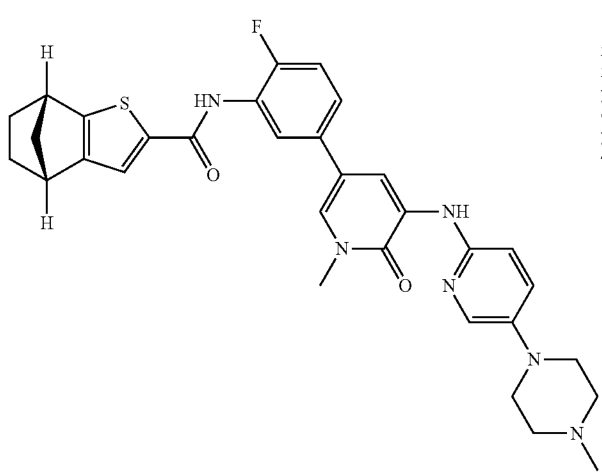 [SMILES: CN1CCN(c2ccc(Nc3cc(-c4ccc(F)c(NC(=O)c5cc6c(s5)[C@H]5CC[C@@H]6C5)c4)cn(C)c3=O)nc2)CC1] | (4R,7S)-N-[2-fluoro-5-(1-methyl-5-{[5-(4-methylpiperazin-1-yl)pyridin-2-yl]amino}-6-oxo-1,6-dihydropyridin-3-yl)phenyl]-4,7-methano-4,5,6,7-tetrahydrobenzo[b]thiophene-2-carboxamide (−) isomer | 584 | 585.3 |

| Structure | Name | MW calc | MH+ m/z obs |
|---|---|---|---|
| 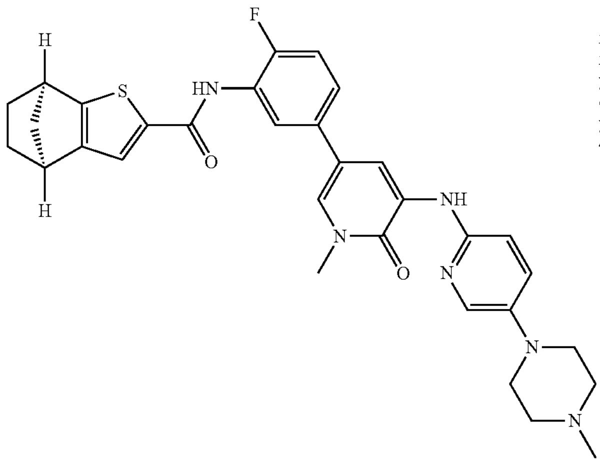 [SMILES: CN1CCN(c2ccc(Nc3cc(-c4ccc(F)c(NC(=O)c5cc6c(s5)[C@@H]5CC[C@H]6C5)c4)cn(C)c3=O)nc2)CC1] | (4S,7R)-N-[2-fluoro-5-(1-methyl-5-{[5-(4-methylpiperazin-1-yl)pyridin-2-yl]amino}-6-oxo-1,6-dihydropyridin-3-yl)phenyl]-4,7-methano-4,5,6,7-tetrahydrobenzo[b]thiophene-2-carboxamide (+) isomer | 584 | 585.3 |

EXAMPLE 3

The following compounds can be prepared using procedures similar to those described in Example 1 and those known in the art.

| Structure | Name |
|---|---|
| 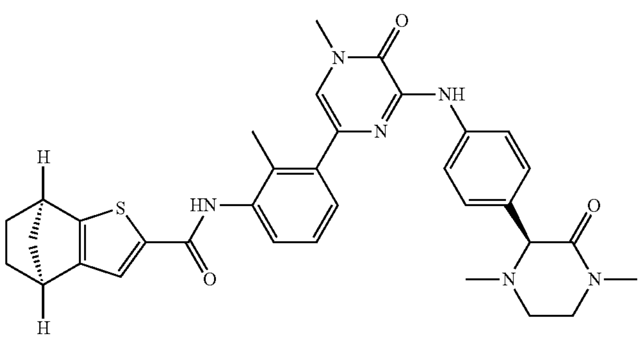 [SMILES: Cc1c(NC(=O)c2cc3c(s2)[C@@H]2CC[C@H]3C2)cccc1-c1cn(C)c(=O)c(Nc2ccc([C@H]3C(=O)N(C)CCN3C)cc2)n1] | N-{3-[6-({4-[(2S)-1,4-dimethyl-3-oxopiperazin-2-yl]phenyl}amino)-4-methyl-5-oxo-4,5-dihydropyrazin-2-yl]-2-methylphenyl}-(4S,7R)-4,7-methano-4,5,6,7-tetrahydro-1-benzothiophene-2-carboxamide |
| 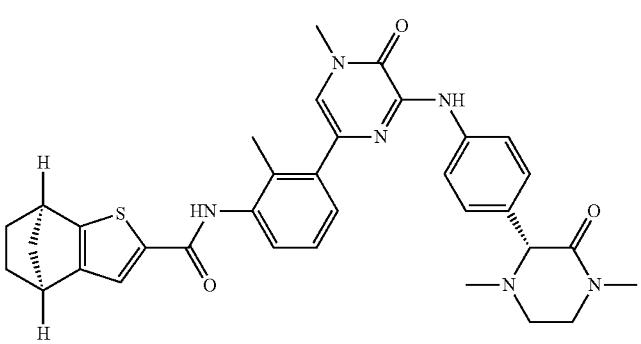 [SMILES: Cc1c(NC(=O)c2cc3c(s2)[C@@H]2CC[C@H]3C2)cccc1-c1cn(C)c(=O)c(Nc2ccc([C@@H]3C(=O)N(C)CCN3C)cc2)n1] | N-{3-[6-({4-[(2R)-1,4-dimethyl-3-oxopiperazin-2-yl]phenyl}amino)-4-methyl-5-oxo-4,5-dihydropyrazin-2-yl]-2-methylphenyl}-(4S,7R)-4,7-methano-4,5,6,7-tetrahydro-1-benzothiophene-2-carboxamide |

| Structure | Name |
|---|---|
| 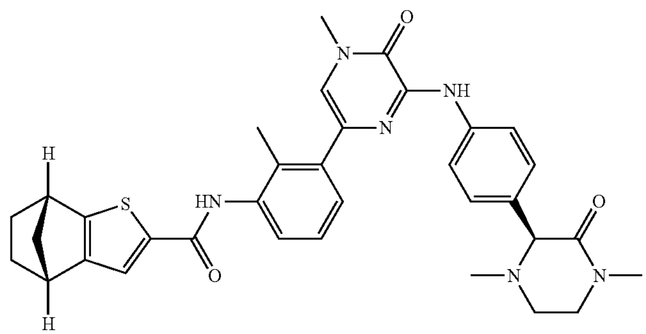 [SMILES: Cc1c(NC(=O)c2cc3c(s2)[C@H]2CC[C@@H]3C2)cccc1-c1cn(C)c(=O)c(Nc2ccc([C@H]3C(=O)N(C)CCN3C)cc2)n1] | N-{3-[6-({4-[(2S)-1,4-dimethyl-3-oxopiperazin-2-yl]phenyl}amino)-4-methyl-5-oxo-4,5-dihydropyrazin-2-yl]-2-methylphenyl}-(4R,7S)-4,7-methano-4,5,6,7-tetrahydro-1-benzothiophene-2-carboxamide |
| 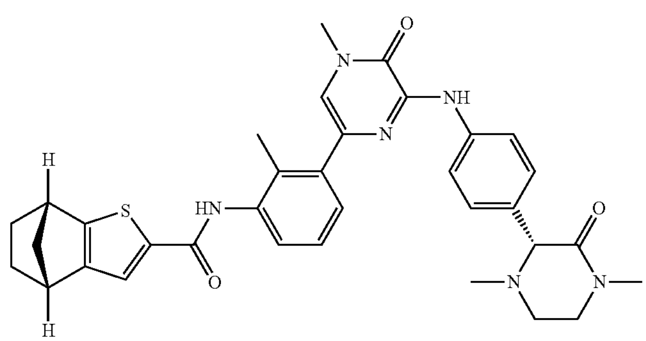 [SMILES: Cc1c(NC(=O)c2cc3c(s2)[C@H]2CC[C@@H]3C2)cccc1-c1cn(C)c(=O)c(Nc2ccc([C@@H]3C(=O)N(C)CCN3C)cc2)n1] | N-{3-[6-({4-[(2R)-1,4-dimethyl-3-oxopiperazin-2-yl]phenyl}amino)-4-methyl-5-oxo-4,5-dihydropyrazin-2-yl]-2-methylphenyl}-(4R,7S)-4,7-methano-4,5,6,7-tetrahydro-1-benzothiophene-2-carboxamide |
| 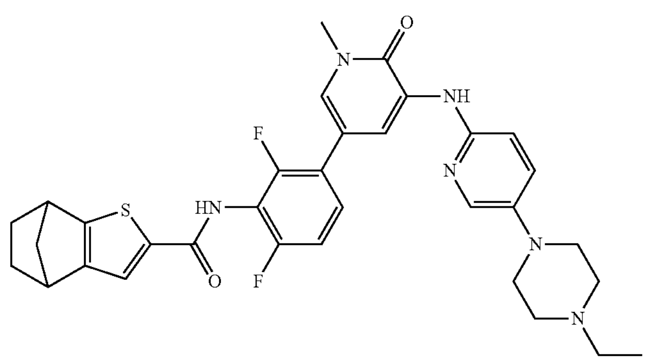 [SMILES: CCN1CCN(c2ccc(Nc3cc(-c4ccc(F)c(NC(=O)c5cc6c(s5)C5CCC6C5)c4F)cn(C)c3=O)nc2)CC1] | N-[3-(5-{[5-(4-ethylpiperazin-1-yl)pyridin-2-yl]amino}-1-methyl-6-oxo-1,6-dihydropyridin-3-yl)-2,4-difluorophenyl]-4,7-methano-4,5,6,7-tetrahydro-1-benzothiophene-2-carboxamide |

-continued

| Structure | Name |
|---|---|
| 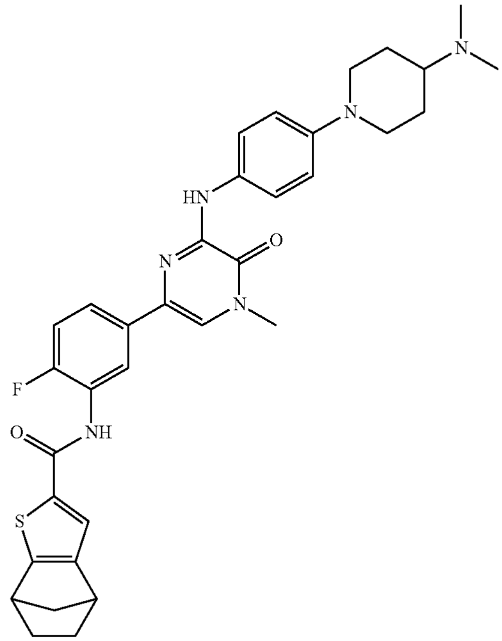 [SMILES: CN(C)C1CCN(c2ccc(Nc3nc(-c4ccc(F)c(NC(=O)c5cc6c(s5)C5CCC6C5)c4)cn(C)c3=O)cc2)CC1] | N-(5-(6-(4-(4-(dimethylamino)piperidin-1-yl)phenylamino)-4-methyl-5-oxo-4,5-dihydropyrazin-2-yl)-2-fluorophenyl)-4,7-methano-4,5,6,7-tetrahydrobenzo[b]thiophene-2-carboxamide |
| 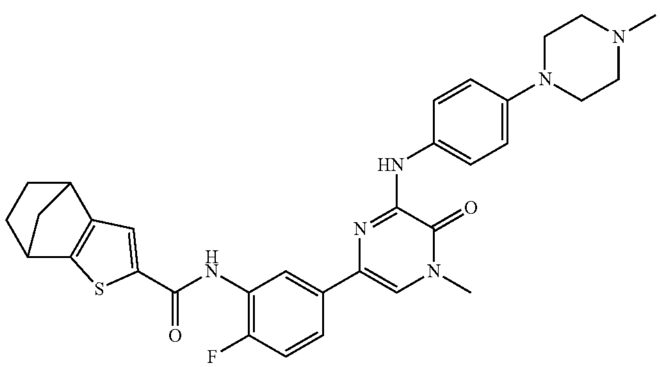 [SMILES: CN1CCN(c2ccc(Nc3nc(-c4ccc(F)c(NC(=O)c5cc6c(s5)C5CCC6C5)c4)cn(C)c3=O)cc2)CC1] | N-(2-fluoro-5-(4-methyl-6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide |
| 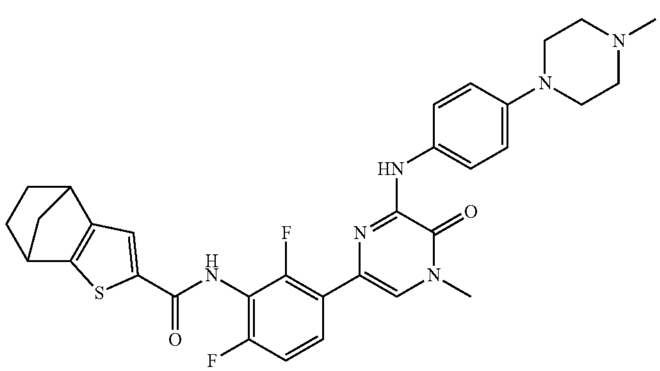 [SMILES: CN1CCN(c2ccc(Nc3nc(-c4ccc(F)c(NC(=O)c5cc6c(s5)C5CCC6C5)c4F)cn(C)c3=O)cc2)CC1] | N-(2,4-difluoro-5-(4-methyl-6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide |

| Structure | Name |
|---|---|
| 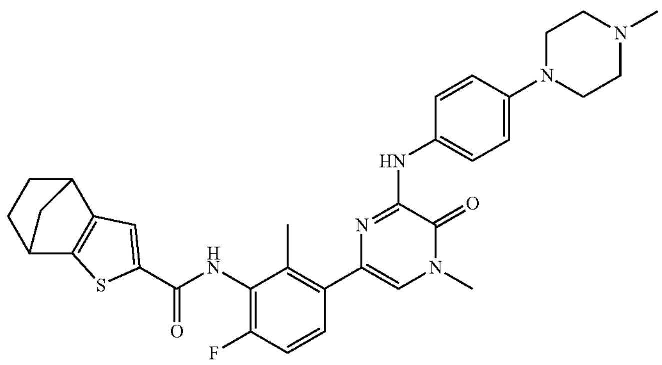 [SMILES: Cc1c(-c2cn(C)c(=O)c(Nc3ccc(N4CCN(C)CC4)cc3)n2)ccc(F)c1NC(=O)c1cc2c(s1)C1CCC2C1] | N-(2-methyl-4-fluoro-5-(4-methyl-6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide |
| 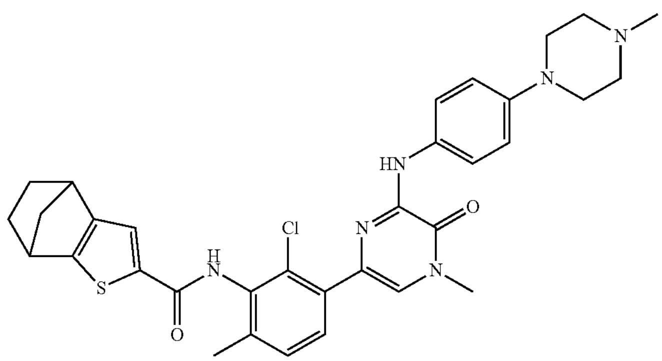 [SMILES: Cc1ccc(-c2cn(C)c(=O)c(Nc3ccc(N4CCN(C)CC4)cc3)n2)c(Cl)c1NC(=O)c1cc2c(s1)C1CCC2C1] | N-(2-chloro-4-methyl-5-(4-methyl-6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide |
| 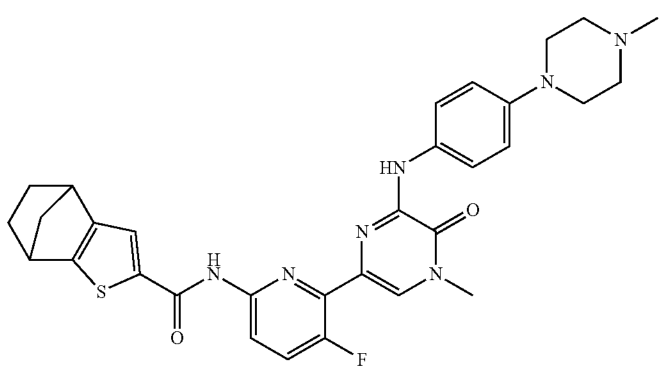 [SMILES: CN1CCN(c2ccc(Nc3nc(-c4nc(NC(=O)c5cc6c(s5)C5CCC6C5)ccc4F)cn(C)c3=O)cc2)CC1] | N-(5-fluoro-6-(4-methyl-6-(4-(4-methylpiperazin-1-yl)phenylamino)-5-oxo-4,5-dihydropyrazin-2-yl)pyridin-2-yl)-4,7-methano-4,5,6,7-tetrahydrobenzo[b]thiophene-2-carboxamide |
| 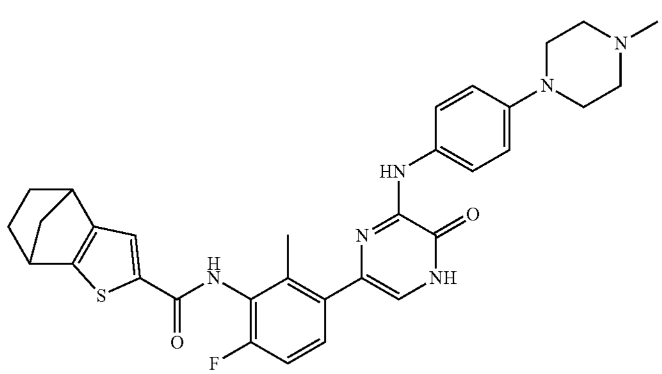 [SMILES: Cc1c(-c2c[nH]c(=O)c(Nc3ccc(N4CCN(C)CC4)cc3)n2)ccc(F)c1NC(=O)c1cc2c(s1)C1CCC2C1] | N-(4-fluoro-2-methyl-3-(6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide |

| Structure | Name |
|---|---|
| 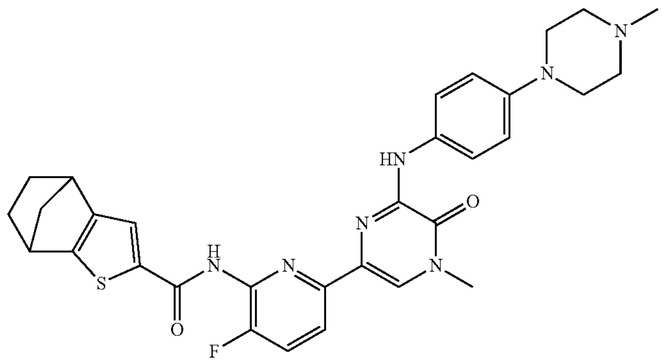 [SMILES: CN1CCN(c2ccc(Nc3nc(-c4ccc(F)c(NC(=O)c5cc6c(s5)C5CCC6C5)n4)cn(C)c3=O)cc2)CC1] | N-(3-fluoro-6-(4-methyl-6-(4-(4-methylpiperazin-1-yl)phenylamino)-5-oxo-4,5-dihydropyrazin-2-yl)pyridin-2-yl)-4,7-methano-4,5,6,7-tetrahydrobenzo[b]thiophene-2-carboxamide |
| 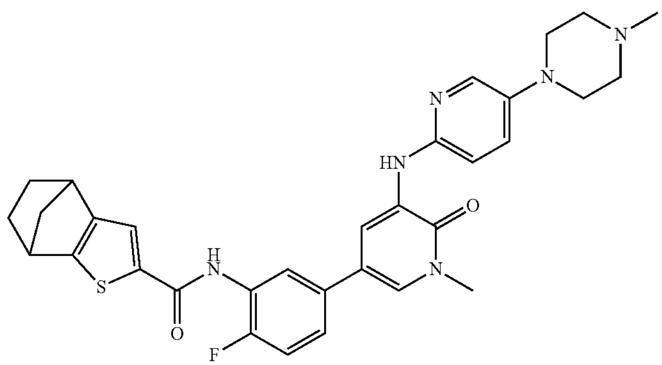 [SMILES: CN1CCN(c2ccc(Nc3cc(-c4ccc(F)c(NC(=O)c5cc6c(s5)C5CCC6C5)c4)cn(C)c3=O)nc2)CC1] | N-(2-fluoro-5-(1-methyl-5-(5-(4-methylpiperazin-1-yl)pyridin-2-ylamino)-6-oxo-1,6-dihydropyridin-3-yl)phenyl)-4,7-methano-4,5,6,7-tetrahydrobenzo[b]thiophene-2-carboxamide |
| 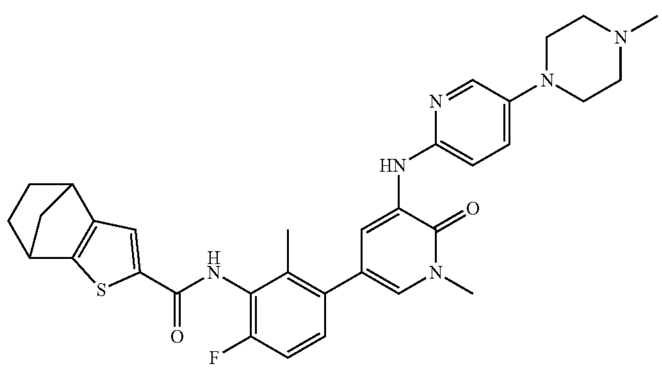 [SMILES: Cc1c(-c2cc(Nc3ccc(N4CCN(C)CC4)cn3)c(=O)n(C)c2)ccc(F)c1NC(=O)c1cc2c(s1)C1CCC2C1] | N-(6-fluoro-2-methyl-3-(1-methyl-5-(5-(4-methylpiperazin-1-yl)pyridin-2-ylamino)-6-oxo-1,6-dihydropyridin-3-yl)phenyl)-4,7-methano-4,5,6,7-tetrahydrobenzo[b]thiophene-2-carboxamide |
| 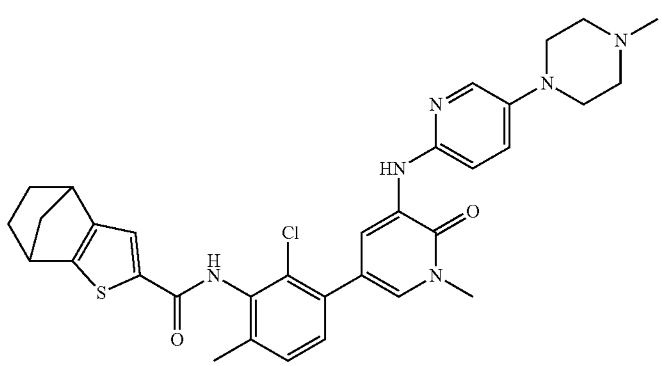 [SMILES: Cc1ccc(-c2cc(Nc3ccc(N4CCN(C)CC4)cn3)c(=O)n(C)c2)c(Cl)c1NC(=O)c1cc2c(s1)C1CCC2C1] | N-(2-chloro-6-methyl-3-(1-methyl-5-(5-(4-methylpiperazin-1-yl)pyridin-2-ylamino)-6-oxo-1,6-dihydropyridin-3-yl)phenyl)-4,7-methano-4,5,6,7-tetrahydrobenzo[b]thiophene-2-carboxamide |

| Structure | Name |
|---|---|
| 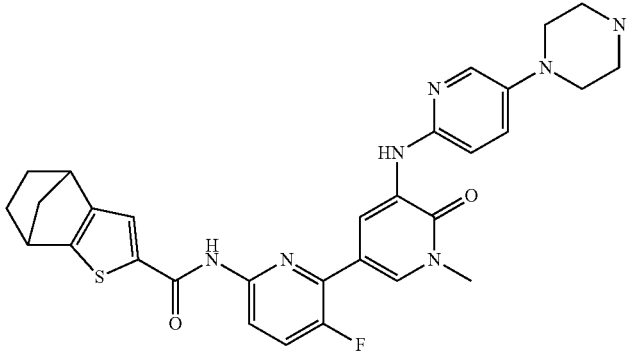 | N-(5-fluoro-6-(1-methyl-5-(5-(4-methylpiperazin-1-yl)pyridin-2-ylamino)-6-oxo-1,6-dihydropyridin-3-yl)pyridin-2-yl)-4,7-methano-4,5,6,7-tetrahydrobenzo[b]thiophene-2-carboxamide |
| 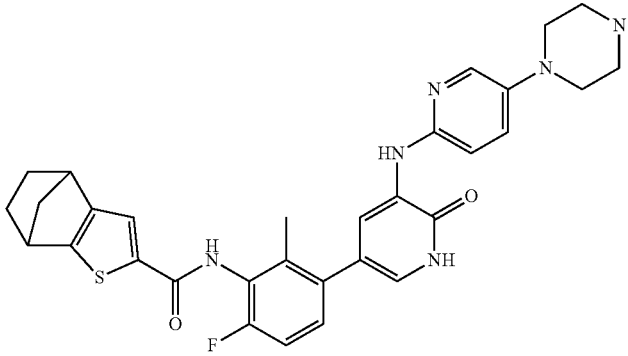 | N-(6-fluoro-2-methyl-3-(5-(5-(4-methylpiperazin-1-yl)pyridin-2-ylamino)-6-oxo-1,6-dihydropyridin-3-yl)phenyl)-4,7-methano-4,5,6,7-tetrahydrobenzo[b]thiophene-2-carboxamide |
| 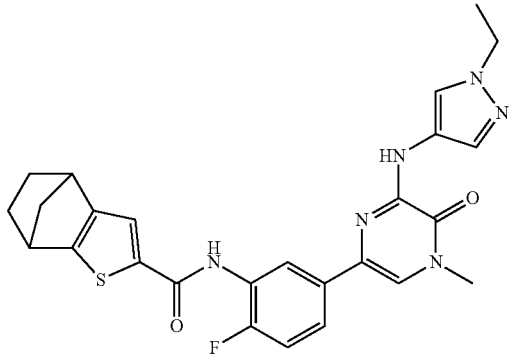 [SMILES: CCn1cc(Nc2nc(-c3ccc(F)c(NC(=O)c4cc5c(s4)C4CCC5C4)c3)cn(C)c2=O)cn1] | N-(5-(6-(1-ethyl-1H-pyrazol-4-ylamino)-4-methyl-5-oxo-4,5-dihydropyrazin-2-yl)-2-fluorophenyl)-4,7-methano-4,5,6,7-tetrahydrobenzo[b]thiophene-2-carboxamide |
| 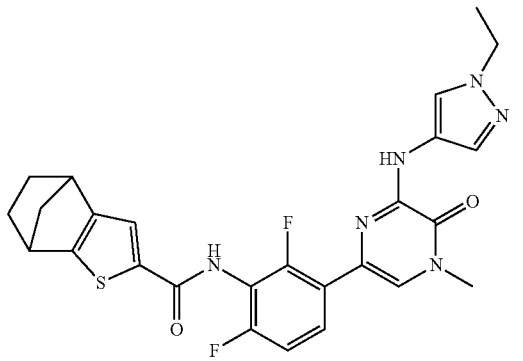 [SMILES: CCn1cc(Nc2nc(-c3ccc(F)c(NC(=O)c4cc5c(s4)C4CCC5C4)c3F)cn(C)c2=O)cn1] | N-(3-(6-(1-ethyl-1H-pyrazol-4-ylamino)-4-methyl-5-oxo-4,5-dihydropyrazin-2-yl)-2,6-difluorophenyl)-4,7-methano-4,5,6,7-tetrahydrobenzo[b]thiophene-2-carboxamide |

| Structure | Name |
|---|---|
| 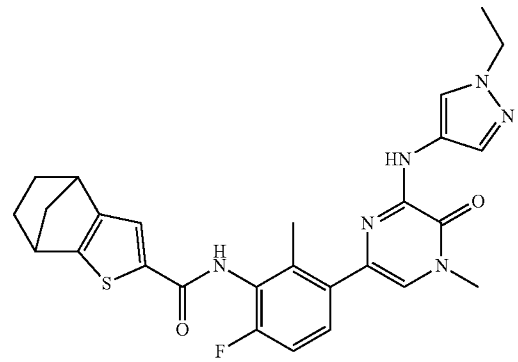 [SMILES: CCn1cc(Nc2nc(-c3ccc(F)c(NC(=O)c4cc5c(s4)C4CCC5C4)c3C)cn(C)c2=O)cn1] | N-(3-(6-(1-ethyl-1H-pyrazol-4-ylamino)-4-methyl-5-oxo-4,5-dihydropyrazin-2-yl)-6-fluoro-2-methylphenyl)-4,7-methano-4,5,6,7-tetrahydrobenzo[b]thiophene-2-carboxamide |
| 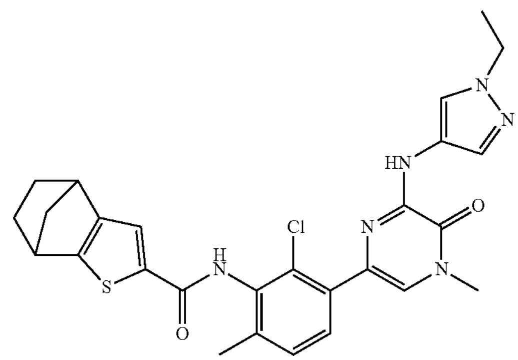 [SMILES: CCn1cc(Nc2nc(-c3ccc(C)c(NC(=O)c4cc5c(s4)C4CCC5C4)c3Cl)cn(C)c2=O)cn1] | N-(2-chloro-3-(6-(1-ethyl-1H-pyrazol-4-ylamino)-4-methyl-5-oxo-4,5-dihydropyrazin-2-yl)-6-methylphenyl)-4,7-methano-4,5,6,7-tetrahydrobenzo[b]thiophene-2-carboxamide |
| 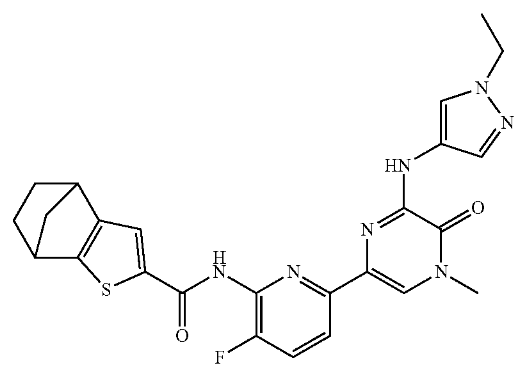 [SMILES: CCn1cc(Nc2nc(-c3ccc(F)c(NC(=O)c4cc5c(s4)C4CCC5C4)n3)cn(C)c2=O)cn1] | N-(6-(6-(1-ethyl-1H-pyrazol-4-ylamino)-4-methyl-5-oxo-4,5-dihydropyrazin-2-yl)-3-fluoropyridin-2-yl)-4,7-methano-4,5,6,7-tetrahydrobenzo[b]thiophene-2-carboxamide |
| 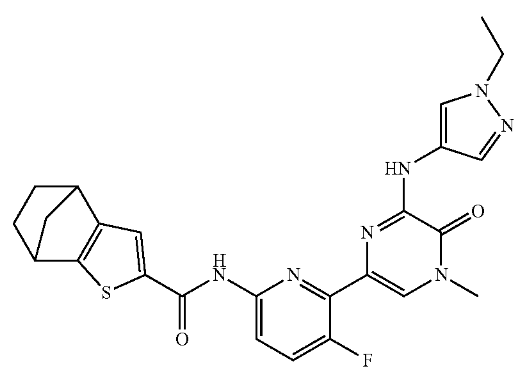 [SMILES: CCn1cc(Nc2nc(-c3nc(NC(=O)c4cc5c(s4)C4CCC5C4)ccc3F)cn(C)c2=O)cn1] | N-(6-(6-(1-ethyl-1H-pyrazol-4-ylamino)-4-methyl-5-oxo-4,5-dihydropyrazin-2-yl)-5-fluoropyridin-2-yl)-4,7-methano-4,5,6,7-tetrahydrobenzo[b]thiophene-2-carboxamide |

| Structure | Name |
|---|---|
| 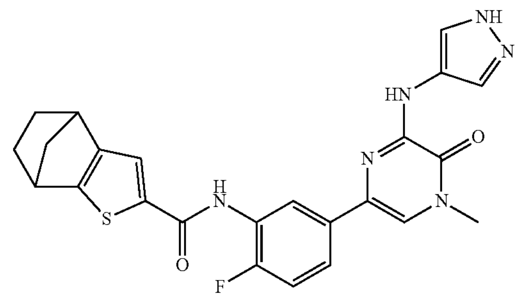 [SMILES: Cn1cc(-c2ccc(F)c(NC(=O)c3cc4c(s3)C3CCC4C3)c2)nc(Nc2cn[nH]c2)c1=O] | N-(5-(6-(1H-pyrazol-4-ylamino)-4-methyl-5-oxo-4,5-dihydropyrazin-2-yl)-2-fluorophenyl)-4,7-methano-4,5,6,7-tetrahydrobenzo[b]thiophene-2-carboxamide |
| 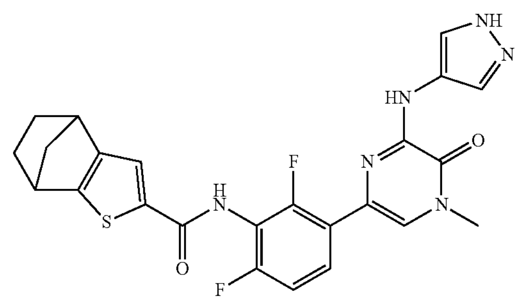 [SMILES: Cn1cc(-c2ccc(F)c(NC(=O)c3cc4c(s3)C3CCC4C3)c2F)nc(Nc2cn[nH]c2)c1=O] | N-(3-(6-(1H-pyrazol-4-ylamino)-4-methyl-5-oxo-4,5-dihydropyrazin-2-yl)-2,6-difluorophenyl)-4,7-methano-4,5,6,7-tetrahydrobenzo[b]thiophene-2-carboxamide |
| 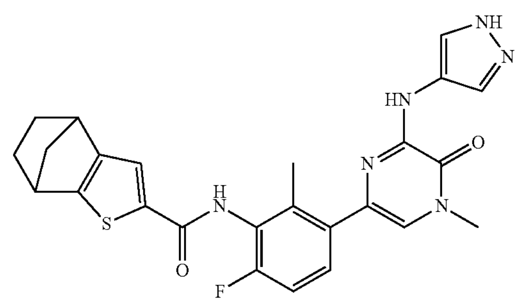 [SMILES: Cc1c(-c2cn(C)c(=O)c(Nc3cn[nH]c3)n2)ccc(F)c1NC(=O)c1cc2c(s1)C1CCC2C1] | N-(3-(6-(1H-pyrazol-4-ylamino)-4-methyl-5-oxo-4,5-dihydropyrazin-2-yl)-6-fluoro-2-methylphenyl)-4,7-methano-4,5,6,7-tetrahydrobenzo[b]thiophene-2-carboxamide |
| 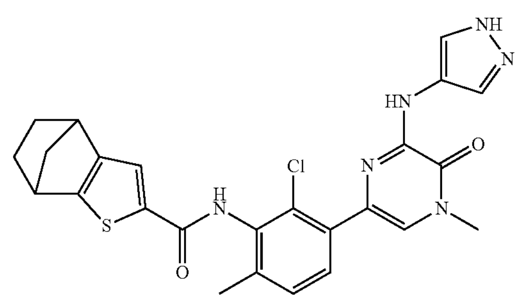 [SMILES: Cc1ccc(-c2cn(C)c(=O)c(Nc3cn[nH]c3)n2)c(Cl)c1NC(=O)c1cc2c(s1)C1CCC2C1] | N-(3-(6-(1H-pyrazol-4-ylamino)-4-methyl-5-oxo-4,5-dihydropyrazin-2-yl)-2-chloro-6-methylphenyl)-4,7-methano-4,5,6,7-tetrahydrobenzo[b]thiophene-2-carboxamide |
| 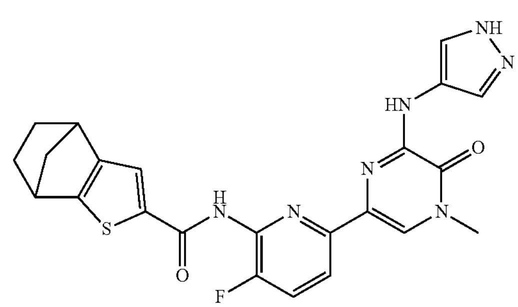 [SMILES: Cn1cc(-c2ccc(F)c(NC(=O)c3cc4c(s3)C3CCC4C3)n2)nc(Nc2cn[nH]c2)c1=O] | N-(6-(6-(1H-pyrazol-4-ylamino)-4-methyl-5-oxo-4,5-dihydropyrazin-2-yl)-3-fluoropyridin-2-yl)-4,7-methano-4,5,6,7-tetrahydrobenzo[b]thiophene-2-carboxamide |

| Structure | Name |
|---|---|
| 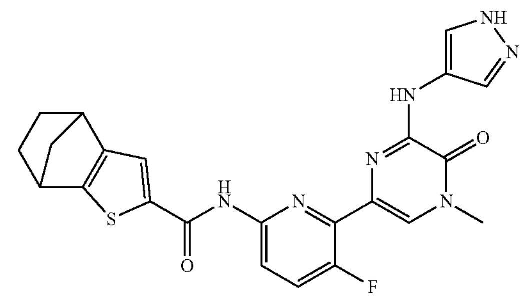 [SMILES: Cn1cc(-c2nc(NC(=O)c3cc4c(s3)C3CCC4C3)ccc2F)nc(Nc2cn[nH]c2)c1=O] | N-(6-(6-(1H-pyrazol-4-ylamino)-4-methyl-5-oxo-4,5-dihydropyrazin-2-yl)-5-fluoropyridin-2-yl)-4,7-methano-4,5,6,7-tetrahydrobenzo[b]thiophene-2-carboxamide |
| 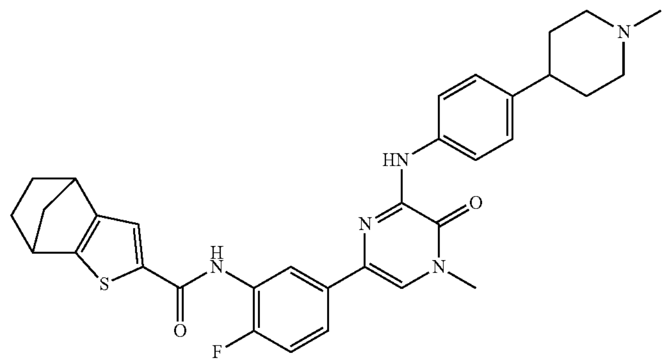 [SMILES: CN1CCC(c2ccc(Nc3nc(-c4ccc(F)c(NC(=O)c5cc6c(s5)C5CCC6C5)c4)cn(C)c3=O)cc2)CC1] | N-(2-fluoro-5-(4-methyl-6-(4-(1-methylpiperidin-4-yl)phenylamino)-5-oxo-4,5-dihydropyrazin-2-yl)phenyl)-4,7-methano-4,5,6,7-tetrahydrobenzo[b]thiophene-2-carboxamide |
| 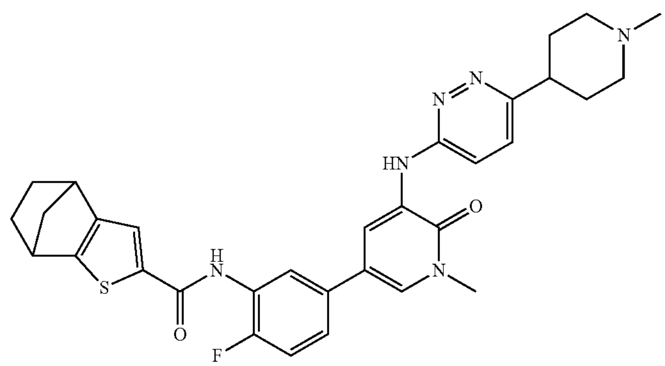 [SMILES: CN1CCC(c2ccc(Nc3cc(-c4ccc(F)c(NC(=O)c5cc6c(s5)C5CCC6C5)c4)cn(C)c3=O)nn2)CC1] | N-(2-fluoro-5-(1-methyl-5-(6-(1-methylpiperidin-4-yl)pyridazin-3-ylamino)-6-oxo-1,6-dihydropyridin-3-yl)phenyl)-4,7-methano-4,5,6,7-tetrahydrobenzo[b]thiophene-2-carboxamide |
| 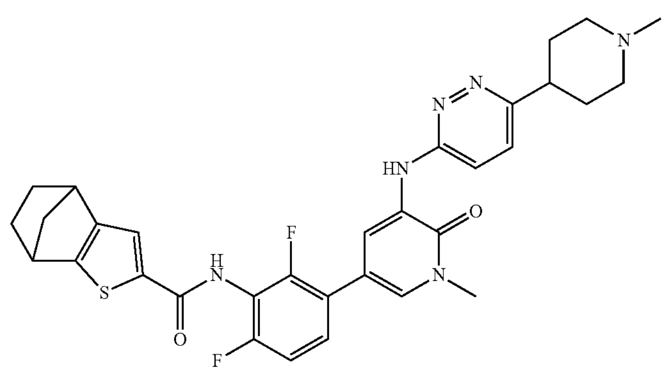 [SMILES: CN1CCC(c2ccc(Nc3cc(-c4ccc(F)c(NC(=O)c5cc6c(s5)C5CCC6C5)c4F)cn(C)c3=O)nn2)CC1] | N-(2,6-difluoro-3-(1-meth-5-(6-(1-methylpiperidin-4-yl)pyridazin-3-ylamino)-6-oxo-1,6-dihydropyridin-3-yl)phenyl)-4,7-methano-4,5,6,7-tetrahydrobenzo[b]thiophene-2-carboxamide |

| Structure | Name |
|---|---|
| 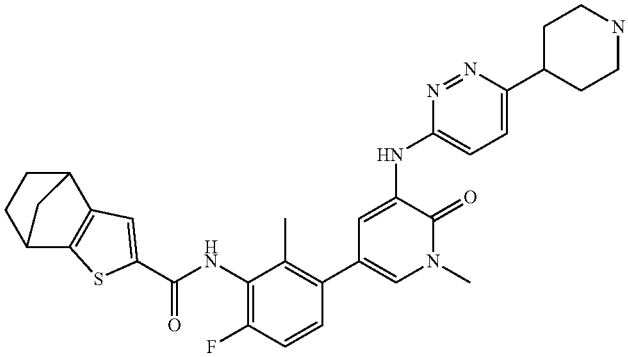 | N-(6-fluoro-2-meth-3-(1-methyl-5-(6-(1-methylpiperidin-4-yl)pyridazin-3-ylamino)-6-oxo-1,6-dihydropyridin-3-yl)phenyl)-4,7-methano-4,5,6,7-tetrahydrobenzo[b]thiophene-2-carboxamide |
| 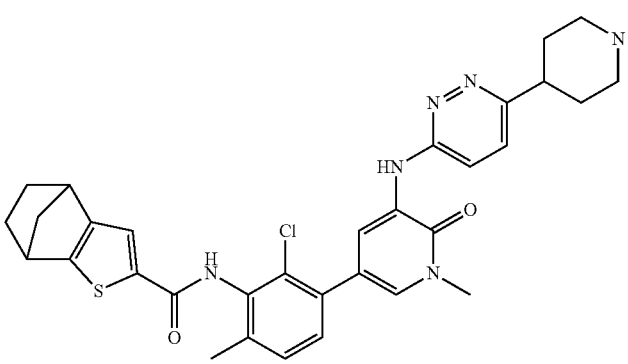 | N-(2-chloro-6-methyl-3-(1-methyl-5-(6-(1-methylpiperidin-4-yl)pyridazin-3-ylamino)-6-oxo-1,6-dihydropyridin-3-yl)phenyl)-4,7-methano-4,5,6,7-tetrahydrobenzo[b]thiophene-2-carboxamide |
| 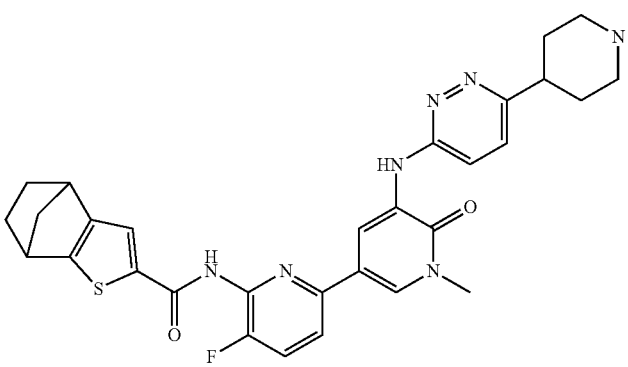 | N-(3-fluoro-6-(1-methyl-5-(6-(1-methylpiperidin-4-yl)pyridazin-3-ylamino)-6-oxo-1,6-dihydropyridin-3-yl)pyridin-2-yl)-4,7-methano-4,5,6,7-tetrahydrobenzo[b]thiophene-2-carboxamide |
| 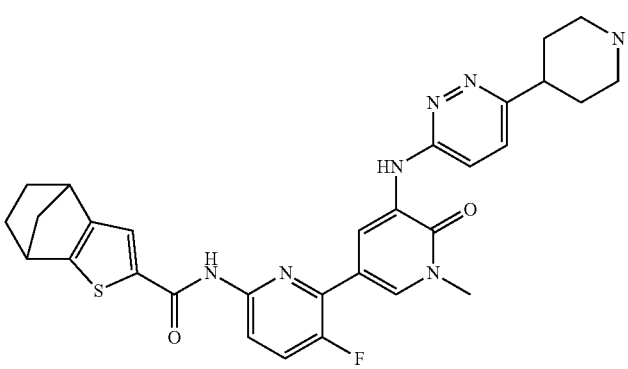 | N-(5-fluoro-6-(1-methyl-5-(6-(1-methylpiperidin-4-yl)pyridazin-3-ylamino)-6-oxo-1,6-dihydropyridin-3-yl)pyridin-2-yl)-4,7-methano-4,5,6,7-tetrahydrobenzo[b]thiophene-2-carboxamide |

| Structure | Name |
|---|---|
| 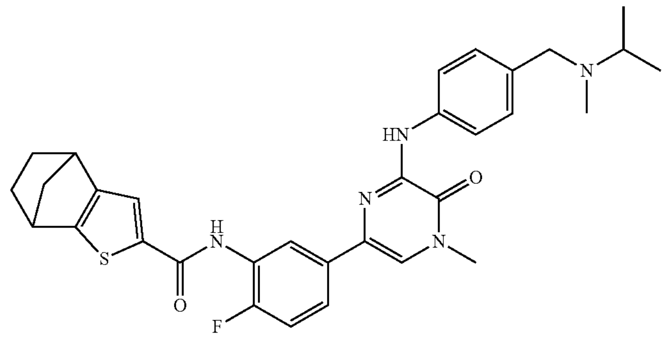 [SMILES: CC(C)N(C)Cc1ccc(Nc2nc(-c3ccc(F)c(NC(=O)c4cc5c(s4)C4CCC5C4)c3)cn(C)c2=O)cc1] | N-(2-fluoro-5-(6-(4-((isopropyl(methyl)amino)methyl)phenylamino)-4-methyl-5-oxo-4,5-dihydropyrazin-2-yl)phenyl)-4,7-methano-4,5,6,7-tetrahydrobenzo[b]thiophene-2-carboxamide |
| 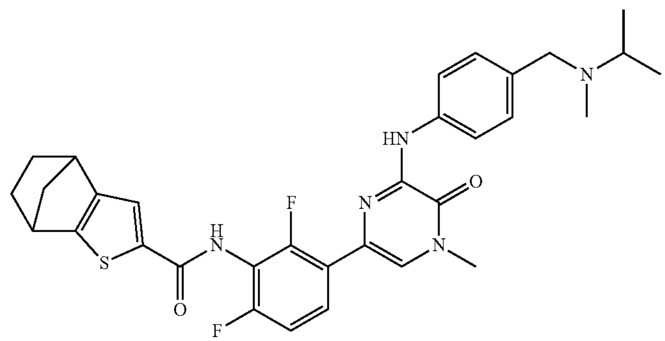 [SMILES: CC(C)N(C)Cc1ccc(Nc2nc(-c3ccc(F)c(NC(=O)c4cc5c(s4)C4CCC5C4)c3F)cn(C)c2=O)cc1] | N-(2,6-difluoro-3-(6-(4-((isopropyl(methyl)amino)methyl)phenylamino)-4-methyl-5-oxo-4,5-dihydropyrazin-2-yl)phenyl)-4,7-methano-4,5,6,7-tetrahydrobenzo[b]thiophene-2-carboxamide |
| 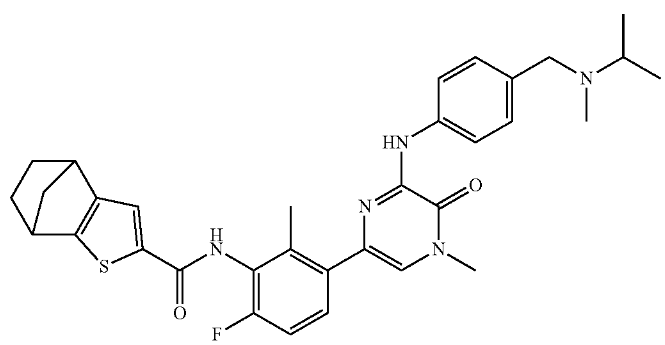 [SMILES: Cc1c(-c2cn(C)c(=O)c(Nc3ccc(CN(C)C(C)C)cc3)n2)ccc(F)c1NC(=O)c1cc2c(s1)C1CCC2C1] | N-(6-fluoro-3-(6-(4-((isopropyl(methyl)amino)methyl)phenylamino)-4-methyl-5-oxo-4,5-dihydropyrazin-2-yl)-2-methylphenyl)-4,7-methano-4,5,6,7-tetrahydrobenzo[b]thiophene-2-carboxamide |
| 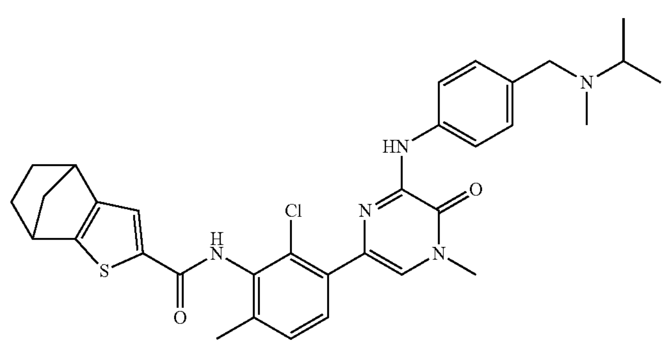 [SMILES: Cc1ccc(-c2cn(C)c(=O)c(Nc3ccc(CN(C)C(C)C)cc3)n2)c(Cl)c1NC(=O)c1cc2c(s1)C1CCC2C1] | N-(2-chloro-3-(6-(4-((isopropyl(methyl)amino)methyl)phenylamino)-4-methyl-5-oxo-4,5-dihydropyrazin-2-yl)-6-methylphenyl)-4,7-methano-4,5,6,7-tetrahydrobenzo[b]thiophene-2-carboxamide |

| Structure | Name |
|---|---|
| 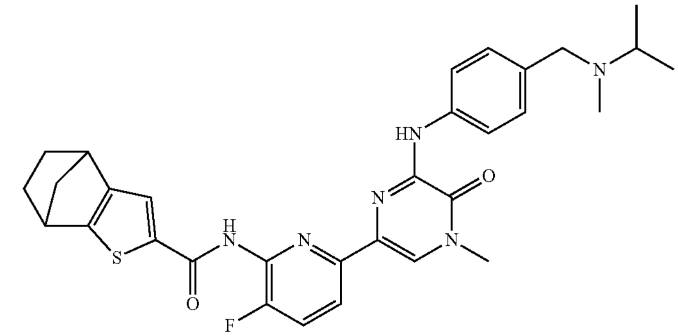 [SMILES: CC(C)N(C)Cc1ccc(Nc2nc(-c3ccc(F)c(NC(=O)c4cc5c(s4)C4CCC5C4)n3)cn(C)c2=O)cc1] | N-(3-fluoro-6-(6-(4-((isopropyl(methyl)amino)methyl)phenylamino)-4-methyl-5-oxo-4,5-dihydropyrazin-2-yl)pyridin-2-yl)-4,7-methano-4,5,6,7-tetrahydrobenzo[b]thiophene-2-carboxamide |
| 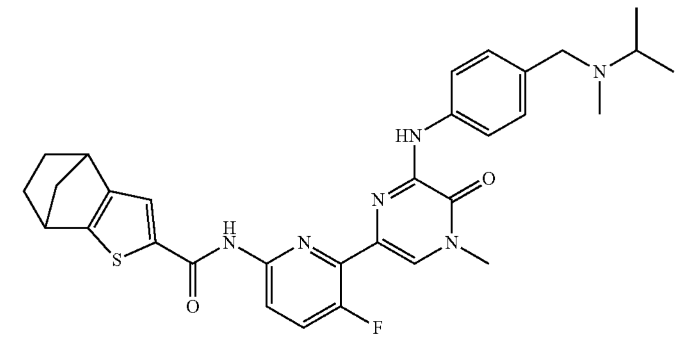 [SMILES: CC(C)N(C)Cc1ccc(Nc2nc(-c3nc(NC(=O)c4cc5c(s4)C4CCC5C4)ccc3F)cn(C)c2=O)cc1] | N-(5-fluoro-6-(6-(4-((isopropyl(methyl)amino)methyl)phenylamino)-4-methyl-5-oxo-4,5-dihydropyrazin-2-yl)pyridin-2-yl)-4,7-methano-4,5,6,7-tetrahydrobenzo[b]thiophene-2-carboxamide |
| 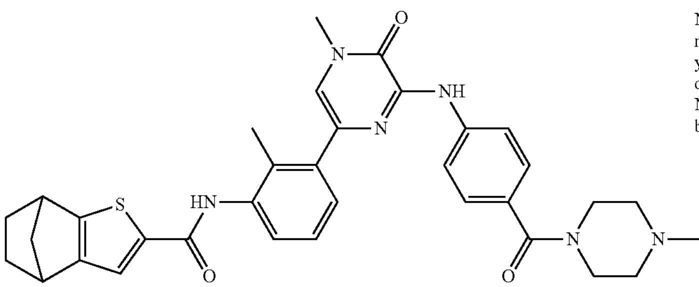 [SMILES: Cc1c(NC(=O)c2cc3c(s2)C2CCC3C2)cccc1-c1cn(C)c(=O)c(Nc2ccc(C(=O)N3CCN(C)CC3)cc2)n1] | N-{2-methyl-3-[4-methyl-6-({4-[(4-methylpiperazin-1-yl)carbonyl]phenyl}amino)-5-oxo-4,5-dihydropyrazin-2-yl]phenyl}-4,7-N-methano-4,5,6,7-tetrahydro-1-benzothiophene-2-carboxamide |
| 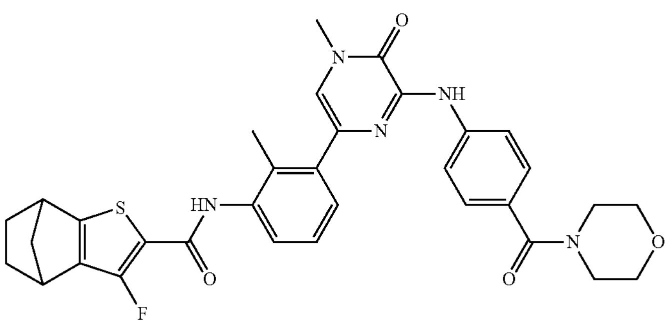 [SMILES: Cc1c(NC(=O)c2sc3c(c2F)C2CCC3C2)cccc1-c1cn(C)c(=O)c(Nc2ccc(C(=O)N3CCOCC3)cc2)n1] | 3-fluoro-N-[2-methyl-3-(4-methyl-6-{[4-(morpholin-4-ylcarbonyl)phenyl]amino}-5-oxo-4,5-dihydropyrazin-2-yl)phenyl]-4,7-methano-4,5,6,7-tetrahydro-1-benzothiophene-2-carboxamide |
| 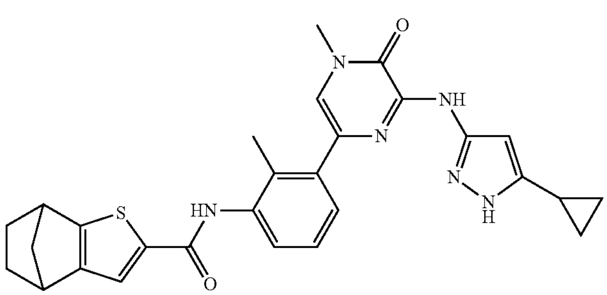 [SMILES: Cc1c(NC(=O)c2cc3c(s2)C2CCC3C2)cccc1-c1cn(C)c(=O)c(Nc2cc(C3CC3)[nH]n2)n1] | N-(3-{5-[(5-cyclopropyl-1H-pyrazol-3-yl)amino]-1-methyl-6-oxo-1,6-dihydropyridin-3-yl}-2-methylphenyl)-4,7-methano-4,5,6,7-tetrahydro-1-benzothiophene-2-carboxamide |

| Structure | Name |
|---|---|
| 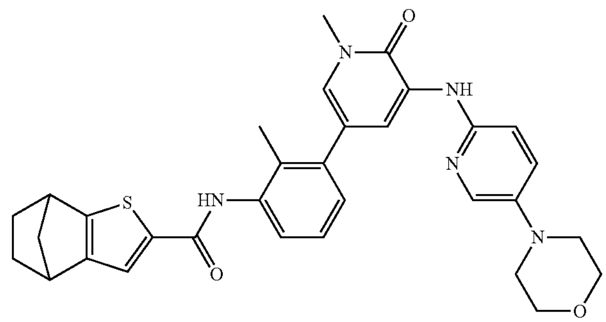 [SMILES: Cc1c(NC(=O)c2cc3c(s2)C2CCC3C2)cccc1-c1cc(Nc2ccc(N3CCOCC3)cn2)c(=O)n(C)c1] | N-[2-methyl-3-(1-methyl-5-{[5-(morpholin-4-yl)pyridin-2-yl]amino}-6-oxo-1,6-dihydropyridin-3-yl)phenyl]-4,7-methano-4,5,6,7-tetrahydro-1-benzothiophene-2-carboxamide |
| 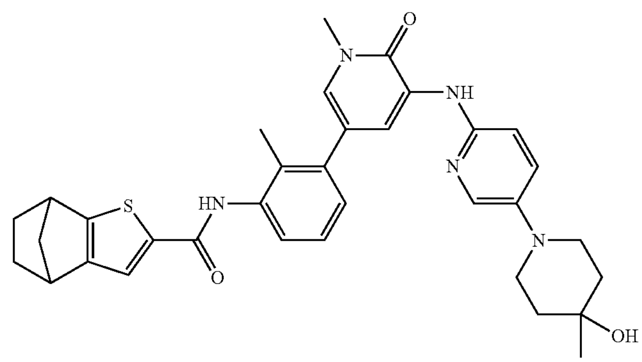 [SMILES: Cc1c(NC(=O)c2cc3c(s2)C2CCC3C2)cccc1-c1cc(Nc2ccc(N3CCC(C)(O)CC3)cn2)c(=O)n(C)c1] | N-[3-(5-{[5-(4-hydroxy-4-methylpiperidin-1-yl)pyridin-2-yl]amino}-1-methyl-6-oxo-1,6-dihydropyridin-3-yl)-2-methylphenyl]-4,7-methano-4,5,6,7-tetrahydro-1-benzothiophene-2-carboxamide |
| 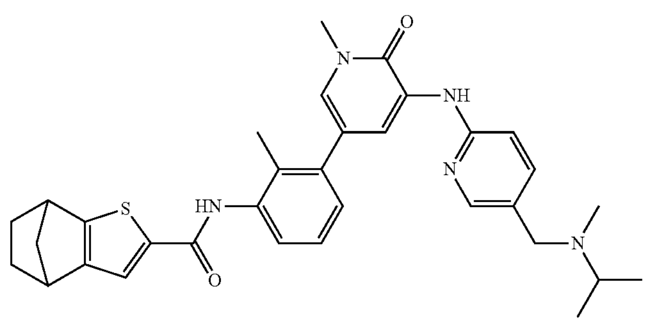 [SMILES: Cc1c(NC(=O)c2cc3c(s2)C2CCC3C2)cccc1-c1cc(Nc2ccc(CN(C)C(C)C)cn2)c(=O)n(C)c1] | N-(3-(5-(5-((isopropyl(methyl)amino)methyl)pyridin-2-ylamino)-1-methyl-6-oxo-1,6-dihydropyridin-3-yl)-2-methylphenyl)-4,7-methano-4,5,6,7-tetrahydrobenzo[b]thiophene-2-carboxamide |
| 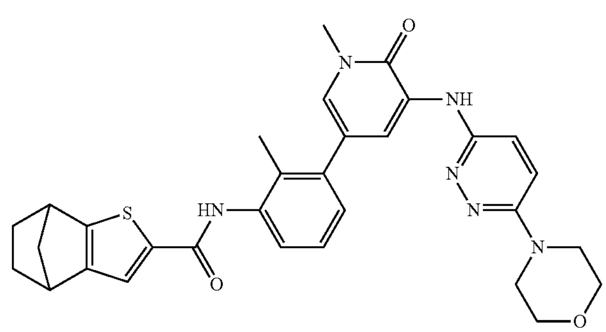 [SMILES: Cc1c(NC(=O)c2cc3c(s2)C2CCC3C2)cccc1-c1cc(Nc2ccc(N3CCOCC3)nn2)c(=O)n(C)c1] | N-[2-methyl-3-(1-methyl-5-{[6-(morpholin-4-yl)pyridazin-3-yl]amino}-6-oxo-1,6-dihydropyridin-3-yl)phenyl]-4,7-methano-4,5,6,7-tetrahydro-1-benzothiophene-2-carboxamide |

| Structure | Name |
|---|---|
| 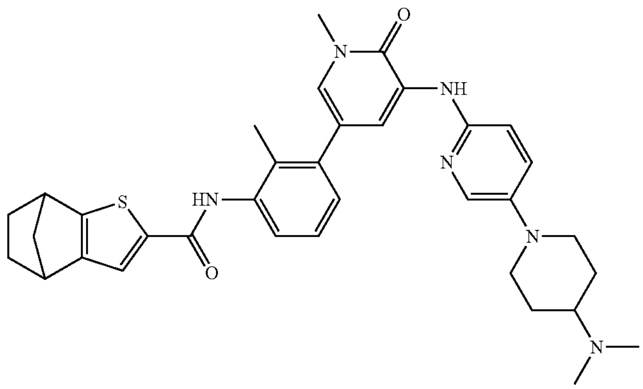 [SMILES: Cc1c(NC(=O)c2cc3c(s2)C2CCC3C2)cccc1-c1cc(Nc2ccc(N3CCC(N(C)C)CC3)cn2)c(=O)n(C)c1] | N-{3-[5-([5-[4-(dimethylamino)piperidin-1-yl]pyridin-2-yl}amino)-1-methyl-6-oxo-1,6-dihydropyridin-3-yl]-2-methylphenyl}-4,7-methano-4,5,6,7-tetrahydro-1-benzothiophene-2-carboxamide |
| 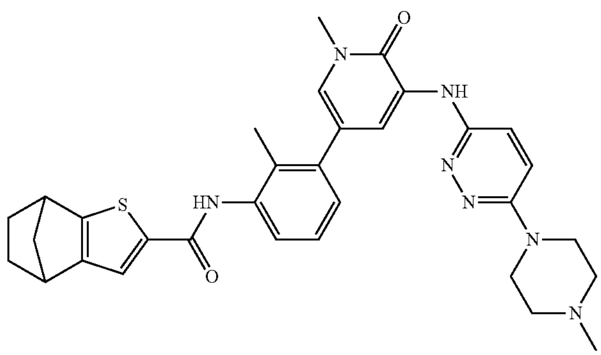 [SMILES: Cc1c(NC(=O)c2cc3c(s2)C2CCC3C2)cccc1-c1cc(Nc2ccc(N3CCN(C)CC3)nn2)c(=O)n(C)c1] | N-[2-methyl-3-(1-methyl-5-{[6-(4-methylpiperazin-1-yl)pyridazin-3-yl]amino}-6-oxo-1,6-dihydropyridin-3-yl)phenyl]-4,7-methano-4,5,6,7-tetrahydro-1-benzothiophene-2-carboxamide |
| 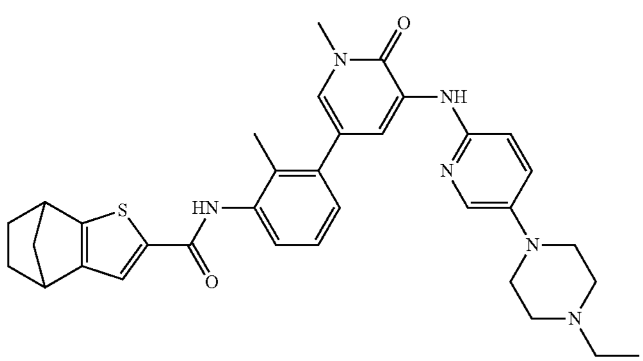 [SMILES: CCN1CCN(c2ccc(Nc3cc(-c4cccc(NC(=O)c5cc6c(s5)C5CCC6C5)c4C)cn(C)c3=O)nc2)CC1] | N-[3-(5-{[5-(4-ethylpiperazin-1-yl)pyridin-2-yl]amino}-1-methyl-6-oxo-1,6-dihydropyridin-3-yl)-2-methylphenyl]-4,7-methano-4,5,6,7-tetrahydro-1-benzothiophene-2-carboxamide |
| 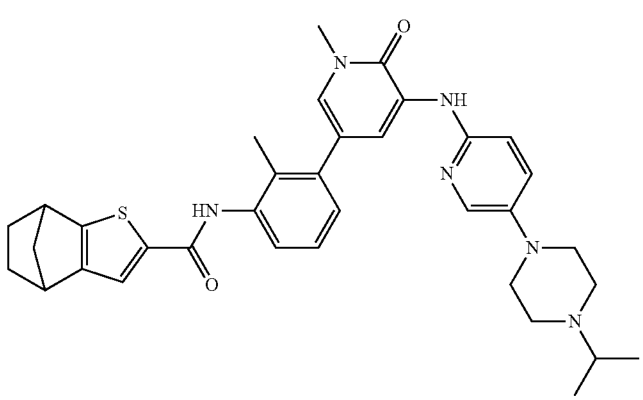 [SMILES: Cc1c(NC(=O)c2cc3c(s2)C2CCC3C2)cccc1-c1cc(Nc2ccc(N3CCN(C(C)C)CC3)cn2)c(=O)n(C)c1] | N-{2-methyl-3-[1-methyl-6-oxo-5-({5-[4-(propan-2-yl)piperazin-1-yl]pyridin-2-yl}amino)-1,6-dihydropyridin-3-yl]phenyl}-4,7-methano-4,5,6,7-tetrahydro-1-benzothiophene-2-carboxamide |

| Structure | Name |
|---|---|
| 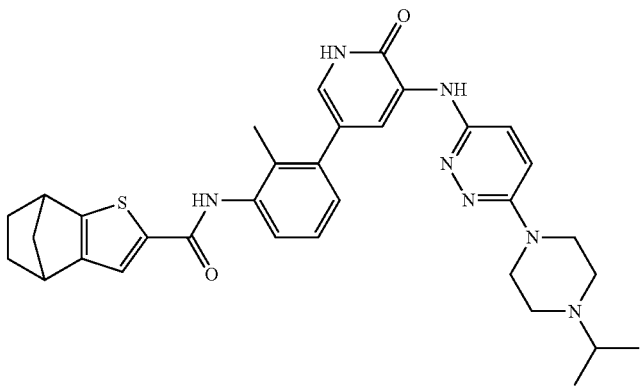 [SMILES: Cc1c(NC(=O)c2cc3c(s2)C2CCC3C2)cccc1-c1c[nH]c(=O)c(Nc2ccc(N3CCN(C(C)C)CC3)nn2)c1] | N-[2-methyl-3-(5-{[6-(4-methylpiperazin-1-yl)pyridazin-3-yl]amino}-6-oxo-1,6-dihydropyridin-3-yl)phenyl]-4,7-methano-4,5,6,7-tetrahydro-1-benzothiophene-2-carboxamide |
| 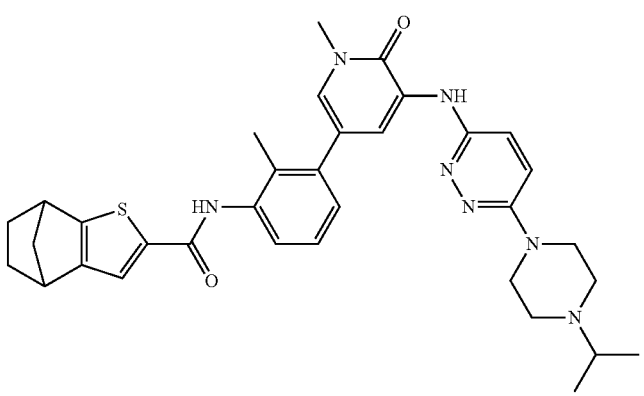 [SMILES: Cc1c(NC(=O)c2cc3c(s2)C2CCC3C2)cccc1-c1cc(Nc2ccc(N3CCN(C(C)C)CC3)nn2)c(=O)n(C)c1] | N-{2-methyl-3-[1-methyl-6-oxo-5-({6-[4-(propan-2-yl)piperazin-1-yl]pyridazin-3-yl}amino)-1,6-dihydropyridin-3-yl]phenyl}-4,7-methano-4,5,6,7-tetrahydro-1-benzothiophene-2-carboxamide |
| 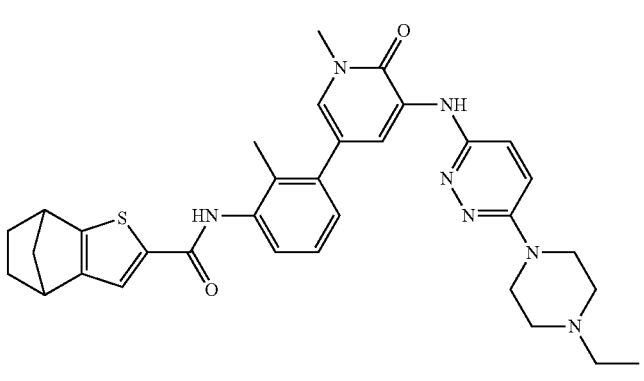 [SMILES: CCN1CCN(c2ccc(Nc3cc(-c4cccc(NC(=O)c5cc6c(s5)C5CCC6C5)c4C)cn(C)c3=O)nn2)CC1] | N-[3-(5-{[6-(4-ethylpiperazin-1-yl)pyridazin-3-yl]amino}-1-methyl-6-oxo-1,6-dihydropyridin-3-yl)-2-methylphenyl]-4,7-methano-4,5,6,7-tetrahydro-1-benzothiophene-2-carboxamide |
| 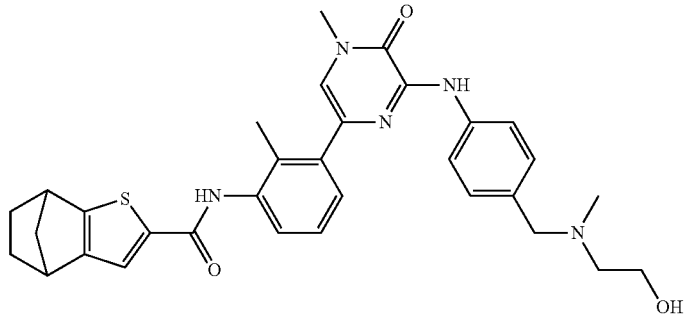 [SMILES: Cc1c(NC(=O)c2cc3c(s2)C2CCC3C2)cccc1-c1cn(C)c(=O)c(Nc2ccc(CN(C)CCO)cc2)n1] | N-(3-{6-[(4-{[(2-hydroxyethyl)(methyl)amino]methyl}phenyl)amino]-4-methyl-5-oxo-4,5-dihydropyrazin-2-yl}-2-methylphenyl)-4,7-methano-4,5,6,7-tetrahydro-1-benzothiophene-2-carboxamide |

| Structure | Name |
|---|---|
| 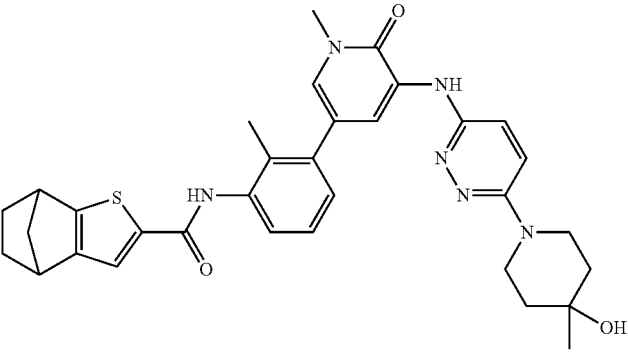 [SMILES: Cc1c(NC(=O)c2cc3c(s2)C2CCC3C2)cccc1-c1cc(Nc2ccc(N3CCC(C)(O)CC3)nn2)c(=O)n(C)c1] | N-[3-(5-{[6-(4-hydroxy-4-methylpiperidin-1-yl)pyridazin-3-yl]amino}-1-methyl-6-oxo-1,6-dihydropyridin-3-yl)-2-methylphenyl]-4,7-methano-4,5,6,7-tetrahydro-1-benzothiophene-2-carboxamide |
| 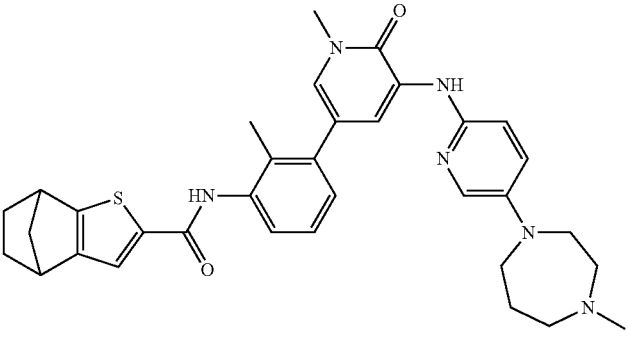 [SMILES: Cc1c(NC(=O)c2cc3c(s2)C2CCC3C2)cccc1-c1cc(Nc2ccc(N3CCCN(C)CC3)cn2)c(=O)n(C)c1] | N-[2-methyl-3-(1-methyl-5-{[5-[4-methyl-1,4-diazepan-1-yl)pyridin-2-yl]amino}-6-oxo-1,6-dihydropyridin-3-yl)phenyl]-4,7-methano-4,5,6,7-tetrahydro-1-benzothiophene-2-carboxamide |
| 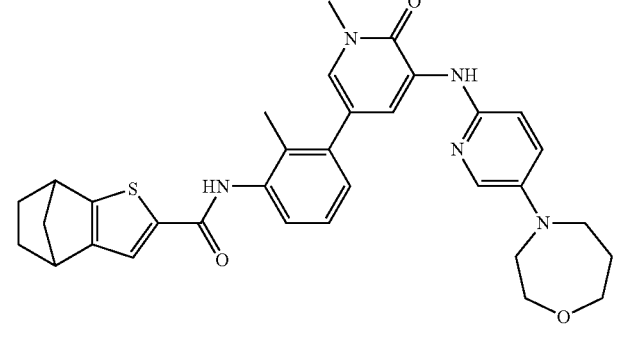 [SMILES: Cc1c(NC(=O)c2cc3c(s2)C2CCC3C2)cccc1-c1cc(Nc2ccc(N3CCCOCC3)cn2)c(=O)n(C)c1] | N-[2-methyl-3-(1-methyl-5-{[5-(1,4-oxazepan-4-yl)pyridin-2-yl]amino}-6-oxo-1,6-dihydropyridin-3-yl)phenyl]-4,7-methano-4,5,6,7-tetrahydro-1-benzothiophene-2-carboxamide |
| 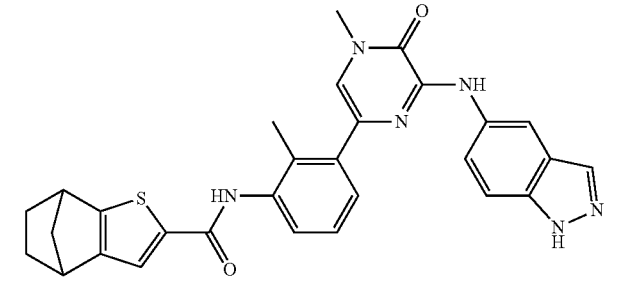 [SMILES: Cc1c(NC(=O)c2cc3c(s2)C2CCC3C2)cccc1-c1cn(C)c(=O)c(Nc2ccc3[nH]ncc3c2)n1] | N-{3-[6-(1H-indazol-5-ylamino)-4-methyl-5-oxo-4,5-dihydropyrazin-2-yl]-2-methylphenyl}-4,7-methano-4,5,6,7-tetrahydro-1-benzothiophene-2-carboxamide |

| Structure | Name |
|---|---|
| 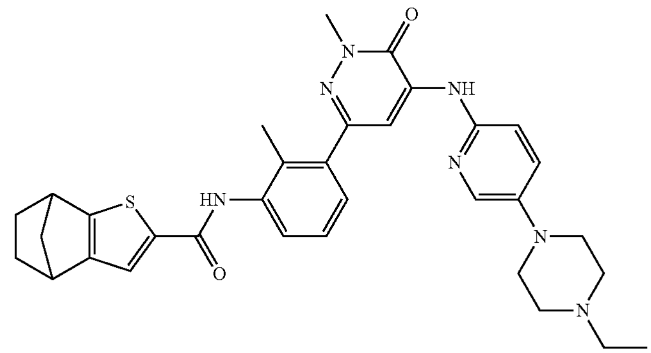 [SMILES: CCN1CCN(c2ccc(Nc3cc(-c4cccc(NC(=O)c5cc6c(s5)C5CCC6C5)c4C)nn(C)c3=O)nc2)CC1] | N-[3-(5-{[5-(4-ethylpiperazin-1-yl)pyridin-2-yl]amino}-1-methyl-6-oxo-1,6-dihydropyridazin-3-yl)-2-methylphenyl]-4,7-methano-4,5,6,7-tetrahydro-1-benzothiophene-2-carboxamide |
| 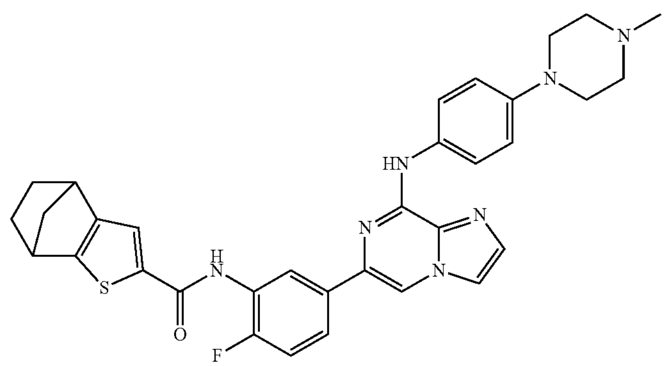 [SMILES: CN1CCN(c2ccc(Nc3nc(-c4ccc(F)c(NC(=O)c5cc6c(s5)C5CCC6C5)c4)cn4ccnc34)cc2)CC1] | N-(2-fluoro-5-(8-(4-(4-methylpiperazin-1-yl)phenylamino)imidazo[1,2-a]pyrazin-6-yl)phenyl)-4,7-methano-4,5,6,7-tetrahydrobenzo[b]thiophene-2-carboxamide |
| 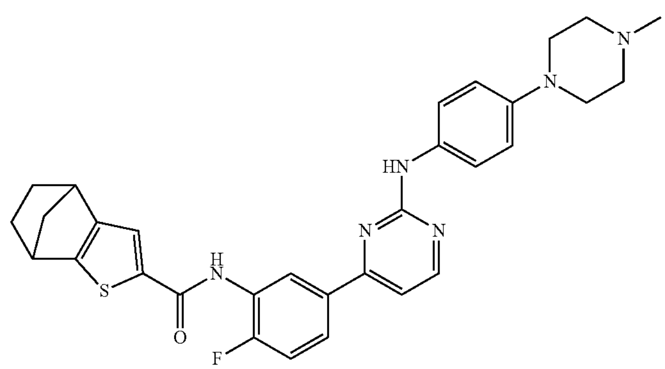 [SMILES: CN1CCN(c2ccc(Nc3nccc(-c4ccc(F)c(NC(=O)c5cc6c(s5)C5CCC6C5)c4)n3)cc2)CC1] | N-(2-fluoro-5-(2-(4-(4-methylpiperazin-1-yl)phenylamino)pyrimidin-4-yl)phenyl)-4,7-methano-4,5,6,7-tetrahydrobenzo[b]thiophene-2-carboxamide |
| 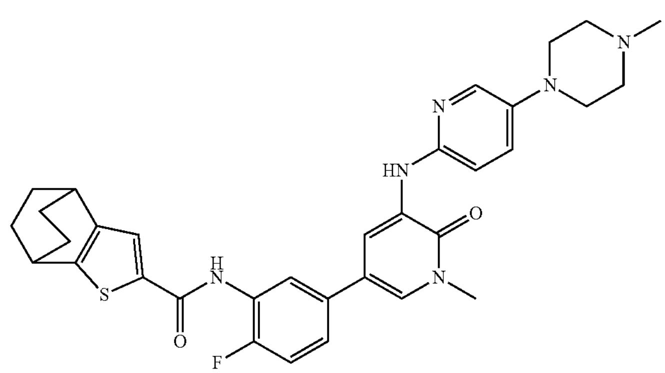 [SMILES: CN1CCN(c2ccc(Nc3cc(-c4ccc(F)c(NC(=O)c5cc6c(s5)C5CCC6CC5)c4)cn(C)c3=O)nc2)CC1] | N-(2-fluoro-5-(1-methyl-5-(5-(4-methylpiperazin-1-yl)pyridin-2-ylamino)-6-oxo-1,6-dihydropyridin-3-yl)phenyl)-4,7-ethano-4,5,6,7-tetrahydrobenzo[b]thiophene-2-carboxamide |

| Structure | Name |
|---|---|
| 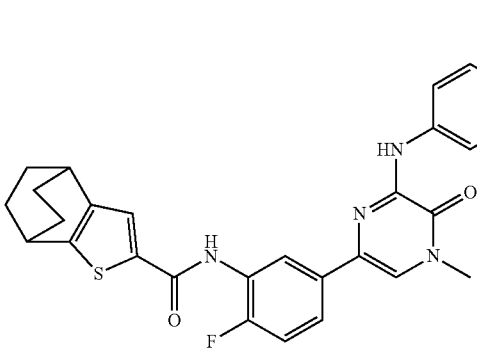 | N-(2-fluoro-5-(4-methyl-6-(4-(4-methylpiperazin-1-yl)phenylamino)-5-oxo-4,5-dihydropyrazin-2-yl)phenyl)-4,7-ethano-4,5,6,7-tetrahydrobenzo[b]thiophene-2-carboxamide |
| 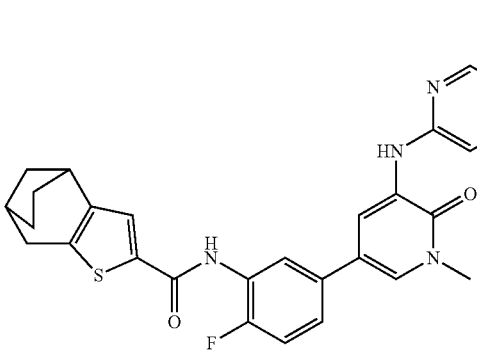 | N-(2-fluoro-5-(1-methyl-5-(5-(4-methylpiperazin-1-yl)pyridin-2-ylamino)-6-oxo-1,6-dihydropyridin-3-yl)phenyl)-4,6-ethano-4,5,6,7-tetrahydrobenzo[b]thiophene-2-carboxamide |
| 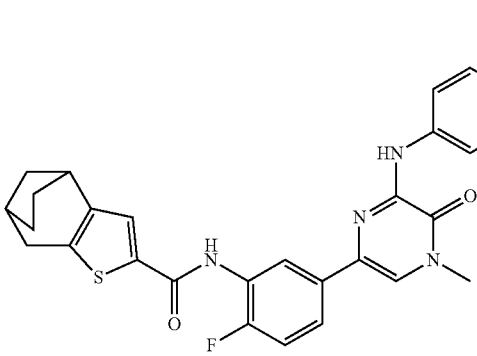 | N-(2-fluoro-5-(4-methyl-6-(4-(4-methylpiperazin-1-yl)phenylamino)-5-oxo-4,5-dihydropyrazin-2-yl)phenyl)-4,6-ethano-4,5,6,7-tetrahydrobenzo[b]thiophene-2-carboxamide |
| 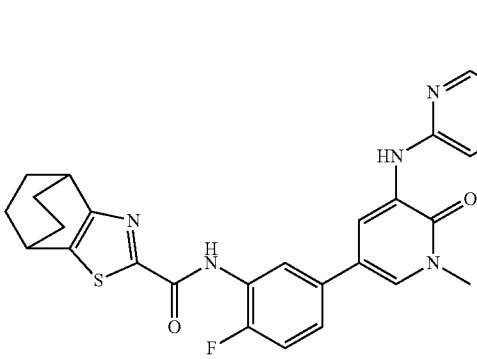 | N-(2-fluoro-5-(1-methyl-5-(5-(4-methylpiperazin-1-yl)pyridin-2-ylamino)-6-oxo-1,6-dihydropyridin-3-yl)phenyl)-4,7-ethano-4,5,6,7-tetrahydrobenzo[d]thiazole-2-carboxamide |

-continued

| Structure | Name |
|---|---|
| 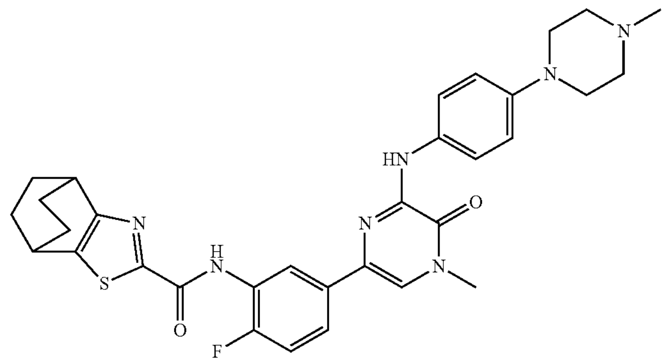 [SMILES: CN1CCN(c2ccc(Nc3nc(-c4ccc(F)c(NC(=O)c5nc6c(s5)C5CCC6CC5)c4)cn(C)c3=O)cc2)CC1] | N-(2-fluoro-5-(4-methyl-6-(4-(4-methylpiperazin-1-yl)phenylamino)-5-oxo-4,5-dihydropyrazin-2-yl)phenyl)-4,7-ethano-4,5,6,7-tetrahydrobenzo[d]thiazole-2-carboxamide |
| 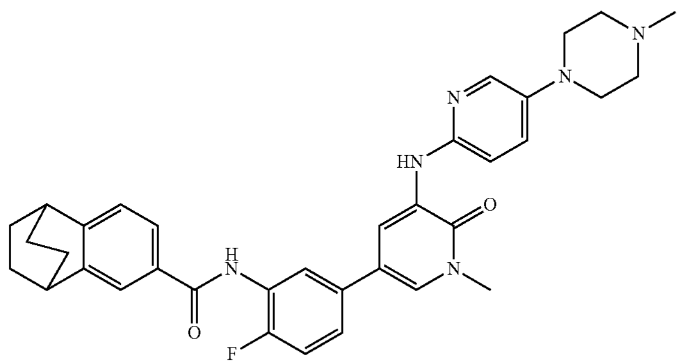 [SMILES: CN1CCN(c2ccc(Nc3cc(-c4ccc(F)c(NC(=O)c5ccc6c(c5)C5CCC6CC5)c4)cn(C)c3=O)nc2)CC1] | N-(2-fluoro-5-(1-methyl-5-(5-(4-methylpiperazin-1-yl)pyridin-2-ylamino)-6-oxo-1,6-dihydropyridin-3-yl)phenyl)-5,8-ethano-5,6,7,8-tetrahydronaphthalene-2-carboxamide |
| 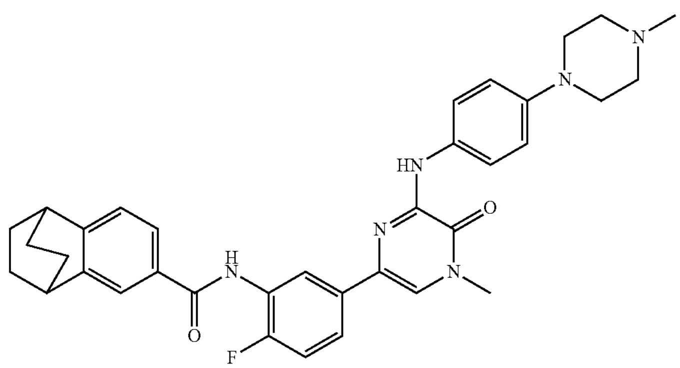 [SMILES: CN1CCN(c2ccc(Nc3nc(-c4ccc(F)c(NC(=O)c5ccc6c(c5)C5CCC6CC5)c4)cn(C)c3=O)cc2)CC1] | N-(2-fluoro-5-(4-methyl-6-(4-(4-methylpiperazin-1-yl)phenylamino)-5-oxo-4,5-dihydropyrazin-2-yl)phenyl)-5,8-ethano-5,6,7,8-tetrahydronaphthalene-2-carboxamide |

EXAMPLE 4

Biochemical Btk Assay

A generalized procedure for one standard biochemical Btk Kinase Assay that can be used to test compounds disclosed in this application is as follows.

A master mix minus Btk enzyme is prepared containing 1X Cell Signaling kinase buffer (25 mM Tris-HCl, pH 7.5, 5 mM beta-glycerophosphate, 2 mM dithiothreitol, 0.1 mM $Na_3VO_4$, 10 mM $MgCl_2$), 0.5 µM Promega PTK Biotinylated peptide substrate 2, and 0.01% BSA. A master mix plus Btk enzyme is prepared containing 1× Cell Signaling kinase buffer, 0.5 µM PTK Biotinylated peptide substrate 2, 0.01% BSA, and 100 ng/well (0.06 mU/well) Btk enzyme. Btk enzyme is prepared as follows: full length human wildtype Btk (accession number NM-000061) with a C-terminal V5 and 6×His tag was subcloned into pFastBac vector for making baculovirus carrying this epitope-tagged Btk. Generation of baculovirus is done based on Invitrogen's instructions detailed in its published protocol "Bac-toBac Baculovirus Expression Systems" (Cat. Nos. 10359-016 and 10608-016). Passage 3 virus is used to infect Sf9 cells to overexpress the recombinant Btk protein. The Btk protein is then purified to homogeneity using Ni-NTA column. The purity of the final protein preparation is greater than 95% based on the sensitive Sypro-Ruby staining. A solution of 200 µM ATP is prepared in water and adjusted to pH7.4 with 1N NaOH. A quantity of 1.25 µL of compounds in 5% DMSO is transferred to a 96-well ½ area Costar polystyrene plate Compounds are tested singly and with an 11-point dose-responsive curve (starting concentration is 10 µM; 1:2 dilution). A quantity of 18.75 µL of master mix minus enzyme (as a negative control) and master mix plus enzyme is transferred to appropriate wells in 96-well ½ area costar polystyrene plate. 5 µL of 200 µM ATP is added to that mixture in the 96-well ½ area Costar polystyrene plate for final ATP concentration of 40 µM. The reaction is allowed to incubate for 1 hour at room temperature. The reaction is stopped with Perkin Elmer 1X detection buffer containing 30 mM EDTA, 20 nM SA-APC, and 1 nM PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated. Alternatively, the Lanthascreen assay can be used to evaluate Btk activity through quantification of its phosphorylated peptide product. The FRET that occurs between the flourescein on the peptide product and the terbium on the detection antibody decreases with the addition of inhibitors of Btk that reduce the phosphorylation of the peptide. In a final reaction volume of 25 uL, Btk (h) (0.1 ng/25 ul reaction) is incubated with 50 mM Hepes pH 7.5, 10 mM $MgCl_2$, 2 mM $MnCl_2$, 2 mM DTT, 0.2 mM $NaVO_4$, 0.01% BSA, and 0.4 uM fluorescein poly-GAT. The reaction is initiated by the addition of ATP to 25 uM (Km of ATP). After incubation for 60 minutes at room temperature, the reaction is stopped by the addition of a final concentration of 2 nM Tb-PY20 detection antibody in 60 mM EDTA for 30 minutes at room temperature. Detection is determined on a Perkin Elmer Envision with 340 nM excitation and emission at 495 and 520 nm.

EXAMPLE 5

Ramos Cell Btk Assay

Another generalized procedure for a standard cellular Btk Kinase Assay that can be used to test compounds disclosed in this application is as follows.

Ramos cells are incubated at a density of $0.5 \times 10^7$ cells/ml in the presence of test compound for 1 hr at 37° C. Cells are then stimulated by incubating with 10 µg/ml anti-human IgM $F(ab)_2$ for 5 minutes at 37° C. Cells are pelleted, lysed, and a protein assay is performed on the cleared lysate. Equal protein amounts of each sample are subject to SDS-PAGE and western blotting with either anti-phosphoBtk (Tyr223) antibody (Cell Signaling Technology #3531) or phosphoBtk (Tyr551) antibody (BD Transduction Labs #558034) to assess Btk autophosphorylation or an anti-Btk antibody (BD Transduction Labs #611116) to control for total amounts of Btk in each lysate.

EXAMPLE 6

B-Cell Proliferation Assay

A generalized procedure for a standard cellular B-cell proliferation assay that can be used to test compounds disclosed in this application is as follows.

B-cells are purified from spleens of 8-16 week old Balb/c mice using a B-cell isolation kit (Miltenyi Biotech, Cat # 130-090-862). Testing compounds are diluted in 0.25% DMSO and incubated with $2.5 \times 10^5$ purified mouse splenic B-cells for 30 min prior to addition of 10 µg/ml of an anti-mouse IgM antibody (Southern Biotechnology Associates Cat # 1022-01) in a final volume of 100 µl. Following 24 hr incubation, 1 µCi $^3$H-thymidine is added and plates are incubated an additional 36 hr prior to harvest using the manufacturer's protocol for SPA[$^3$H] thymidine uptake assay system (Amersham Biosciences # RPNQ 0130). SPA-bead based fluorescence is counted in a microbeta counter (Wallace Triplex 1450, Perkin Elmer).

EXAMPLE 7

T Cell Proliferation Assay

A generalized procedure for a standard T cell proliferation assay that can be used to test compounds disclosed in this application is as follows.

T cells are purified from spleens of 8-16 week old Balb/c mice using a Pan T cell isolation kit (Miltenyi Biotech, Cat # 130-090-861). Testing compounds are diluted in 0.25% DMSO and incubated with $2.5 \times 10^5$ purified mouse splenic T cells in a final volume of 100 µl in flat clear bottom plates precoated for 90 min at 37° C. with 10 µg/ml each of anti-CD3 (BD # 553057) and anti-CD28 (BD # 553294) antibodies. Following 24 hr incubation, 1 µCi $^3$H-thymidine is added and plates incubated an additional 36 hr prior to harvest using the manufacturer's protocol for SPA[$^3$H] thymidine uptake assay system (Amersham Biosciences # RPNQ 0130). SPA-bead based fluorescence was counted in a microbeta counter (Wallace Triplex 1450, Perkin Elmer).

EXAMPLE 8

CD86 Inhibition Assay

A generalized procedure for a standard assay for the inhibition of B cell activity that can be used to test compounds disclosed in this application is as follows.

Total mouse splenocytes are purified from spleens of 8-16 week old Balb/c mice by red blood cell lysis (BD Pharmingen #555899). Testing compounds are diluted to 0.5% DMSO and incubated with $1.25 \times 10^6$ splenocytes in a final volume of 200 µl in flat clear bottom plates (Falcon 353072) for 60 min at 37° C. Cells are then stimulated with the addition of 15 µ[g/ml IgM (Jackson ImmunoResearch 115-006-020), and incubated for 24 hr at 37° C., 5% $CO_2$. Following the 24 hr incubation, cells are transferred to conical bottom clear 96-well plates and pelleted by centrifugation at 1200×g×5 min. Cells are preblocked by CD16/CD32 (BD Pharmingen #553142), followed by triple staining with CD19-FITC (BD Pharmingen #553785), CD86-PE (BD Pharmingen #553692), and 7AAD (BD Pharmingen #51-68981E). Cells are sorted on a BD FACSCalibur and gated on the $CD19^+$/ $7AAD^-$ population. The levels of CD86 surface expression on the gated population is measured versus test compound concentration.

EXAMPLE 9

B-ALL Cell Survival Assay

The following is a procedure for a standard B-ALL cell survival study using an XTT readout to measure the number of viable cells. This assay can be used to test compounds disclosed in this application for their ability to inhibit the survival of B-ALL cells in culture. One human B-cell acute lymphoblastic leukemia line that can be used is SUP-B15, a human Pre-B-cell ALL line that is available from the ATCC.

SUP-B15 pre-B-ALL cells are plated in multiple 96-well microtiter plates in 100 µl of Iscove's media+20% FBS at a concentration of $5 \times 10^5$ cells/ml. Test compounds are then added with a final conc. of 0.4% DMSO. Cells are incubated at 37° C. with 5% $CO_2$ for up to 3 days. After 3 days cells are split 1:3 into fresh 96-well plates containing the test compound and allowed to grow up to an additional 3 days. After each 24 h period, 50 ul of an XTT solution (Roche) is added to one of the replicate 96-well plates and absorbance readings are taken at 2, 4 and 20 hours following manufacturer's directions. The reading taken with an OD for DMSO only treated cells within the linear range of the assay (0.5-1.5) is then taken and the percentage of viable cells in the compound treated wells are measured versus the DMSO only treated cells.

EXAMPLE 10

The compounds disclosed in the examples above are tested in the Btk biochemical assay described herein (Example 4) and certain of those compounds exhibit an $IC_{50}$ value less than or equal to 1 micromolar. Certain of those compounds exhibit an $IC_{50}$ value less than or equal to 25 nM. Certain of those compounds exhibit an $IC_{50}$ value less than or equal to 5 nM.

Some of the compounds disclosed in the examples above are tested in the B-cell proliferation assay (as described in Example 6) and exhibit an $IC_{50}$ value less than or equal to 10 micromolar. Certain of those compounds exhibit an $IC_{50}$ value less than or equal to 500 nM. Certain of those compounds exhibit an $IC_{50}$ value less than or equal to 50 nM in this assay.

Certain of those compounds do not inhibit T-cell proliferation and have $IC_{50}$ values greater than or equal to 5 micromolar when they are assayed under conditions described herein (as described in Example 7).

Certain compounds disclosed herein exhibit $IC_{50}$ values for inhibition of T-cell proliferation that are at least 3-fold, and in some instances 10-fold, or even 100-fold greater than the $IC_{50}$ values of those compounds for inhibition of B-cell proliferation.

Some of the compounds disclosed herein are tested in an assay for inhibition of B cell activity (under the conditions described in Example 8), and exhibit an $IC_{50}$ value less than or equal to 10 micromolar. Certain of those compounds exhibit an $IC_{50}$ value less than or equal to 0.5 micromolar. Certain of those compounds exhibit an $IC_{50}$ value less than or equal to 100 nM in this assay.

Some of the compounds disclosed herein are tested in a B-cell leukemia cell survival assay (under the conditions described in Example 9), and exhibit an $IC_{50}$ value less than or equal to 10 micromolar.

Some of the compounds disclosed herein exhibit both biochemical and cell-based activity. For example, some of the compounds disclosed herein exhibit an $IC_{50}$ value less than or equal to 1 micromolar in the Btk biochemical assay described herein (Example 4) and an $IC_{50}$ value less than or equal to 10 micromolar in at least one of the cell-based assays (other than the T-cell assay) described herein (Examples 7, 8, 10 or 11). Certain of those compounds exhibit an $IC_{50}$ value less than or equal to 50 nM in the Btk biochemical assay described herein (Example 4) and an $IC_{50}$ value less than or equal to 500 nM in at least one of the cell-based assays (other than the T-cell assay) described herein (Examples 7, 8, 10 or 11). Certain of those compounds exhibit an $IC_{50}$ value less than or equal to 10 nM and an $IC_{50}$ value less than or equal to 100 nM in at least one of the cell-based assays (other than the T-cell assay) described herein (Examples 7, 8, 10 or 11).

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A compound of Formula I:

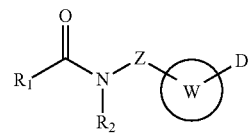

(Formula I)

or a pharmaceutically acceptable salt thereof, wherein
$R_1$ is:

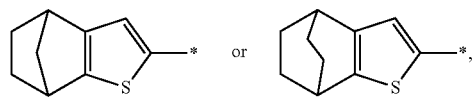

$R_2$ is H or $CH_3$;
Z is chosen from phenylene and pyridylidene wherein phenylene and pyridylidene are optionally substituted with one or more groups independently chosen from CN, halo, hydroxyl, optionally substituted lower alkyl, and optionally substituted lower alkoxy;

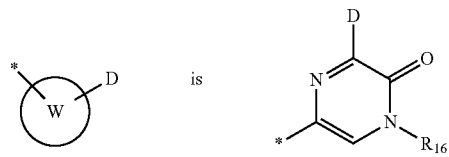

which is optionally substituted with one or two groups chosen from hydroxy, cyano, halo, optionally substituted lower alkyl, and optionally substituted lower alkoxy;
$R_{16}$ is independently chosen from hydrogen, cyano, optionally substituted cycloalkyl, and optionally substituted lower alkyl;
D is —$NHR_7$; and
$R_7$ is chosen from optionally substituted aryl and optionally substituted heteroaryl.

2. The compound of claim 1 wherein $R_1$ is chosen selected from

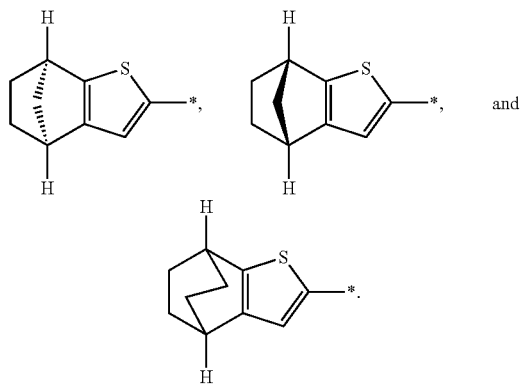

3. The compound of claim 2 wherein the compound is of Formula II, wherein:

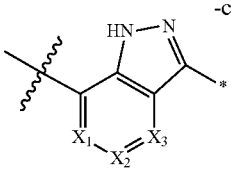
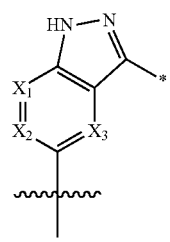

-continued

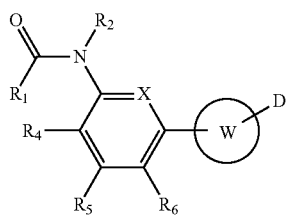 (Formula II)

X is CR₃ or N;

R₃ is chosen from H, CH₃, F and Cl;

R₄ is chosen from H, CH₃, F and Cl;

R₅ is chosen from H, CH₃, F and Cl; and

R₆ is chosen from H, CH₃, F and Cl.

4. The compound of claim 3 wherein the compound is of Formula III:

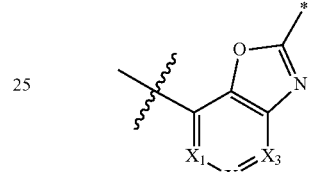
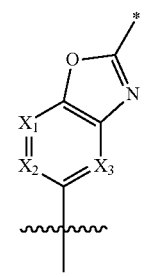

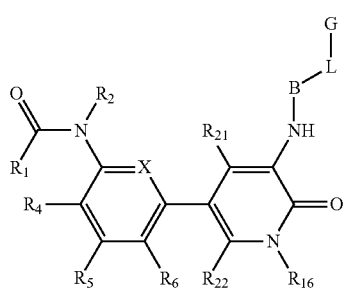 Formula III wherein

B is chosen from optionally substituted phenylene, optionally substituted pyridylidene, optionally substituted pyrazolyl, optionally substituted 2-oxo-1,2-dihydropyridinyl,

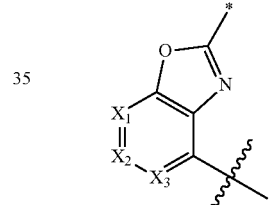
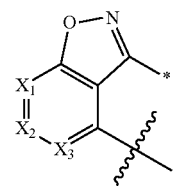

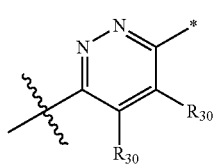

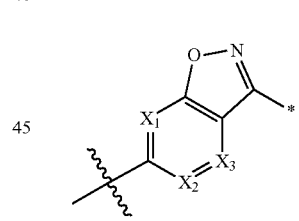
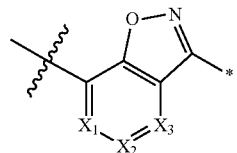

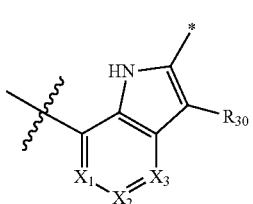

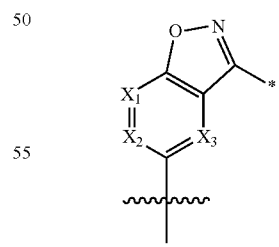
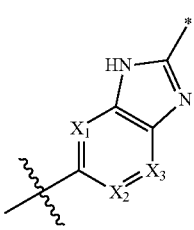

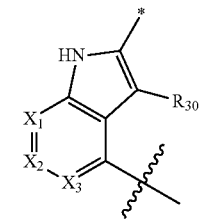
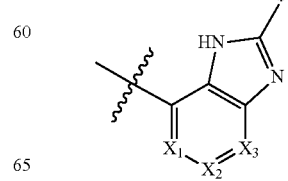
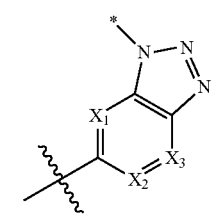

-continued

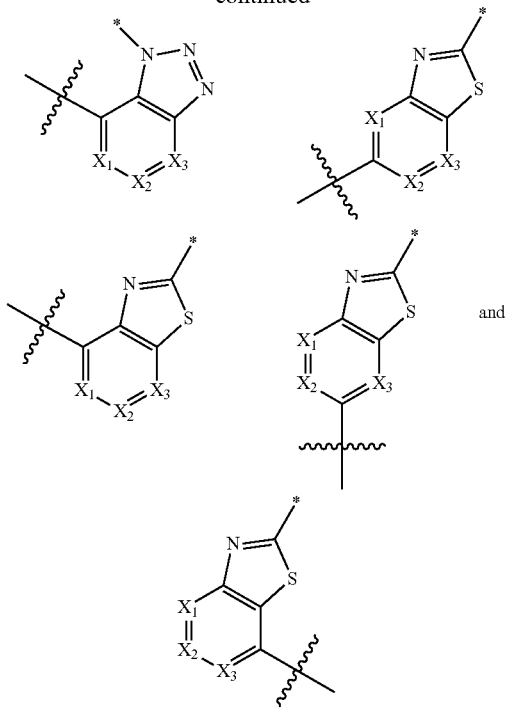

wherein

\* indicates the point of attachment to the group -L-G and the broken bond

indicates the point of attachment to the —N(H)— group;

each $X_1$ is independently chosen from N and $CR_{31}$;

each $X_2$ is independently chosen from N and $CR_{31}$; and each $X_3$ is independently chosen from N and $CR_{31}$; and wherein no more than one of $X_1$, $X_2$, and $X_3$ is N, each $R_{30}$ is independently chosen from hydrogen, hydroxy, cyano, halo, optionally substituted lower alkyl, and optionally substituted lower alkoxy;

each $R_{31}$ is independently chosen from hydrogen, hydroxy, cyano, halo, optionally substituted lower alkyl, and optionally substituted lower alkoxy;

L is chosen from optionally substituted $C_0$-$C_4$alkylene, —O—optionally substituted $C_0$-$C_4$alkylene, —($C_0$-$C_4$alkylene)(SO)—, —($C_0$-$C_4$alkylene)($SO_2$)—; and —($C_0$-$C_4$alkylene)(C=O)—; and G is chosen from hydrogen, halo, hydroxy, alkoxy, nitro, optionally substituted alkyl, optionally substituted amino, optionally substituted carbamimidoyl, optionally substituted heterocycloalkyl, optionally substituted cycloalkyl, optionally substituted aryl, and optionally substituted heteroaryl.

5. The compound of claim 4 wherein the compound is of Formula V, wherein U is N or CH:

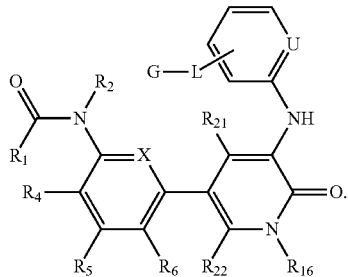

(Formula V)

6. The compound of claim 3 wherein the compound is of Formula IV:

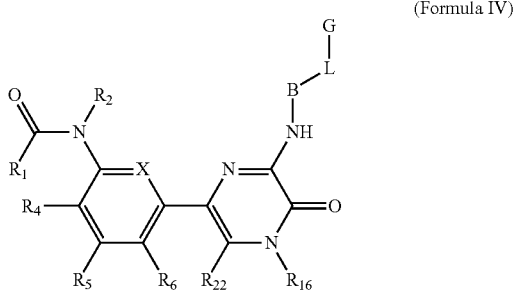

(Formula IV)

wherein

B is chosen from optionally substituted phenylene, optionally substituted pyridylidene, optionally substituted pyrazolyl, optionally substituted 2-oxo-1,2-dihydropyridinyl,

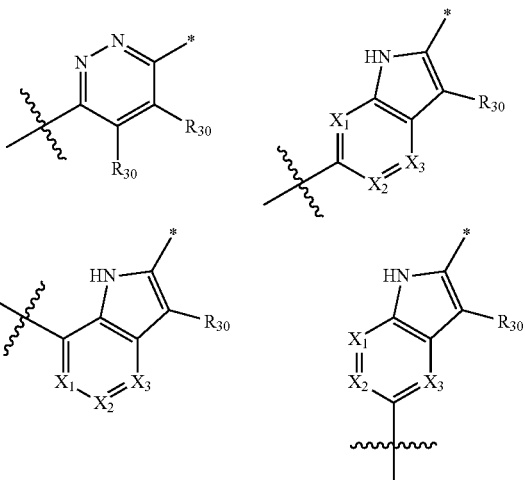

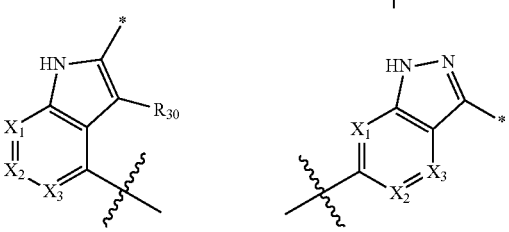

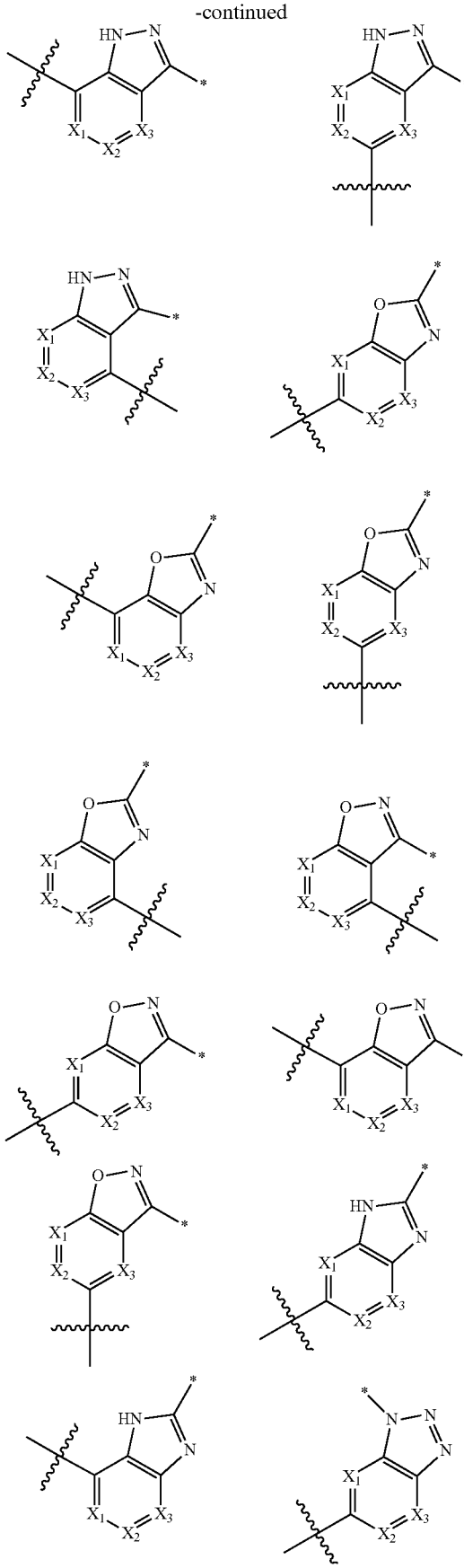

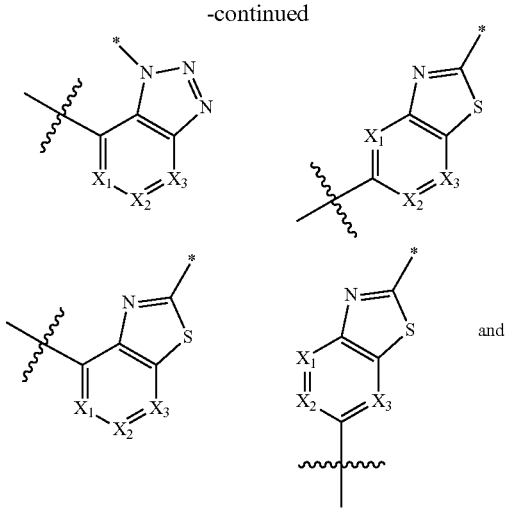

wherein

* indicates the point of attachment to the group -L-G and the broken bond

indicates the point of attachment to the —N(H)— group;

each $X_1$ is independently chosen from N and $CR_{31}$;

each $X_2$ is independently chosen from N and $CR_{31}$; and each $X_3$ is independently chosen from N and $CR_{31}$; and wherein no more than one of $X_1$, $X_2$, and $X_3$ is N, each $R_{30}$ is independently chosen from hydrogen, hydroxy, cyano, halo, optionally substituted lower alkyl, and optionally substituted lower alkoxy;

each $R_{31}$ is independently chosen from hydrogen, hydroxy, cyano, halo, optionally substituted lower alkyl, and optionally substituted lower alkoxy;

L is chosen from optionally substituted $C_0$-$C_4$alkylene, —O—optionally substituted $C_0$-$C_4$alkylene, —($C_0$-$C_4$alkylene)(SO)—, —($C_0$-$C_4$alkylene)($SO_2$)—; and —($C_0$-$C_4$alkylene)(C=O)—; and G is chosen from hydrogen, halo, hydroxy, alkoxy, nitro, optionally substituted alkyl, optionally substituted amino, optionally substituted carbamimidoyl, optionally substituted heterocycloalkyl, optionally substituted cycloalkyl, optionally substituted aryl, and optionally substituted heteroaryl.

7. The compound of claim 6 wherein the compound is of Formula VI, wherein U is N or CH:

(Formula IV)

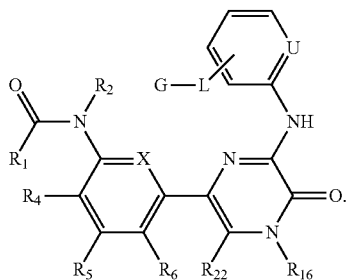

8. The compound of claim 7 wherein L is a covalent bond, —CH$_2$—, or —(C═O)—.

9. The compound of claim 8 wherein G is chosen from
hydrogen,
hydroxy,
N-methylethanolamino,
—N(C$_1$-C$_6$ alkyl)$_2$,
optionally substituted morpholin-4-yl,
optionally substituted piperazin-1-yl,
optionally substituted piperazin-2-yl,
optionally substituted homopiperazin-1-yl, and
optionally substituted cyclopropyl.

10. The compound of claim 1, wherein Z is phenylene which is optionally substituted with one or more groups independently chosen from CN, halo, hydroxyl, lower alkyl, and lower alkoxy.

11. The compound of claim 1, wherein Z is pyridylidene which is optionally substituted with one or more groups independently chosen from CN, halo, hydroxyl, lower alkyl, and lower alkoxy.

12. The compound of claim 1, wherein Z is phenylene which is optionally substituted with one or more groups independently chosen from CH$_3$, F, and Cl.

13. The compound of claim 1, wherein Z is pyridylidene which is optionally substituted with one or more groups independently chosen from CH$_3$, F, and Cl.

14. The compound of claim 1, wherein R$_{16}$ is H or CH$_3$.

15. The compound of claim 1, wherein
D is —N(H)—B-L-G,
B is para-phenylene, meta-phenylene, para-pyridylidene, or, pyrazol-4-yl,
L is a covalent bond, —(C═O)—, —CH$_2$—, —CH$_2$(C═O)—, —SO$_2$— or —CH(CH$_3$)(C═O)—, and
G is hydrogen, hydroxy, N-methylethanolamino, —N(C$_1$-C$_6$ alkyl)$_2$, optionally substituted morpholin-4-yl, optionally substituted piperazin-1-yl, optionally substituted piperazin-2-yl, optionally substituted homopiperazin-1-yl, or optionally substituted cyclopropyl.

16. The compound of claim 15, wherein G is hydrogen, —N(C$_1$-C$_6$ alkyl)$_2$, morpholin-4-yl, 4-acyl-piperazin-1-yl, 4-lower alkyl-piperazin-1-yl, 3-oxo-piperazin-1-yl, 3-oxopiperazin-2-yl, homopiperazin-1-yl, 4-lower alkyl-homopiperazin-1-yl, or cyclopropyl.

17. The compound of claim 10, wherein
R$_{16}$ is H or CH$_3$,
D is —N(H)—B-L-G,
B is para-phenylene, meta-phenylene, para-pyridylidene, or, pyrazol-4-yl,
L is a covalent bond, —(C═O)—, —CH$_2$—, —CH$_2$(C═O)—, —SO$_2$— or —CH(CH$_3$)(C═O)—, and
G is hydrogen, hydroxy, N-methylethanolamino, —N(C$_1$-C$_6$ alkyl)$_2$, optionally substituted morpholin-4-yl, optionally substituted piperazin-1-yl, optionally substituted piperazin-2-yl, optionally substituted homopiperazin-1-yl, or optionally substituted cyclopropyl.

18. The compound of claim 17, wherein G is hydrogen, —N(C$_1$-C$_6$ alkyl)$_2$, morpholin-4-yl, 4-acyl-piperazin-1-yl, 4-lower alkyl-piperazin-1-yl, 3-oxo-piperazin-1-yl, 3-oxopiperazin-2-yl, homopiperazin-1-yl, 4-lower alkyl-homopiperazin-1-yl, or cyclopropyl.

19. The compound of claim 12, wherein
R$_{16}$ is H or CH$_3$,
D is —N(H)—B-L-G,
B is para-phenylene, meta-phenylene, para-pyridylidene, or, pyrazol-4-yl,
L is a covalent bond, —(C═O)—, —CH$_2$—, —CH$_2$(C═O)—, —SO$_2$— or —CH(CH$_3$)(C═O)—, and
G is hydrogen, hydroxy, N-methylethanolamino, —N(C$_1$-C$_6$ alkyl)$_2$, optionally substituted morpholin-4-yl, optionally substituted piperazin-1-yl, optionally substituted piperazin-2-yl, optionally substituted homopiperazin-1-yl, or optionally substituted cyclopropyl.

20. The compound of claim 19, wherein G is hydrogen, —N(C$_1$-C$_6$ alkyl)$_2$, morpholin-4-yl, 4-acyl-piperazin-1-yl, 4-lower alkyl-piperazin-1-yl, 3-oxo-piperazin-1-yl, 3-oxopiperazin-2-yl, homopiperazin-1-yl, 4-lower alkyl-homopiperazin-1-yl, or cyclopropyl.

21. The compound of claim 1, wherein said compound is selected from:
N-{3-[6-({4-[(2S)-1,4-dimethyl-3-oxopiperazin-2-yl]phenyl}amino)-4-methyl-5-oxo -4,5-dihydropyrazin-2-yl]-2-methylphenyl}-(4S, 7R)-4,7-methano-4,5,6,7-tetrahydro-1-benzothiophene-2-carboxamide;
N-{3-[6-({4-[(2R)-1,4-dimethyl-3-oxopiperazin-2-yl]phenyl}amino)-4-methyl-5-oxo -4,5-dihydropyrazin-2-yl]-2-methylphenyl}-(4S, 7R)-4,7-methano-4,5,6,7-tetrahydro-1-benzothiophene-2-carboxamide;
N-{3-[6-({4-[(2S)-1,4-dimethyl-3-oxopiperazin-2-yl]phenyl}amino)-4-methyl-5-oxo -4,5-dihydropyrazin-2-yl]-2-methylphenyl}-(4R, 7S)-4,7-methano-4,5,6,7-tetrahydro-1-benzothiophene-2-carboxamide;
N-{3-[6-({4-[(2R)-1,4-dimethyl-3-oxopiperazin-2-yl]phenyl}amino)-4-methyl-5-oxo -4,5-dihydropyrazin-2-yl]-2-methylphenyl}-(4R, 7S)-4,7-methano-4,5,6,7-tetrahydro-1-benzothiophene-2-carboxamide;
N-(5-(6-(4-(4-(dimethylamino)piperidin-1-yl)phenylamino)-4-methyl-5-oxo-4,5-dihydropyrazin-2-yl)-2-fluorophenyl)-4,7-methano-4,5,6,7-tetrahydrobenzo[b]thiophene-2-carboxamide;
N-(2-fluoro-5-(4-methyl-6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide;
N-(2,4-difluoro-5-(4-methyl-6-(4-(4-methylpiperazin-1-yl)phenylamino)-5-oxo-4,5-dihydropyrazin-2-yl)phenyl)-4,7-methano-4,5,6,7-tetrahydrobenzo[b]thiophene-2-carboxamide;
N-(2-methyl-4-fluoro-5-(4-methyl-6-(4-(4-methylpiperazin-1-yl)phenylamino)-5-oxo -4,5-dihydropyrazin-2-yl)phenyl)-4,7-methano-4,5,6,7-tetrahydrobenzo[b]thiophene-2-carboxamide;
N-(2-chloro-4-methyl-5-(4-methyl-6-(4-(4-methylpiperazin-1-yl)phenylamino)-5-oxo -4,5-dihydropyrazin-2-yl)phenyl)-4,7-methano-4,5,6,7-tetrahydrobenzo[b]thiophene-2-carboxamide;
N-(5-fluoro-6-(4-methyl-6-(4-(4-methylpiperazin-1-yl)phenylamino)-5-oxo-4,5-dihydropyrazin-2-yl)pyridin-2-yl)-4,7-methano-4,5,6,7-tetrahydrobenzo[b]thiophene-2-carboxamide;

N-(4-fluoro-2-methyl-3-(6-(4-(4-methylpiperazin-1-yl) phenylamino)-5-oxo-4,5-dihydropyrazin-2-yl)phenyl)-4,7-methano-4,5,6,7-tetrahydrobenzo[b]thiophene-2-carboxamide;

N-(3-fluoro-6-(4-methyl-6-(4-(4-methylpiperazin-1-yl) phenylamino)-5-oxo-4,5-dihydropyrazin-2-yl)pyridin-2-yl)-4,7-methano-4,5,6,7-tetrahydrobenzo[b] thiophene-2-carboxamide;

N-(5-(6-(1-ethyl-1H-pyrazol-4-ylamino)-4-methyl-5-oxo-4,5-dihydropyrazin-2-yl)-2-fluorophenyl)-4,7-methano-4,5,6,7-tetrahydrobenzo[b]thiophene-2-carboxamide;

N-(3-(6-(1-ethyl-1H-pyrazol-4-ylamino)-4-methyl-5-oxo-4,5-dihydropyrazin-2-yl) -2,6-difluorophenyl)-4,7-methano-4,5,6,7-tetrahydrobenzo[b]thiophene-2-carboxamide;

N-(3-(6-(1-ethyl-1H-pyrazol-4-ylamino)-4-methyl-5-oxo-4,5-dihydropyrazin-2-yl)-6-fluoro-2-methylphenyl)-4,7-methano-4,5,6,7-tetrahydrobenzo[b] thiophene-2-carboxamide;

N-(2-chloro-3-(6-(1-ethyl-1H-pyrazol-4-ylamino)-4-methyl-5-oxo-4,5-dihydropyrazin-2-yl)-6-methylphenyl)-4,7-methano-4,5,6,7-tetrahydrobenzo[b]thiophene-2-carboxamide;

N-(6-(6-(1-ethyl-1H-pyrazol-4-ylamino)-4-methyl-5-oxo-4,5-dihydropyrazin-2-yl)-3-fluoropyridin-2-yl)-4,7-methano-4,5,6,7-tetrahydrobenzo[b]thiophene-2-carboxamide;

N-(6-(6-(1-ethyl- 1H-pyrazol-4-ylamino)-4-methyl-5-oxo-4,5-dihydropyrazin-2-yl)-5-fluoropyridin-2-yl)-4,7-methano-4,5,6,7-tetrahydrobenzo[b]thiophene-2-carboxamide;

N-(5-(6-(1H-pyrazol-4-ylamino)-4-methyl-5-oxo-4,5-dihydropyrazin-2-yl)-2-fluorophenyl)-4,7-methano-4,5,6,7-tetrahydrobenzo[b]thiophene-2-carboxamide;

N-(3-(6-(1H-pyrazol-4-ylamino)-4-methyl-5-oxo-4,5-dihydropyrazin-2-yl)-2,6-difluorophenyl)-4,7-methano-4,5,6,7-tetrahydrobenzo[b]thiophene-2-carboxamide;

N-(3-(6-(1H-pyrazol-4-ylamino)-4-methyl-5-oxo-4,5-dihydropyrazin-2-yl)-6-fluoro-2-methylphenyl)-4,7-methano-4,5,6,7-tetrahydrobenzo[b]thiophene-2-carboxamide;

N-(3-(6-(1H-pyrazol-4-ylamino)-4-methyl-5-oxo-4,5-dihydropyrazin-2-yl)-2-chloro -6-methylphenyl)-4,7-methano-4,5,6,7-tetrahydrobenzo[b]thiophene-2-carboxamide;

N-(6-(6-(1H-pyrazol-4-ylamino)-4-methyl-5-oxo-4,5-dihydropyrazin-2-yl)-3-fluoropyridin-2-yl)-4,7-methano-4,5,6,7-tetrahydrobenzo[b]thiophene-2-carboxamide;

N-(6-(6-(1H-pyrazol-4-ylamino)-4-methyl-5-oxo-4,5-dihydropyrazin-2-yl)-5-fluoropyridin-2-yl)-4,7-methano-4,5,6,7-tetrahydrobenzo[b]thiophene-2-carboxamide;

N-(2-fluoro-5-(4-methyl-6-(4-(1-methylpiperidin-4-yl) phenylamino)-5-oxo-4,5-dihydropyrazin-2-yl)phenyl)-4,7-methano-4,5,6,7-tetrahydrobenzo[b]thiophene-2-carboxamide;

N-(2-fluoro-5-(6-(4-((isopropyl(methyl)amino)methyl) phenylamino)-4-methyl-5-oxo -4,5-dihydropyrazin-2-yl)phenyl)-4,7-methano-4,5,6,7-tetrahydrobenzo[b] thiophene-2-carboxamide;

N-(2,6-difluoro-3-(6-(4-((isopropyl(methyl)amino)methyl)phenylamino)-4-methyl-5-oxo-4,5-dihydropyrazin-2-yl)phenyl)-4,7-methano-4,5,6,7-tetrahydrobenzo[b]thiophene-2-carboxamide;

N-(6-fluoro-3-(6-(4-((isopropyl(methyl)amino)methyl) phenylamino)-4-methyl-5-oxo -4,5-dihydropyrazin-2-yl)-2-methylphenyl)-4,7-methano-4,5,6,7-tetrahydrobenzo[b]thiophene-2-carboxamide;

N-(2-chloro-3-(6-(4-((isopropyl(methyl)amino)methyl) phenylamino)-4-methyl-5-oxo -4,5-dihydropyrazin-2-yl)-6-methylphenyl)-4,7-methano-4,5,6,7-tetrahydrobenzo[b]thiophene-2-carboxamide;

N-(3-fluoro-6-(6-(4-((isopropyl(methyl)amino)methyl) phenylamino)-4-methyl-5-oxo -4,5-dihydropyrazin-2-yl)pyridin-2-yl)-4,7-methano-4,5,6,7-tetrahydrobenzo [b]thiophene-2-carboxamide;

N-(5-fluoro-6-(6-(4-((isopropyl(methyl)amino)methyl) phenylamino)-4-methyl-5-oxo -4,5-dihydropyrazin-2-yl)pyridin-2-yl)-4,7-methano-4,5,6,7-tetrahydrobenzo [b]thiophene-2-carboxamide;

N-{2-methyl-3-[4-methyl-6-({4-[(4-methylpiperazin-1-yl)carbonyl]phenyl}amino)-5-oxo-4,5-dihydropyrazin-2-yl]phenyl}-4,7-methano-4,5,6,7-tetrahydro-1-benzothiophene-2-carboxamide;

3-fluoro-N-[2-methyl-3-(4-methyl-6-{[4-(morpholin-4-ylcarbonyl)phenyl]amino}-5-oxo-4,5-dihydropyrazin-2-yl)phenyl]-4,7-methano-4,5,6,7-tetrahydro-1-benzothiophene-2-carboxamide;

N-(3-{6-[(4-{[(2-hydroxyethyl) (methyl)amino] methyl}phenyl)amino]-4-methyl-5-oxo-4,5-dihydropyrazin-2-yl}-2-methylphenyl)-4,7-methano-4,5,6,7-tetrahydro-1-benzothiophene-2-carboxamide;

N-{3-[6-(1H-indazol-5-ylamino)-4-methyl-5-oxo-4,5-dihydropyrazin-2-yl]-2-methylphenyl}-4,7-methano-4,5,6,7-tetrahydro-1-benzothiophene-2-carboxamide;

N-(2-fluoro-5-(4-methyl-6-(4-(4-methylpiperazin-1-yl) phenylamino)-5-oxo-4,5-dihydropyrazin-2-yl)phenyl)-4,7-ethano-4,5,6,7-tetrahydrobenzo[b]thiophene-2-carboxamide;

N-(2-fluoro-5-(4-methyl-6-(4-(4-methylpiperazin-1-yl) phenylamino)-5-oxo-4,5-dihydropyrazin-2-yl)phenyl)-4,7-ethano-4,5,6,7-tetrahydrobenzo[d]thiazole-2-carboxamide;

and pharmaceutically acceptable salts thereof.

22. A pharmaceutical composition comprising a compound of claim 1, together with at least one pharmaceutically acceptable vehicle chosen from carriers, adjuvants, and excipients.

23. A pharmaceutical composition of claim 22, wherein the composition is formulated in a form chosen from injectable fluids, aerosols, creams, gels, tablets, pills, capsules, syrups, ophthalmic solutions, and transdermal patches.

24. A packaged pharmaceutical composition comprising
a pharmaceutical composition of claim 22; and
instructions for using the composition to treat a patient suffering from a disease responsive to inhibition of Btk activity.

25. A method for inhibiting ATP hydrolysis, the method comprising contacting cells expressing Btk with a compound of claim 1 in an amount sufficient to detectably decrease the level of ATP hydrolysis in vitro.

26. The method of claim 25 wherein the cells are present in a mammal.

27. The method of claim 26 wherein the mammal is a human.

28. The method of claim 26 wherein the mammal is chosen from cats and dogs.

29. A method for determining the presence of Btk in a sample, comprising contacting the sample with a compound of claim 1 under conditions that permit detection of Btk activity, detecting a level of Btk activity in the sample, and therefrom determining the presence or absence of Btk in the sample.

30. A method for inhibiting B-cell activity comprising contacting cells expressing Btk with a compound of claim 1, in an amount sufficient to detectably decrease B-cell activity in vitro.

* * * * *